(12) United States Patent
Rudnicki et al.

(10) Patent No.: US 7,541,183 B2
(45) Date of Patent: Jun. 2, 2009

(54) GROWTH AND DIFFERENTIATION OF ADULT MUSCLE STEM CELLS WITH ACTIVATORS OR INHIBITORS OF WNT SIGNALING

(75) Inventors: Michael Rudnicki, Gloucester (CA); Patrick Seale, Brookline, MA (US); Anna Polesskaya, Villejuif (FR); Anouk Fortin, Gloucester (CA)

(73) Assignee: Ottawa Health Research Institute, Ottawa, Ontario (CA)

( * ) Notice: Subject to any disclaimer, the term of this patent is extended or adjusted under 35 U.S.C. 154(b) by 238 days.

(21) Appl. No.: 11/318,419

(22) Filed: Dec. 22, 2005

(65) Prior Publication Data
US 2006/0171931 A1 Aug. 3, 2006

Related U.S. Application Data

(63) Continuation of application No. PCT/CA2004/000941, filed on Jun. 25, 2004.

(60) Provisional application No. 60/482,014, filed on Jun. 25, 2003.

(51) Int. Cl.
*C12N 15/00* (2006.01)
*C12N 15/02* (2006.01)
(52) U.S. Cl. .................. 435/373; 435/354; 435/366
(58) Field of Classification Search .............. None
See application file for complete search history.

(56) References Cited

U.S. PATENT DOCUMENTS

| 5,851,984 | A | 12/1998 | Matthews et al. |
|---|---|---|---|
| 6,080,575 | A | 6/2000 | Heidtmann et al. |
| 6,159,462 | A | 12/2000 | Matthews et al. |
| 6,165,748 | A | 12/2000 | Racie et al. |
| 6,337,184 | B1 | 1/2002 | Miller |
| 6,465,249 | B2 | 10/2002 | Reya et al. |
| 2001/0041668 | A1* | 11/2001 | Baron et al. ............. 514/2 |
| 2003/0040051 | A1 | 2/2003 | Bhanot et al. |
| 2004/0014209 | A1* | 1/2004 | Lassar et al. ........... 435/366 |

FOREIGN PATENT DOCUMENTS

CA 2 353 804 1/2003

OTHER PUBLICATIONS

Gallicchio et al. (1980) Blood 53:1150-1152.*
M.A. Rudnicki, XP002302213, "Molecular Of Adult Stem Cell Specification in Muscle", Abstract # 487.1, FASEB Journal, vol. 17, No. 4-5, (2003).
A. Polesskaya et al., XP002302214, "Wnt Signaling Induces The Myogenic Specification Of Resident CD45+ Adult Stem Cells During Muscle Regeneration." Cell, vol. 113, No. 7, pp. 841-852 (2003).
T. Reya et al., XP002975077, "A Role For Wnt Signalling In Self-Renewal Of Haematopoietic Stem Cells", NATURE, vol. 423, pp. 409-414,(2003).

A. Asakura, et al., "Myogenic Specification Of Side Population Cells In Skeletal Muscle", The Journal of Cell Biology, vol. 159, pp. 123-134 (2002).
A. Gritti et al., "Epidermal And Fibroblast Growth Factors Behave As Mitrogenic Regulators For A Single Multipotent Stem Cell-Like Population From The Subventricular Region Of The Adult Mouse Forebrain", The Journal of Neuroscience, vol. 19, No. 9, pp. 3287-3297 (1999).
E. Gussoni et al., "Dystrophni Expression In The mdx Mouse Restored By Stem Cell Transplantation", Nature, vol. 401, pp. 390-394 (1999).
C. M. Hedgepeth et al., "Activation Of The Wnt Signaling Pathway: A Molecular Mechanism For Lithium Action", Developmental Biology, Article No. DB978552, vol. 185, pp. 82-91 (1997).
A.M. Hierlihy et al. "The Post-Natal Heart Contains A Myocardial Stem Cell Population", FEBS Letters, vol. 530, pp. 239-243 (2002).
S. Hitoshi et al., "Notch Pathway Molecules Are Essential For The Maintenance, But Not The Generation, Of Mammalian Neural Stem Cells", Genes & Development, vol. 16, pp. 846-858 (2002).
P. Zhao, et al., "Embryonic Myogenesis Pathways in Muscle Regenertion", Developmental Dynamics, vol. 229, pp. 380-392 (2004).
K.A. Jackson, et al., "Hematopoietic Potential Of Stem Cells Isolated From Murine Skeletal Muscle", Proc. Natl. Acad. Sci., vol. 96, No. 25, pp. 14482-14486 (1999).
G.J. Madlambayan et al., "Cutting Edge Communication", Journal of Hematotherapy & Stem Cell Research, vol. 10, pp. 481-492 (2001).
S.L. McKinney-Freeman, et al., "Muscle-Derived Hematopoietic Stem Cells Are Hematopoietic In Origin", Proc. Natl. Acad. Sci., vol. 99, No. 3, pp. 1341-1346 (2002).
L.A. Megeney, et al., "MyoD Is Required For Myogenic Stem Cell Function In Adult Skeletal Muscle", Genes & Development, vol. 10, pp. 1173-1183 (1996).
L.A. Megeney et al., "Severe Cardiomyopathy In Mice Lacking Dystrophin And MyoD", Proc. Natl. Acad. Sci. USA, vol. 96, pp. 220-225 (1999).
C. Shawber, et al., "Notch Signaling Inhibits Muscle Cell Differentiation Through A CBFI-Independent Pathway", Development, vol. 122, pp. 3765-3773 (1996).
H. Shimizu, et al., "Transformation By Wnt Family Proteins Correlates with Regulation of Beta-Catenin[1]", Cell Growth & Differentiation, vol. 8, pp. 1349-1358 (1997).
S. Tajbakhsh, et al., "Lineage Restriction Of The Myogenic Conversion Factor myf-5 In The Brain", Development, vol. 121, pp. 4077-4083 (1995).

(Continued)

*Primary Examiner*—Deborah Crouch
(74) *Attorney, Agent, or Firm*—Winston & Strawn LLP

(57) ABSTRACT

Compositions and methods for modulating proliferation and/or lineage commitment of stem cells by modulating the Wnt signalling pathways. Modulators of the Wnt signalling pathways and screening methods to identify modulators are also provided. The methods of the invention may be conducted in vitro or in vivo to induce or inhibit stem cell proliferation and/or lineage commitment, and are particularly useful for in vivo stimulation of proliferation and/or lineage commitment of resident stem cells in a tissue.

13 Claims, 10 Drawing Sheets

OTHER PUBLICATIONS

K. Willert, et al., XP-002279471, "Wnt Proteins Are Lipid-Modified And Can Act As Stem Cell Growth Factors", Nature, vol. 423, pp. 448-452 (2003).

Maeda, et al., "Prognostic Value of Vascular Endothelial Growth Factor Expression in Gastric Carcinoma", Cancer, vol. 77, No. 5, pp. 858-863 (1996).

* cited by examiner

Days 1-14

Daily IP injection
of LiCl (2 mg/kg)
or PBS (control)

Day 10

Cardiotoxin
injury in TA
muscle

Day 15

X-Gal staining
and Blue cell
count

SEQUENCE LISTING

```
<160> NUMBER OF SEQ ID NOS: 26

<210> SEQ ID NO 1
<211> LENGTH: 18
<212> TYPE: DNA
<213> ORGANISM: Human Wnt1 primer

<400> SEQUENCE: 1
acgtacagtg gccgcctg                                                       18

<210> SEQ ID NO 2
<211> LENGTH: 20
<212> TYPE: DNA
<213> ORGANISM: Human Wnt1 primer

<400> SEQUENCE: 2
acgcgcgtgt gcgtgcagtt                                                     20

<210> SEQ ID NO 3
<211> LENGTH: 19
<212> TYPE: DNA
<213> ORGANISM: Human Wnt3a primer

<400> SEQUENCE: 3
ggagatggtg gtagagaaa                                                      19

<210> SEQ ID NO 4
<211> LENGTH: 18
<212> TYPE: DNA
<213> ORGANISM: Human Wnt3a primer
```

```
<400> SEQUENCE: 4
atagacacgt gtgcactc                                                18

<210> SEQ ID NO 5
<211> LENGTH: 24
<212> TYPE: DNA
<213> ORGANISM: Human Wnt4 primer

<400> SEQUENCE: 5
agcccccgtt cgtgcctgcg gtcc                                         24

<210> SEQ ID NO 6
<211> LENGTH: 21
<212> TYPE: DNA
<213> ORGANISM: Human Wnt4 primer

<400> SEQUENCE: 6
actccacccg catgtgtgtc a                                            21

<210> SEQ ID NO 7
<211> LENGTH: 17
<212> TYPE: DNA
<213> ORGANISM: Human Wnt5a primer

<400> SEQUENCE: 7
aatggcmggc cacgtmt                                                 17

<210> SEQ ID NO 8
<211> LENGTH: 14
<212> TYPE: DNA
<213> ORGANISM: Human Wnt5a primer

<400> SEQUENCE: 8
tggattcgtt cccm                                                    14

<210> SEQ ID NO 9
<211> LENGTH: 22
<212> TYPE: DNA
<213> ORGANISM: Human Wnt5b primer

<400> SEQUENCE: 9
agtgcagaga ccggagatgt tc                                           22

<210> SEQ ID NO 10
<211> LENGTH: 19
<212> TYPE: DNA
<213> ORGANISM: Human Wnt5b primer

<400> SEQUENCE: 10
ggcaaagttc ttctcacgc                                               19

<210> SEQ ID NO 11
<211> LENGTH: 20
<212> TYPE: DNA
<213> ORGANISM: Human Wnt7a primer

<400> SEQUENCE: 11
agcgcggcgc tgcctgggcc                                              20

<210> SEQ ID NO 12
<211> LENGTH: 25
<212> TYPE: DNA
<213> ORGANISM: Human Wnt7a primer
```

```
<400> SEQUENCE: 12
cttcagaaag gtgggccgct tgttt                                          25

<210> SEQ ID NO 13
<211> LENGTH: 22
<212> TYPE: DNA
<213> ORGANISM: Human Wnt7b primer

<400> SEQUENCE: 13
ccgcacctcg ccgggggccg ac                                             22

<210> SEQ ID NO 14
<211> LENGTH: 22
<212> TYPE: DNA
<213> ORGANISM: Human Wnt7b primer

<400> SEQUENCE: 14
gtcggccccc ggcgaggtgc gg                                             22

<210> SEQ ID NO 15
<211> LENGTH: 20
<212> TYPE: DNA
<213> ORGANISM: Human Wnt10a primer

<400> SEQUENCE: 15
aaagtcccct acgagagccc                                                20

<210> SEQ ID NO 16
<211> LENGTH: 20
<212> TYPE: DNA
<213> ORGANISM: Human Wnt10a primer

<400> SEQUENCE: 16
cagcttccga cggaaagctt                                                20

<210> SEQ ID NO 17
<211> LENGTH: 20
<212> TYPE: DNA
<213> ORGANISM: Human Wnt10b primer

<400> SEQUENCE: 17
cggctgccgc accacagcgc                                                20

<210> SEQ ID NO 18
<211> LENGTH: 20
<212> TYPE: DNA
<213> ORGANISM: Human Wnt10b primer

<400> SEQUENCE: 18
cagcttggct ctaagccggt                                                20

<210> SEQ ID NO 19
<211> LENGTH: 19
<212> TYPE: DNA
<213> ORGANISM: Human sFRP1 primer

<400> SEQUENCE: 19
cgcccgtctg tctggaccg                                                 19

<210> SEQ ID NO 20
<211> LENGTH: 19
<212> TYPE: DNA
```

```
<213> ORGANISM: Human sFRP1 primer

<400> SEQUENCE: 20
ctcgcttgca cagagatgt                                               19

<210> SEQ ID NO 21
<211> LENGTH: 21
<212> TYPE: DNA
<213> ORGANISM: Human sFRP2 primer

<400> SEQUENCE: 21
ttcggccagc ccgacttctc c                                            21

<210> SEQ ID NO 22
<211> LENGTH: 23
<212> TYPE: DNA
<213> ORGANISM: Human sFRP2 primer

<400> SEQUENCE: 22
taggtcgtcg agacagacag ggg                                          23

<210> SEQ ID NO 23
<211> LENGTH: 22
<212> TYPE: DNA
<213> ORGANISM: Human sFRP3 primer

<400> SEQUENCE: 23
ammcctatgg attcaagtac tg                                           22

<210> SEQ ID NO 24
<211> LENGTH: 24
<212> TYPE: DNA
<213> ORGANISM: Human sFRP3 primer

<400> SEQUENCE: 24
ttgacmctta ccaagccgat cctt                                         24

<210> SEQ ID NO 25
<211> LENGTH: 23
<212> TYPE: DNA
<213> ORGANISM: Human sFRP4 primer

<400> SEQUENCE: 25
tggatagaca tcacaccaga tat                                          23

<210> SEQ ID NO 26
<211> LENGTH: 19
<212> TYPE: DNA
<213> ORGANISM: Human sFRP4 primer

<400> SEQUENCE: 26
cctgaagcct ctcttccca                                               19
```

GROWTH AND DIFFERENTIATION OF ADULT MUSCLE STEM CELLS WITH ACTIVATORS OR INHIBITORS OF WNT SIGNALING

CROSS-REFERENCE TO RELATED APPLICATIONS

This application is a continuation of International application No. PCT/CA2004/000941 filed Jun. 25, 2004, which claims the benefit of provisional application No. 60/482,014 filed Jun. 25, 2003, the entire content of each of which is expressly incorporated herein by reference thereto.

FIELD OF THE INVENTION

The present invention pertains to the field of stem cell therapeutics and in particular to methods of inducing or inhibiting stem cell proliferation or lineage commitment.

BACKGROUND OF THE INVENTION

The Wnt family of genes encode over twenty cysteine-rich, secreted glycoproteins that act by binding to Frizzled (Fzd) receptors on target cells. Binding of Wnt to Fzd can initiate signaling by one or several pathways. In the termed canonical pathway, activation of Disheveled leads to the inactivation of Glycogen syllthase lcinase-3β (GSK-3p), a cytoplasmic serine-threonine kinase. The gsk-3β target, β-catenin, is thereby stabilized and translocates to the nucleus where it activates TCF (T-cell-factor)-dependant transcription of specific promoters (Wodarz, 1998; Dierick, 1999). In the non-canonical or planar tissue polarity pathway, binding of Wnt to Fzd also activates Disheveled (Krasnow et al., (1995). Development 121,4095-4102) which in this case activates RhoA, a small g protein (Strutt et al., (1997). Nature 387, 292-295). RhoA then signals through JNK (Jun N-terminal lcinase) and Rock (Rho associated Kinase) (Boutros et al., (1998). Cell 94,109-118) to regulate cytoskeletal dynamics during gastrulation. Wnt proteins are also known to signal through modulation of intracellular calcium. This is thought to activate Protein Kinase C (PKC) (Sheldahl of al., (1999). Curr. Biol. 9,695-698) and leads to the nuclear translocation of the transcription factor NFAT. Recently, it has been determined that the Wnt signalling pathways are capable of directing cell fate determination in various tissues, including kidney (Labus, 1998 Vainio, 2000), CNS (Patapoutian, 2000), hematopoietic (Van Den Berg, 1998), and skeletal muscle (Cossu, 1999). Wnt signalling has also been implicated in postnatal wound healing and tissue regeneration in zebrafish and hydra (Hobmayer, 2000; Labus, 1998; Poss, 2000).

The involvement of Wnt signalling in the proliferation or differentiation of hematopoietic stem cells derived from fetal tissue or bone marrow has also been described. For example, U.S. Pat. Nos. 5,851,984 and 6,159,462 describe the use of Wnt polypeptides for enhancing the proliferation, differentiation and/or maintenance of hematopoietic stem or progenitor cells and U.S. Pat. No. 6,465,249 describes the use of β-catenin for the in vitro expansion of progenitor or stem cells, in particular hematopoietic stem cells. U.S. Pat. No. 6,165,748 describes novel proteins, the Frazzled proteins, which are involved in the Wnt signalling pathways and their use to induce expression of factors in and/or differentiation of tissues and organs. Canadian Patent Application No. 2,353, 804 describes the use of Wnt3a to stimulate myogenesis in P19 embryonal carcinoma cells and suggests that myogenesis may be controlled by modulation of Wnt activity, in particular that myogenesis may be inhibited by inhibition of a Wnt polypeptide.

U.S. Patent Application No. 20030040051 describes a set of novel members of the vertebrate Frizzled family of genes and methods of screening for compounds that affect the binding of a Wnt to the polypeptides encoded by these genes.

Stem cells have the potential for providing benefit in a variety of-clinical settings but a number of limitations to many potential applications have been encountered including, for example, obtaining a sufficient number of target cells and stimulating terminal differentiation of these stem cells into mature, tissue specific cells.

There is a need in the art for methods and compositions that are capable of modulating the growth, differentiation or both growth and differentiation of stem cells.

This background information is provided for the purpose of making known information believed by the applicant to be of possible relevance to the present invention. No admission is necessarily intended, nor should be construed, that any of the preceding information constitutes prior art against the present invention.

It is an object of the invention to overcome disadvantages of the prior art.

The above object is met by the combinations of features of the main claims, the sub-claims disclose further advantageous embodiments of the invention.

SUMMARY OF THE INVENTION

An embodiment of the present invention, which is not meant to be limiting in any manner, is to provide a use of the Wnt signalling pathways to modulate stem cell differentiation. In accordance with an aspect of the present invention, there is provided a method of modulating proliferation of a population of adult stem cells comprising contacting said population with one or more modulators of the Wnt signalling pathways.

In accordance with another aspect of the invention, there is provided a method of inducing the lineage commitment of a population of adult stem cells into progenitor cells comprising contacting said population with one or more activators of the Wnt signalling pathways.

In accordance with another aspect of the invention, there is provided a method of increasing the survival of a population of adult stem cells comprising contacting said population with one or more activators of the Wnt signalling pathways.

In accordance with another aspect of the invention, there is provided a method of inducing terminal differentiation of a population of myogenic precursor cells comprising contacting said population with one or more activators of the Wnt signalling pathways.

In accordance with another aspect of the invention, there is provided a method of inducing proliferation and/or lineage commitment of a population of resident stem cells in an adult tissue comprising contacting said cells with one or more activators of the Wnt signalling pathways.

In accordance with another aspect of the invention, there is provided a compound that binds to and inhibits the activity of a soluble Frizzled-related protein and is capable of inducing proliferation and/or lineage commitment of adult stem cells.

In accordance with another aspect of the invention, there is provided a compound that binds to and inhibits the activity of a Frizzed receptor and is capable of inhibiting proliferation and/or lineage commitment of adult stem cells.

In accordance with another aspect of the invention, there is provided a method of screening for compounds that modulate the Wnt signalling pathways comprising
(a) providing a test population of adult stem cells;
(b) contacting said test population with a candidate compound,
(c) monitoring proliferation of said test population;
(d) comparing proliferation of said test population with proliferation of a control population not contacted with said candidate compound,
wherein a difference in the proliferation of said test population and said control population is indicative of a compound that modulates the Wnt signalling pathways.

Also according to the present invention, there is provided a method of modulating proliferation, differentiation or both proliferation and differentiation of a population of CD45+: Sca1+ stem cells in a subject comprising,
administering a composition comprising one or more activators or inhibitors of wnt-signaling to the subject.

In a preferred embodiment, the modulating promotes proliferation, differentiation, or both proliferation and differentiation of the stem cells, and the composition comprises one or more activators of wnt-signaling, for example, but not limited to one or more wnt polypeptides, preferably human wnt polypeptides including, but not limited to Wnt 1, Wnt 2, Wnt 3, Wnt 4, Wnt 5a, Wnt 5b, Wnt 7a, Wnt 7b, Wnt 10a, Wnt 10b, or any combination thereof. In an embodiment which is not meant to be limiting in any manner, the wnt polypeptides comprise Wnts 5a, 5b, 7a, and 7b. In an alternate embodiment which is not meant to be limiting, the wnt polypeptides comprise Wnts 5a, 5b, 7b, 10a and 10b.

In an alternate embodiment of the present invention, the one or more activators of wnt signalling may comprise a small molecule, for example, but not limited to lithium chloride.

The present invention also contemplates a method as defined above wherein the one or more activators of wnt-signaling comprise one or more compounds that bind to and inhibit the activity of one or more soluble Frizzled-related proteins (sFRPs). The compounds may be one or more small molecules, polypeptides, proteins, macromolecules or a combination thereof. In an embodiment, the one or more polypeptides comprise one or more antibodies or antibody fragments that bind to sFRP 1, sFRP 2, sFRP 3, sFRP 4, or a combination thereof.

Also contemplated by the method as defined above, the modulating may inhibit proliferation, differentiation or both proliferation and differentiation of the stem cells, and the composition may comprise one or more inhibitors of wnt-signaling, for example, but not limited to one or more soluble Frizzled-related proteins (sFRPs), preferably one or more of sFRP1, sFRP2, sFRP3, sFRP4, or a combination thereof. In an embodiment of the present invention, which is not meant to be limiting in any manner, the one or more soluble Frizzled-related proteins may comprise sFRP2 and sFRP3. In a further embodiment, the soluble Frizzled-related proteins are human Frizzled-related proteins.

The subject described in the method of the present invention as defined above may be a mammalian subject, for example, but not limited to mouse, cow, sheep, goat, pig, dog, cat, rat, rabbit, primate, or human. In an embodiment, which is not meant to be limiting, the subject is a human.

The method as defined above also contemplates that the human subject exhibits or has muscle degeneration or muscle wasting. The muscle degeneration or muscle wasting may be caused in whole or in part by a disease, for example aids, cancer, a muscular degenerative disease, or a combination thereof. Examples of muscular degenerative diseases include, but are not limited to Duchenne muscular dystrophy (DMD), Becker muscular dystrophy (BMD), myotonic dystrophy (Steinert's disease), limb-girdle muscular dystrophies, facioscapulohumeral muscular dystrophy (FSH), congenital muscular dystrophies, oculopharyngeal muscular dystrophy (OPMD), distal muscular dystrophies or Emery-Dreifuss muscular dystrophy.

The present invention also contemplates a method as defined above wherein the subject exhibits or has skeletal muscle damage. The skeletal muscle damage may be disease related or non-disease related. For example, but not wishing to be limiting in any manner, the method may be employed to beat muscle wasting due to inactivity, for example, but not limited to after surgery or the like. Alternatively, the method of the present invention may be employed to increase the number of muscle cells in a subject, and/or it may be employed to increase the size, strength or muscle mass of one or more muscles in the subject.

Also contemplated by the method as defined above, the composition may further comprise a compound that enhances the survival of the stem cells, for example, but not limited to a sonic hedgehog (Shh) protein.

The present invention also provides a composition for use in modulating proliferation, differentiation or both proliferation and differentiation of stem cells in a subject comprising,
one or more activators or inhibitors of wnt-signaling in the subject, and;
a pharmaceutically acceptable carrier or diluent.

In a preferred embodiment, the composition is employed to promote proliferation, differentiation, or both proliferation and differentiation of-stem cells in the subject, and the one or more activators of wnt signaling comprise one or more wnt polypeptides, for example, but not limited to Wnt 1, Wnt 2, Wnt 3, Wnt 4, Wnt 5a, Wnt 5b, Wnt 7a, Wnt 7b, 10a, 10b or a combination thereof. In a specific embodiment, which is not meant to be limiting, the wnt polypeptides comprise Wnt 5a, Wnt 5b, Wnt 7a, and Wnt 7b. In an alternate embodiment, the wnt polypeptides comprise Wnt 5a, Wnt 5b, Wnt 7b, Wnt 10a and Wnt 10b. The present invention also contemplates methods and compositions that employ as wnt polypeptides, any combination of Wnt 5a, Wnt 5b, Wnt 7b, Wnt 10a and Wnt 10b.

The present invention also contemplates that the composition as defined above is employed to promote proliferation, differentiation, or both proliferation and differentiation of stem cells in the subject, and wherein the one or more activators of wnt signaling comprise one or more compounds that bind to and inhibit the activity of one or more soluble Frizzled-related proteins (sFRPs). The one or more compounds may comprise one or more small molecules, for example, but not limited to chemically synthesized molecules, or the one or more compounds may comprise one or more polypeptides, for example, but not limited to one or more antibodies or antibody fragments.

In an embodiment, the one or more compounds bind to and inhibit the soluble Frizzled-related proteins (sFRP) sFRP 1, sFRP 2, sFRP 3, sFRP-4, or a combination thereof. In an alternate embodiment, the one or more compounds bind to and inhibit the activity of soluble Frizzled-related proteins sFRP 2 and sFRP3. The sFRPs may be, but are not limited to human sFRPs, variants or derivates thereof that exhibit substantially the same activity as the wild-type sFRP.

The composition of the present invention as defined above may further comprise a compound that enhances survival of the stem cells, for example a sonic hedgehog protein. Also the composition may comprise one or more stem cells, for example, but not limited to CD45+:Sca1+ stem cells. The CD45+:Sca1+ stem cells may be neonatal, for example derived from a subject at any time after birth.

This summary of the invention does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein:

FIG. 8 depicts the experimental design and results of experiments demonstrating an increase in cells commited to myogenesis in response to lithium treatment in vivo.

DESCRIPTION OF PREFERRED EMBODIMENT

Figure 1:
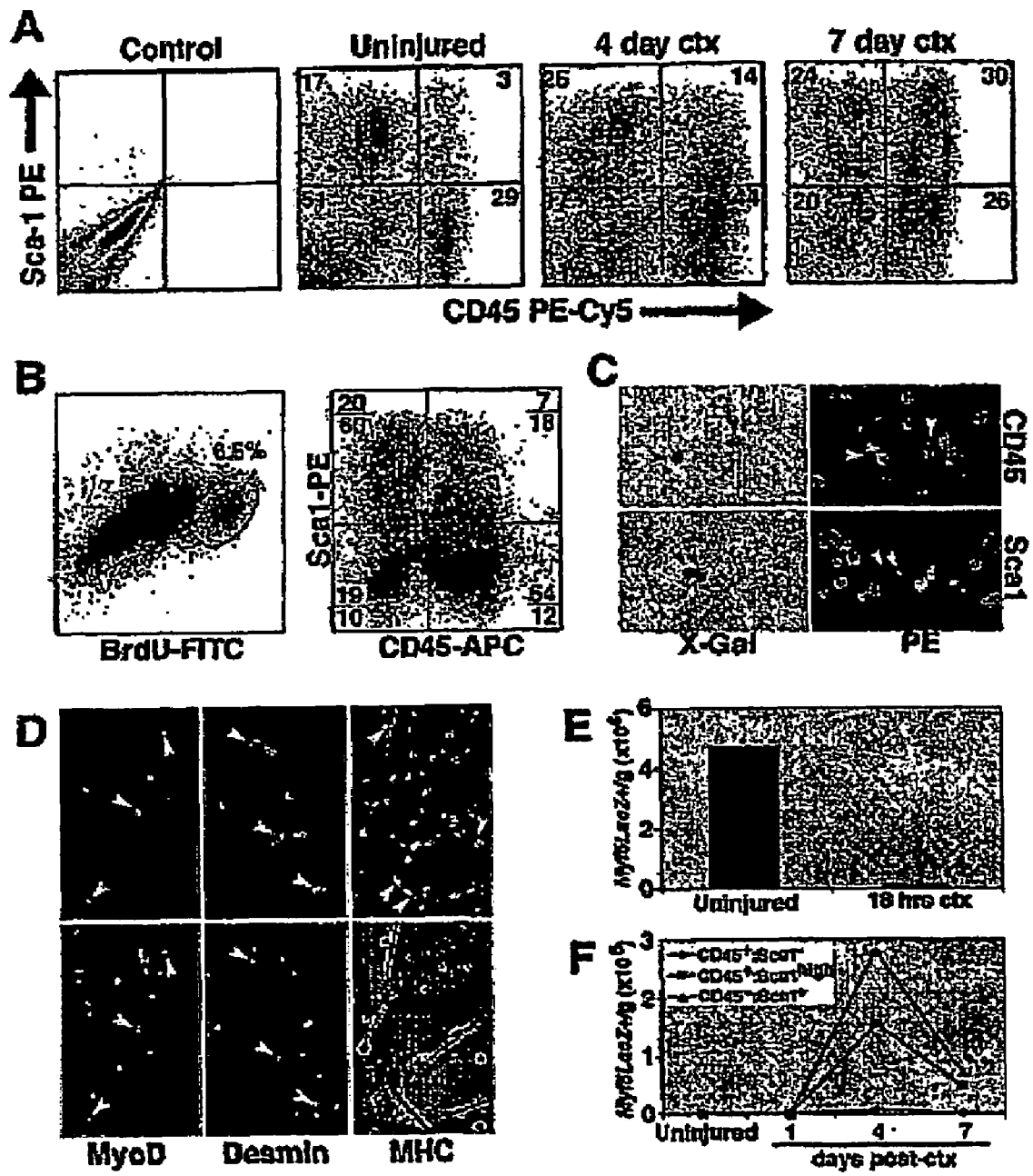
FIG. 1 depicts myogenic recruitment of CD45$^+$:Sca1$^+$ cells in regenerating muscle. (A) Flow cytometric analysis of skeletal muscle derived cells demonstrated that the proportion of cells expressing the hematopoietic markers CD45 and Sca1 increased dramatically in regenerating muscle (4 and 7 days after cardiotoxin (ctx) injection). The gating for CD45$^+$:Sca1$^{high}$ cells is shown for the 4 day time-point (B) In vivo cell proliferation experiments indicated that 60% and 18% of BrdU+ cells were CD45−:Sca-1$^+$ and CD45$^+$:Sca1$^+$ respectively at 4 days post-injury. (C) ~7-10% of CD45$^+$:Sca1$^{high}$ cells purified from regenerating but not uninjured Myf5nLacZ skeletal muscle co-expressed CD45, Sca1 and Myf5nLacZ as detected by X-Gal reaction. (D) Fractionated CD45$^+$:Sca1$^{high}$ cells gave rise to MyoD and Desmin expressing skeletal muscle cells in culture. Moreover, a similar proportion of CD45$^+$:Sca1$^{high}$ cells differentiated to Myosin Heavy Chain (MHC) expressing myotubes. (E) The number of Myf5nLacZ satellite cells was ~30 fold lower 18 hours after cardiotoxin injection compared to uninjured muscle. (F) Quantitative analysis indicated that the CD45$^+$:Sca1$^{high}$ and CD45−:Sca1$^+$ fractions gave rise to an average of 1.54×10$^5$ and 3.9×10$^5$ myogenic cells respectively, while the CD45$^+$:Sca1$^−$ fraction contained negligible myogenic activity.

The following description is of a preferred embodiment by way of example only and without limitation to the combination of features necessary for carrying the invention into effect.

The present invention provides methods of modulating proliferation and lineage commitment of adult stem cells by modulating the Wnt signalling pathways. The invention further provides for modulators of the Wnt signaling pathways and their use to induce or inhibit adult stem cell proliferation and/or lineage commitment. Modulators of the Wnt signaling pathways include both activators and inhibitors. A modulator can be used to inhibit the Wnt signaling pathways and thereby inhibit proliferation and/or prevent lineage commitment of stem cells. Alternatively, a modulator can be used to activate the Wnt signaling pathways and thereby induce proliferation and/or lineage commitment of stem cells. In accordance with one embodiment of the present invention, the lineage commitment of the stem cells that is induced or inhibited by the action of a modulator is commitment to the generation of myogenic progenitor cells. In addition, activation of the Wnt pathways can be used to increase the survival of adult stem cells and/or committed progenitor cells. Wnt modulation can be used to modulate terminal differentiation of committed progenitor cells.

The present invention thus provides methods of inhibiting or inducing proliferation and/or lineage commitment of adult stem cells comprising contacting the cells with one or more modulator of the Wnt pathways. The modulator may be in the form of a polypeptide, a peptide, a nucleic acid molecule, an antibody or antibody fragment, or a small organic or inorganic molecule, or the modulator may be in the form of a cell expressing a polypeptide, peptide, antibody or small molecule. The methods of the present invention may be conducted in vitro or in vivo, and are particularly useful for in vivo stimulation of proliferation and/or lineage commitment of resident stem cells in a tissue. The present invention further provides for methods of increasing the number of committed progenitor cells in a tissue comprising contacting the cells with one or more activators of the Wnt pathways, thus providing enhanced regeneration of the tissue and for methods of inducing terminal differentiation of committed progenitor cells comprising contacting the cells with one or more activators of the Wnt pathways.

Therapeutic applications of the present invention pertain to diseases and disorders in which there is a need to increase the number of resident stem cells or committed precursor cells, for example, to replace damaged or defective tissue, or to prevent muscle atrophy or loss of muscle mass, in particular in relation to diseases and disorders such as muscular dystrophy, neuromuscular and neurodegenerative diseases, cardiovascular disease, stroke, heart failure, myocardial infarction, cancer, HIV infection, AIDS, type II diabetes, and the like.

Definitions

Unless defined otherwise, all technical and scientific terms used herein have the same meaning as commonly understood by one of ordinary skill in the art to which this invention pertains.

The term "Wnt polypeptide," as used herein, encompasses Wnt proteins having a polypeptide sequence corresponding to the wild-type sequence as well as variant polypeptide sequences, polypeptide fragments and chimeric polypeptides having an activity of a wild-type Wnt-polypeptide. A number of Wnt proteins are known in the art, including the human Wnts: Wnt 1, Wnt 2, Wnt 3, Wnt 4, Wnt 5a, Wnt 5b, Wnt 7a and Wnt 7b, and the mouse Wnts: Wnt 1, Wnt 2, Wnt 3a, Wnt 3b, Wnt 4, Wnt 5a, Wnt 5b, Wnt 6, Wnt 7a, Wnt 7b, Wnt 8a, Wnt 8b, Wnt 10a, Wnt 10b, Wnt 11 and Wnt 12.

The term "Wnt signalling pathways," as used herein, refers to the cellular signalling pathways mediated by Wnt proteins that are involved in stem cell differentiation.

The term "modulator" as used herein refers to both activators and inhibitors of the Wnt signalling pathways. Thus a "modulator" of the Wnt signalling pathways is a compound or molecule that stimulates or inhibits the activity of a Wnt polypeptide either directly, by acting on the Wnt protein or gene, or indirectly, by acting on one or more proteins, or genes that encode proteins, that act upstream (activators) or downstream (effectors) of the Wnt protein in the signaling pathways.

The term "stem cell" as used herein refers to a cell that is capable of differentiating into a number of final, differentiated cell types. Stem cells may be totipotent or pluripotent cells. Totipotent stem cells typically have the capacity to develop into any cell type. Totipotent stem cells are usually embryonic in origin. Pluripotent cells are typically cells in a stem cell line capable of differentiating into several different, final differentiated cell types. Unipotent and pluripotent stem cells can originate from various tissue or organ systems, including, but not limited to, blood, nerve, muscle, skin, gut, bone, kidney, liver, pancreas, thymus, and the like. In accordance with the present invention, the stem cell is derived from an adult or neonatal tissue or organ.

The term "progenitor cell," as used herein, refers to a cell that is committed to a particular cell lineage and which gives rise to cells of this lineage by a series of cell divisions. An example of a progenitor cell would be a myoblast, which is capable of differentiation to only one type of cell, but is itself not fully mature or fully differentiated.

The terms "proliferation" and "expansion" as used interchangeably herein with reference to cells, refer to an increase in the number of cells of the same type by division.

The term "differentiation," as used herein, refers to a developmental process whereby cells become specialised for a particular function, for example, where cells acquire one or more morphological characteristics and/or functions different from that of the initial cell type. The term "differentiation" includes both lineage commitment and terminal differentiation processes. Differentiation may assessed, for example, by monitoring the presence or absence of lineage markers, using immunohistochemistry or other procedures known to a worker skilled in the art Differentiated progeny cells derived from progenitor cells may be, but are not necessarily, related to the same germ layer or tissue as the source tissue of the stem cells. For example, neural progenitor cells and muscle progenitor cells can differentiate into hematopoietic cell lineages.

The terms "lineage commitment" and "specification," as used interchangeably herein, refer to the process a stem cell undergoes in which the stem cell gives rise to a progenitor cell committed to forming a particular limited range of differentiated cell types, Committed progenitor cells are often capable of self-renewal or cell division.

The term "terminal differentiation," as used herein, refers to the final differentiation of a cell into a mature, fully differentiated cell. For example, neural progenitor cells and muscle progenitor cells can differentiate into hematopoietic cell lineages, terminal differentiation of which leads to mature blood cells of a specific cell type. Usually, terminal differentiation is associated with-withdrawal from the cell cycle and cessation of proliferation.

"Naturally occurring," as used herein in reference to an object, indicates that the object can be found in nature. For example, a naturally occurring polypeptide or polynucleotide sequence would be one that is present in an organism, and can be isolated from the organism and which has not been intentionally modified by man in the laboratory.

As used herein, the term "about" refers to a +/−5% variation from the nominal value. It is to be understood that such a variation is always included in any given value provided herein, whether or not it is specifically referred to.

Other chemistry terms employed herein are used according to conventional usage in the art, as exemplified by The McGraw-Hill Dictionary of Chemical Terms (ed. Parker, S., 1985), McGraw-Hill, San Francisco.

Candidate Modulators of the Wnt Signalling Pathways

In accordance with the present invention, candidate modulators of the Wnt signaling pathways are compounds and molecules that stimulate or inhibit the activity of a Wnt polypeptide, either directly or indirectly. Direct modulators act on a Wnt polypeptide, or a gene encoding a Wnt polypeptide, whereas indirect modulators act on one or more proteins that, or genes encoding proteins, that act upstream ("activators") or downstream ("effectors") of a Wnt polypeptide in the Wnt signalling pathways. Thus, a modulator can act at a genetic level, for example to upregulate or downregulate the expression of a gene encoding a Wnt polypeptide or an activator or effector of a Wnt polypeptide, or at the protein level to interfere with the activity of a Wnt polypeptide or an activator or effector protein of a Wnt polypeptide. Modulators that are themselves Wnt polypeptides, or active fragments or variants thereof, that can augment the level of the Wnt in the cell are also contemplated. A modulator can be, for example, a polypeptide, peptide, polynucleotide, oligonucleotide, antibody or antibody fragment, or a small molecule activator or inhibitor. Small molecule modulators can be organic or inorganic. In the context of the present invention, the activity of a Wnt polypeptide refers to the activity that leads to stem cell differentiation and/or proliferation.

In one embodiment of the present invention, the modulator acts at a genetic level to upregulate the expression of a gene encoding a Wnt polypeptide. In another embodiment, the modulator comprises a gene encoding a Wnt polypeptide that acts to increase the total amount of the Wnt in a cell and thus augment the activity of the Wnt in the signalling pathways. In another embodiment, the modulator acts at a protein level to enhance the activity of a Wnt polypeptide or to augment the level of a Wnt polypeptide in a cell. In a further embodiment, the modulator acts at a protein level to inhibit the activity of a Wnt polypeptide.

(i) Polypeptides and Peptides

The terms "polypeptide" and "peptide," as used herein, refer to a sequence of amino acid residues linked together by peptide bonds or modified peptide bonds. Typically, a polypeptide is at least six amino acids long and a peptide is at least 3 amino acids long. The polypeptide or peptide can be naturally occurring, recombinant, synthetic, or a combination of these. The polypeptide or peptide can be a fragment of a naturally occurring protein or polypeptide. The terms polypeptide and peptide also encompass peptide analogues, peptide derivatives and peptidomimetic compounds. Such compounds are well known in the art and may have significant advantages over naturally occurring peptides, including, for example, greater chemical stability, increased resistance to proteolytic degradation, enhanced pharmacological properties (such as, half-life, absorption, potency and efficacy), altered specificity (for example, a broad-spectrum of biological activities) and/or reduced antigenicity.

A "peptide derivative" is a peptide containing additional chemical or biochemical moieties not normally a part of a naturally occurring peptide. Peptide derivatives include peptides in which one or more amino acid side chain and/or the amino-terminus and/or the carboxy-terminus has been derivatised with a suitable chemical substituent group, as well as cyclic peptides, dual peptides, multimers of the peptides, peptides fused to other proteins or carriers, glycosylated peptides, phosphorylated peptides, peptides conjugated to lipophilic moieties (for example, caproyl, lauryl, stearoyl moieties) and peptides conjugated to an antibody or other biological ligand.

Examples of chemical substituent groups that may be used to derivatise a peptide include, but are not limited to, alkyl, cycloalkyl and aryl groups; acyl groups, including alkanoyl and aroyl groups; esters; amides; halogens; hydroxyls; carbamyls, and the like. The substituent group may also be a blocking group such as Fmoc (fluorenylmethyl-O—CO—), carbobenzoxy(benzyl—CO—), monomethoxysuccinyl naphthyl-NH—CO—, acetylamino-caproyl and adamantyl-NH—CO—. Other derivatives include C-terminal hydroxymethyl derivatives, O-modified derivatives (for example, C-terminal hydroxymethyl benzyl ether) and N-terminally modified derivatives including substituted amides such as alkylamides and hydrazides.

The-term "Cyclic peptide," as used herein, refers to a cyclic derivative of a peptide to which, for example, two or more additional amino acid residues suitable for cyclisation have been added. These additional amino acids may be added at the carboxyl terminus and at the amino terminus, or they may be at internal positions. Alternatively, a cyclic peptide may take advantage of cysteine residues that occur naturally in the amino acid sequence to form a disulphide bond and thereby cyclise the peptide. A cyclic peptide can contain either an intramolecular disulphide bond, i.e., —S—S—; an intramolecular amide bond between the two added residues, i.e., —CONH— or —NHCO—; or intramolecular S-alkyl bonds, i.e., —S—$CH_2$)—CONH— or —NH—CO$(CH_2)_a$—S—, wherein n is 1, 2, or more.

Cyclic peptides containing an intramolecular disulphide bond may be prepared by conventional solid phase synthesis while incorporating suitable S-protected cysteine or homocysteine residues at the positions selected for cyclisation (see, for example, Sahm et al., 1996, *J. Pharm. Pharmacol.* 48:197). Following completion of the chain assembly, cyclisation can be performed either-by selective removal of the S-protecting groups with a consequent on-support oxidation of free corresponding SH-functions, to form S—S bonds, followed by conventional removal of the product from the support and appropriate purification procedure, or by removal of the peptide from the support along with complete sidechain deprotection, followed by oxidation of the free SH-functions in highly dilute aqueous solution. Similarly, cyclic derivatives containing an intramolecular amide bond may be prepared by conventional solid phase synthesis while incorporating suitable amino and carboxyl sidechain protected amino acid derivatives at the positions selected for cyclisation, and cyclic peptides containing intramolecular —S-alkyl bonds can be prepared by conventional solid phase synthesis while incorporating an amino acid residue with a suitable amino-protected side chain, and a suitable S-protected cysteine or homocysteine residue at the positions selected for cyclisation.

A dual peptide consists of two of the same, or two different, peptides covalently linked to one another, either directly or through a spacer such as a short stretch of alanine residues or a putative site for proteolysis (see, for example, U.S. Pat. No. 5,126,249 and European Patent No. 495,049). Multimers are polymeric molecules formed from a number of the same or different peptides or derivatives thereof. The polymerisation is carried out with a suitable polymerisation agent, such as 0.1% glutaraldehyde (see, for example, Audibert et al., 1981, Nature 289:593).

A "peptide analogue" is a peptide comprising one or more non-naturally occurring amino acid. Examples of non-naturally occurring amino acids include, but are not limited to, D-amino acids (i.e. an amino acid of an opposite chirality to the naturally occurring form), N-α-methyl amino acids, C-α-methyl amino acids, (3-methyl amino acids, β-alanine (β-Ala), norvaline (eva), norleucine (Nle), 4-aminobutyric acid (γ-Abu), 2-aminoisobutyric acid (Aib), 6-aminohexanoic acid (ε-Ahx), ornithine (om), hydroxyproline (Hyp), sarcosine, citrulline, cysteic acid, cyclohexylalanine, α-amino isobutyric acid, t-butylglycine, t-butylalanine, 3-aminopropionic acid, 2,3-diaminopropionic acid (2,3-diaP),D- or L-phenylglycine, D- or L-2-naphthylalanine (2-Nal), 1,2,3,4-tetrahydroisoquinoline-3-carboxylic acid (Tic), D- or L-2-thienylalanine (Thi), D- or L-3-thienylalanine, D- or L-1-, 2-, 3- or 4 pyrenylalanine, D- or L-(2-pyridinyl)-alanine, D- or L-(3-pyridinyl)-alanine, D- or L-(2-pyrazinyl)-alamine, D- or L-4-(isopropyl)-phenylglycine, D-trifluoromethyl)-phenylglycine, D-(trifluoromethyl)-phenylalanine, D-p-fluorophenylalanine, D- or L-p-biphenylalanine D- or L-p-methoxybiphenylalanine, methionine sulphoxide (MSO) and homoarginine (Har). Other examples include D- or L-2-indole(alkyl)alanines and D- or L-alkylalanines, wherein alkyl is substituted or unsubstituted methyl ethyl, propyl hexyl, butyl, pentyl, isopropyl, iso-butyl, or iso-pentyl, and phosphono- or sulfated (e.g. —$SO_3H$) non-carboxylate amino acids.

As is known in the art, substitution of all D-amino acids for all L-amino acids within a peptide can result in an "inverso" peptide, or in a "retro-inverso" peptide (see Goodman et al. "Perspectives in Peptide Chemistry" pp. 283-294 (1981); U.S. Pat. No. 4,522,752), both of which are considered to be analogues in the context of the present invention. An "inverso" peptide is one in which all L-amino acids of a sequence have been replaced with D-amino acids, and a "retro-inverso" peptide is one in which the sequence of the amino acids has been reversed ("retro") and all L-amino acids have been replaced with D-amino acids. For example, if the parent peptide is Thr-Ala-Tyr, the retro form is Tyr-Ala-Thr, the inverso form is thr-ala-tyr, and the retro-inverso form is tyr-ala-thr Gower case letters indicate D-amino acids). Compared to the-parent peptide, a retro-inverso peptide has a reversed backbone while retaining substantially the original spatial conformation of the side chains, resulting in an isomer with a topology that closely resembles the parent peptide.

Peptidomimetics are compounds that are structurally similar to peptides and contain chemical moieties that mimic the function of the polypeptide or peptide of the invention. For example, if a polypeptide contains two charged chemical moieties having functional activity, a mimetic places two charged chemical moieties in a spatial orientation and constrained structure so that the charged chemical function is maintained in three-dimensional space. The term peptidomimetic thus is intended to include isosteres. The term "isostere," as used herein, refers to a chemical structure that can be substituted for a polypeptide or peptide because the steric conformation of the chemical structure is similar to that of the peptide or polypeptide, for example, the structure fits a binding site specific for the polypeptide or peptide. Examples of peptidomimetics include peptides comprising one or more backbone modifications (i.e., amide bond mimetics), which are well known in the art. Examples of amide bond mimetics include, but are not limited to, —$CH_2NH$—, —$CH_2S$—, —$CH_2CH_2$—, —CH=CH— (cis and trans), —$COCH_2$—, —CH(OH)$CH_2$—, and —$CH_2SO$— (see, for example, Spatola, Vega Data Vol. 1, Issue 3, (1983); Spatola, in *Chemistry and Biochemistry of Amino Acids Peptides and Proteins*, Weinstein, ed, Marcel Dekker, New York, p. 267 (1983); Morley, J. S., *Trends Pha Sci*. pp. 463-468 (1980); Hudson et al., *Int. J. Pept. Prot. Res.* 14:177-185 (1979); Spatola et al.,

*Life Sci.* 38:1243-1249 (1986); Hann, *J. Chem. Soc. Perkin Trans.* 1307-314 (1982); Almquist et al., *J. Med. Chem.* 23:1392-1398 (1980); Jennings-White et al. *Tetrahedron Lett.* 23:2533 (1982); Szelke et al., EP 45665 (1982); Holladay et al., *Tetrahedron Lett.* 24:4401-4404 (1983); and Hruby, *Life Sci* 31:189-199 (1982)). Other examples of peptidomimetics include peptides substituted with one or more benzodiazepine molecules (see, for example, James, G. L. et al. (1993) *Science* 260:1937-1942) and peptides comprising backbones crosslinked to form lactams or other cyclic structures.

One skilled in the art will appreciate that not all amino acids in a peptide or polypeptide need be modified. Similarly not all amino acids need be modified in the same way. Peptide derivatives, analogues and peptidomimetics of the present invention thus include chimeric molecules which contain two or more chemically distinct regions, each region comprising at least one amino acid or modified version thereof.

Polypeptide and peptide activators of the Wnt signalling pathways include those corresponding to Wnt proteins, for example, human Wnt 1, Wnt 2, Wnt 3, Wnt 4, Wnt 5a, Wnt 5b, Wnt 7a and Wnt 7b, and mouse Wnt 1, Wnt 2, Wnt 3a, Wnt 3b, Wnt 4, Wnt 5a, Wnt 5b, Wnt 6, Wnt 7a, Wnt 7b, Wnt 8a, Wnt 8b, Wnt 10a, Wnt 10b, Wnt 11 and Wnt 12, or active fragments or variants thereof. Also included are polypeptides corresponding to activator and effector proteins of Wnt proteins, for example, Disheveled (Dvl); β-catenin; Fzd 1, 2, 3, or 4; Tcf/LEF and Axin, or active fragments or variants thereof. Other signalling pathways are known to impact the Wnt signalling pathways, for example, cadherin mediated pathways. Cadherin can thus be considered to be an effector of the Wnt pathways. Polypeptide and peptide activators of the Wnt signalling pathways also encompass those that inhibit the activity of proteins which inhibit or downregulate the Wnt signalling pathways, for example, glycogen synthase kinase-3α and 3β (GSK-3α and 3β).

In one embodiment of the present invention, the activator is a Wnt protein, or an active fragment or variant thereof. In another embodiment, the activator is a human Wnt 5a, 5b, 7a or 7b protein, or an active fragment or variant thereof. In an alternate embodiment, which is not meant to be limiting in any manner, the activator is a human Wnt 5a, 5b, 7b, 10a, 10b protein, or an active fragment or variant thereof. Further the activator may comprise a combination of wnt proteins.

Active fragments are fragments of the naturally occurring (or wild-type) protein that retain substantially the same activity as the wild-type protein. Candidate fragments can be selected from random fragments generated from the wild-type protein or can be specifically designed. The activity of the fragments is tested and compared to that of the wild-type protein and those fragments with substantially the same activity as the wild-type protein are selected. Methods for generating polypeptide fragments are well known in the art and include enzymatic, chemical or mechanical cleavage of the wild-type protein or a recombinant version thereof expression of nucleic acids encoding such fragments, chemical synthesis and the like.

A variant protein, polypeptide or fragment is one in which one or more ammo acid residues have been deleted, added or substituted for those that appear in the amino acid sequence of the wild-type protein. In the context of the present invention, a variant also retains substantially the same activity as the wild-type protein. Typically, when a variant contains one or more amino acid substitutions they are "conservative" substitutions. A conservative substitution involves the replacement of one amino acid residue by another residue having similar side chain properties. As is known in the art, the twenty naturally occurring amino acids can be grouped according to the physicochemical properties of their side chains. Suitable groupings include alanine, valine, leucine, isoleucine, proline, methionine, phenylalanine and tryptophan (hydrophobic side chains); glycine, serine, threonine, cysteine, tyrosine, asparagine, and glutamine (polar, uncharged side chains); aspartic acid and glutamic acid (acidic side chains) and lysine, arginine and histidine (basic side chains). Another grouping of amino acids is phenylalanine, tryptophan, and tyrosine (aromatic side chains). A conservative substitution involves the substitution of an amino acid with another amino acid from the same group.

In the context of the present invention, a fragment or a variant is considered to have substantially the same activity as the wild-type protein when it exhibits about 50% of the activity of the wild-type protein. In one embodiment, the variant protein or fragment exhibits about 60% of the activity of the wild-type protein. In another embodiment, the variant protein or fragment exhibits about 75% of the activity of the wild-type protein. In still another embodiment, the variant protein or fragment exhibits about 90% of the activity of the wild-type protein.

Other polypeptide activators contemplated by the present invention include polypeptides or peptides that bind to and inhibit a protein that normally inhibits the activity of a Wnt polypeptide. An example of such a protein would be a member of the soluble Frizzled-related protein (sFRP) family. Several members of this family are known to exist in humans, for example, sFRP 1, sFRP 2, sFRP 3 and sFRP 4.

In one embodiment of the present invention, the modulator is a peptide derivative, analogue or peptidomimetic that binds to a sFRP and thus interferes with the binding of a Wnt polypeptide to the sFRP. In another embodiment, the modulator is a peptide derivative, analogue or peptidomimetic that binds to sFRP 2 or sFRP 3. Methods of identifying polypeptides or peptides that bind to and inhibit a target protein are known in the art. One exemplary method of identifying such peptides is by phage display techniques. Phage display libraries of random short peptides are commercially available, e.g. from New England Biolabs, Inc., and are utilised through an in vitro selection process known as "panning". In its simplest form, panning involves first incubating the library of phage-displayed peptides with a plate, or bead, coated with the target molecule, then washing away unbound phage particles, and finally eluting the specifically bound phage. The peptide(s) displayed by the specifically-binding phage are then isolated and sequenced by standard techniques. In some instances the binding strength of the isolated peptide can also be tested using standard techniques.

Protein, polypeptide and peptide inhibitors contemplated by the present invention include proteins that naturally inhibit a Wnt polypeptide in the Wnt signalling pathways, and active fragments and variants thereof. Examples of such proteins include members of the sFRP family indicated above, and GSK-3α (and 3β). Other examples of inhibitors include peptide derivatives, analogues or peptidomimetics that bind to a Wnt Frizzled receptor and thereby prevent binding of Wnt and subsequent activation of proteins downstream in the signalling pathways. The polypeptide and peptide inhibitors of the present invention also encompass those that inhibit the activity of an effector of the Wnt pathways, for example, Dvl, β-catenin, Tcf and Axin.

The present invention also contemplates the use of a biologically inactive proteins or fragments of proteins that interfere with the action of the wild-type protein and thus, act as inhibitors of protein activity. Examples include dominant negative mutants. Biologically inactive proteins or fragments contemplated by the present invention are those that have substantially less activity than the wild-type protein. Candidate inhibitory fragments can be selected from random fragments generated from the wild-type protein. Methods for generating the candidate polypeptide fragments are well known to workers skilled in the art and include those described above. Biologically inactive proteins can also be generated, for example, by site-directed or random mutagenesis techniques of nucleic acids encoding the protein, or by inactivation of the protein by chemical or physical means.

In the context of the present invention, a biologically inactive protein, fragment or variant is considered to have substantially less activity than the wild-type protein when it exhibits about 75% or less of the activity of the wild-type protein. In another embodiment, the variant protein or fragment exhibits about 60% or less of the activity of the wild-type protein. In a further embodiment, the biologically inactive variant protein or fragment exhibits about 50% or less of the activity of the wild-type protein, for example, between about 1% and about 40% of the activity of the wild-type protein.

The polypeptides and peptides of the present invention can be prepared by methods known in the art, such as purification from cell extracts or the use of recombinant techniques. The amino acid sequences of a large number of Wnt polypeptides and other proteins involved in the Wnt signalling pathways are known in the art. Representative GenBanK Accession Nos for known proteins in the Wnt signalling pathways are provided in Table 1. Polypeptides derived from one of these sequences, or fragments thereof, can also be chemically synthesised by methods known in the art including, but not limited to, exclusive solid phase synthesis, partial solid phase synthesis, fragment condensation or classical solution synthesis (Merrifield (1963) *J. Am. Chem. Soc.* 85:2149; Merrifield (1986) *Science* 232:341). The polypeptides and peptides can be purified using standard techniques such as chromatography (e.g. ion exchange, affinity, and sizing column chromatography or high performance liquid chromatography), centrifugation, differential solubility, or by other techniques familiar to a worker skilled in the art. A purification protocol for Wnt proteins has been reported Willert, et al., (2003) *Nature*, 423:448-452). In addition certain proteins in the Wnt pathways are available commercially, for example, sFRP 2 and sFRP 3 (&D Systems).

TABLE 1

Representative GenBank Accession Numbers for Proteins in the Wnt Signalling Pathways

| Accession No. | Protein Identification | Descriptive Information |
| --- | --- | --- |
| *Wnt Protein Sequences* | | |
| Q93097 | Wnt-2b protein precursor (Wnt-13) | gi\|14424481\|sp\|Q93097\|WN2B__HUMAN[14424481] |
| O70283 | Wnt-2b protein precursor (Wnt-13) | gi\|6175249\|sp\|O70283\|WN2B__MOUSE[6175249] |
| P56705 | Wnt-4 protein precursor | gi\|20532425\|sp\|P56705\|WNT4__HUMAN[20532425] |
| P56704 | Wnt-3a protein precursor | gi\|20532424\|sp\|P56704\|WN3A__HUMAN[20532424] |
| P22724 | Wnt-4 protein precursor | gi\|139761\|sp\|P22724\|WNT4__MOUSE[139761] |
| C36470 | Wnt-4 protein - mouse | gi\|111251\|pir\|\|C36470[111251] |
| P41221 | Wnt-5a protein precursor | gi\|731157\|sp\|P41221\|WN5A__HUMAN[731157] |
| P22725 | Wnt-5a protein precursor | gi\|139721\|sp\|P22725\|WN5A__MOUSE[139721] |
| D36470 | Wnt-5a protein - mouse | gi\|111252\|pir\|\|D36470[111252] |
| P22726 | Wnt-5b protein precursor | gi\|14424475\|sp\|P22726\|WN5B__MOUSE[14424475] |
| Q9H1J7 | Wnt-5b protein precursor | gi\|20532427\|sp\|Q9H1J7\|WN5B__HUMAN[20532427] |
| E36470 | Wnt-5b protein - mouse | gi\|111253\|pir\|\|E36470[111253] |
| NP_033553 | wingless-related MMTV integration site 7A; postaxial hemimelia [*Mus musculus*] | gi\|31543960\|ref\|NP_033553.2\|[31543960] |
| O00755 | Wnt-7a protein precursor | gi\|2501663\|sp\|O00755\|WN7A__HUMAN[2501663] |
| P24383 | Wnt-7a protein precursor | gi\|139731\|sp\|P24383\|WN7A__MOUSE[139731] |
| NP_004616 | wingless-type MMTV integration site family, member 7A precursor; proto-oncogene Wnt7a protein [*Homo sapiens*] | gi\|17505191\|ref\|NP_004616.2\|[17505191] |
| G36470 | Wnt-7a protein - mouse | gi\|111255\|pir\|\|G36470[111255] |
| P56706 | Wnt-7b protein precursor | gi\|20532426\|sp\|P56706\|WN7B__HUMAN[20532426] |
| P28047 | Wnt-7b protein precursor | gi\|139736\|sp\|P28047\|WN7B__MOUSE[139736] |
| H36470 | Wnt-7b protein - mouse | gi\|111256\|pir\|\|H36470[111256] |
| *Frizzled Protein Sequences* | | |
| NP_032081 | Frizzled 4 [*Mus musculus*] | gi\|3156070\|ref\|NP_032081.2\|[31560701] |
| Q9UP38 | Frizzled 1 precursor (Frizzled-1) (Fz-1) (hFz1) (FzE1) | gi\|17433092\|sp\|Q9UP38\|FZD1__HUMAN[17433092] |

TABLE 1-continued

Representative GenBank Accession Numbers for Proteins in the Wnt Signalling Pathways

| Accession No. | Protein Identification | Descriptive Information |
|---|---|---|
| Q9ULV1 | Frizzled 4 precursor (Frizzled-4) (Fz-4) (hFz4) (FzE4) | gi\|17433090\|sp\|Q9ULV1\|FZD4_HUMAN[17433090] |
| Q14332 | Frizzled 2 precursor (Frizzled-2) (Fz-2) (hFz2) (FzE2) | gi\|17433019\|sp\|Q14332\|FZD2_HUMAN[17433019] |
| NP_003459 | Frizzled 5; Wnt receptor [*Homo sapiens*] | gi\|27894385\|ref\|NP_003459.2\|[27894385] |
| NP_036325 | Frizzled 4; WNT receptor frizzled-4 [*Homo sapiens*] | gi\|22547161\|ref\|NP_036325.2\|[22547161] |
| Q9NPG1 | Frizzled 3 precursor (Frizzled-3) (Fz-3) (hFz3) | gi\|17433071\|sp\|Q9NPG1\|FZD3_HUMAN[17433071] |
| Q9JIP6 | Frizzled 2 precursor (Frizzled-2) (Fz-2) (mFz2) (mFz10) | gi\|17433064\|sp\|Q9JP6\|FZD2_MOUSE[17433064] |
| Q61088 | Frizzled 4 precursor (Frizzled-4) (Fz-4) (mFz4) | gi\|17433026\|sp\|Q61088\|FZD4_MOUSE[17433026] |
| Q61086 | Frizzled 3 precursor (Frizzled-3) (Fz-3) (mFz3) | gi\|17433025\|sp\|Q61086\|FZD3_MOUSE[17433025] |
| O70421 | Frizzled 1 precursor (Frizzled-1) (Fz-1) (mFz1) | gi\|17432987\|sp\|O70421\|FZD1_MOUSE[17432987] |
| NP_003496 | Frizzled 1; Frizzled, *drosophila*, homolog, of, 1; Wnt receptor [*Homo sapiens*] | gi\|4503825\|ref\|NP_003496.1\|[4503825] |
| NP_067433 | Frizzled homolog 3 [*Mus musculus*] | gi\|10946846\|ref\|NP_067433.1\|[10946846] |
| NP_067432 | Frizzled homolog 1; frizzled homolog 1, (*Drosophila*) [*Mus musculus*] | gi\|10946844\|ref\|NP_067432.1\|[10946844] |
| NP_065256 | Frizzled homolog 2 [*Mus musculus*] | gi\|10048406\|ref\|NP_065256.1\|[10048406] |
| NP_059108 | Frizzled 3 [*Homo sapiens*] | gi\|8393378\|ref\|NP_059108.1\|[8393378] |
| NP_001457 | Frizzled 2 [*Homo sapiens*] | gi\|4503827\|ref\|NP_001457.1\|[4503827] |
| AAH49774 | Frizzled homolog 2 (*Drosophila*) [*Mus musculus*] | gi\|29436746\|gb\|AAH49774.1\|[29436746] |
| JC7312 | Frizzled-3 protein - human | gi\|11359869\|pir\|\|JC7312[11359869] |
| JC7127 | Frizzled protein 4 - human | gi\|7522622\|pir\|\|JC7127[7522622] |
| JE0174 | Frizzled protein-2 - human | gi\|7512442\|pir\|\|JE0174[7512442] |
| JE0337 | Frizzled-1 protein - human | gi\|7451366\|pir\|\|JE0337[7451366] |
| JE0338 | Frizzled-2 protein - human | gi\|7451364\|pir\|\|JE0338[7451364] |
| AAH15256 | Frizzled homolog 4 (*Drosophila*) [*Mus musculus*] | gi\|15929645\|gb\|AAH15256.1\|[15929645] |
| AAH25750 | Frizzled homolog 4 (*Drosophila*) [*Homo sapiens*] | gi\|19343596\|gb\|AAH25750.1\|[19343596] |
| AAK77487 | Frizzled 2 [*Mus musculus*] | gi\|15011288\|gb\|AAK77487.1\|AF363723_1[15011288] |
| AAF89088 | frizzled-3 [*Homo sapiens*] | gi\|9664928\|gb\|AAF89088.1\|[9664928] |
| AAD41636 | frizzled 1 [*Homo sapiens*] | gi\|5305407\|gb\|AAD41636.1\|AF072872_1[5305407] |
| BAA86286 | WNT receptor Frizzled-4 [*Homo sapiens*] | gi\|6277266\|dbj\|BAA86286.1\|[6277266] |
| AAD28286 | Frizzled-2 protein [*Mus musculus*] | gi\|4704822\|gb\|AAD28286.1\|AF139183_1[4704822] |
| BAA34667 | frizzled-2 [*Homo sapiens*] | gi\|3927885\|dbj\|BAA34667.1\|[3927885] |
| BAA34666 | frizzled-1 [*Homo sapiens*] | gi\|3927883\|dbj\|BAA34666.1\|[3927883] |
| AAC01952 | Frizzled 1 [*Mus musculus*] | gi\|2222885\|gb\|AAC01952.1\|[2222885] |
| Secreted/Soluble Frizzled-Related Protein Sequences | | |
| P97401 | Frizzled-related protein precursor (Frzb-1) (Frezzled) (Fritz) (Secreted frizzled-related sequence protein 3) (sFRP-3) | gi\|14194747\|sp\|P97401\|FRZB_MOUSE[14194747] |
| Q92765 | Frizzled-related protein precursor (Frzb-1) (Frezzled) (Fritz) | gi\|14194748\|sp\|Q92765\|FRZB_HUMAN[14194748] |
| NP_003005 | Secreted frizzled-related protein 4 [*Homo sapiens*] | gi\|4506895\|ref\|NP_003005.1\|[4506895] |
| AAH34853 | Secreted frizzled-related sequence protein 4 [*Mus musculus*] | gi\|22028398\|gb\|AAH34853.1\|[22028398] |
| AAH14722 | Secreted frizzled-related sequence protein 2 [*Mus musculus*] | gi\|15928488\|gb\|AAH14722.1\|[15928488] |
| NP_057896 | Secreted frizzled-related sequence protein 4 [*Mus musculus*] | gi\|7710094\|ref\|NP_057896.1\|[7710094] |
| NP_038862 | Secreted frizzled-related sequence protein 1 [*Mus musculus*] | gi\|7305481\|ref\|NP_038862.1\|[7305481] |
| NP_035486 | frizzled-related protein; secreted frizzled-related sequence protein 3 [*Mus musculus*] | gi\|6755476\|ref\|NP_035486.1\|[6755476] |

TABLE 1-continued

Representative GenBank Accession Numbers for Proteins in the Wnt Signalling Pathways

| Accession No. | Protein Identification | Descriptive Information |
|---|---|---|
| NP_033170 | Secreted frizzled-related sequence protein 2; stromal cell derived factor 5; secreted frizzled-related sequence protein 5 [*Mus musculus*] | gi\|6677895\|ref\|NP_033170.1\|[6677895] |
| NP_003006 | Secreted frizzled-related protein 5; secreted apoptosis related protein 3 [*Homo sapiens*] | gi\|4506897\|ref\|NP_003006.1\|[4506897] |
| AAL14904 | frizzled-related protein 4 [*Mus musculus*] | gi\|16151905\|gb\|AAL14904.1\|AF364906_1[16151905] |
| AAC53147 | Secreted frizzled related protein sFRP-3 [*Mus musculus*] | gi\|1946345\|gb\|AAC53147.1\|[1946345] |
| AAC53146 | Secreted frizzled related protein sFRP-2 [*Mus musculus*] | gi\|1946343\|gb\|AAC53146.1\|[1946343] |
| AAC53145 | Secreted frizzled related protein sFRP-1 [*Mus musculus*] | gi\|1946341\|gb\|AAC53145.1\|[1946341] |
| NP_036325 | frizzled 4; WNT receptor frizzled-4 [*Homo sapiens*] | gi\|22547161\|ref\|NP_036325.2\|[22547161] |
| NP_003003 | Secreted frizzled-related protein 1; secreted apoptosis-related protein 2 [*Homo sapiens*] | gi\|8400732\|ref\|NP_003003.2\|[8400732] |
| | Dishevelled Protein Sequences | |
| AAH53050 | Dishevelled 2, dsh homolog [*Mus musculus*] | gi\|31419842\|gb\|AAH53050.1\|[31419842] |
| Q92997 | Segment polarity protein dishevelled homolog DVL-3 (Dishevelled-3) (DSH homolog 3) | gi\|6919875\|sp\|Q92997\|DVL3_HUMAN[6919875] |
| P51141 | Segment polarity protein dishevelled homolog DVL-1 (Dishevelled-1) (DSH homolog 1) | gi\|1706529\|sp\|P51141\|DVL1_MOUSE[1706529] |
| NP_004412 | dishevelled 1; dishevelled 1 (homologous to *Drosophila* dsh) [*Homo sapiens*] | gi\|4758214\|ref\|NP_004412.1\|[4758214] |
| NP_004414 | dishevelled 3; dishevelled 3 (homologous to *Drosophila* dsh) [*Homo sapiens*] | gi\|6806887\|ref\|NP_004414.2\|[6806887] |
| NP_034221 | dishevelled, dsh homolog 1; dishevelled, dsh homolog (*Drosophila*) [*Mus musculus*] | gi\|6753696\|ref\|NP_034221.1\|[6753696] |
| NP_031915 | dishevelled 3, dsh homolog [*Mus musculus*] | gi\|6681241\|ref\|NP_031915.1\|[6681241] |
| NP_031914 | dishevelled 2, dsh homolog [*Mus musculus*] | gi\|6681239\|ref\|NP_031914.1\|[6681239] |
| NP_004413 | dishevelled 2; dishevelled 2 (homologous to *Drosophila* dsh) [*Homo sapiens*] | gi\|4758216\|ref\|NP_004413.1\|[4758216] |
| JC5763 | dishevelled protein 3 - human | gi\|7512391\|pir\|\|JC5763[7512391] |
| AAH32459 | dishevelled, dsh homolog 3 (*Drosophila*) [*Homo sapiens*] | gi\|21595561\|gb\|AAH32459.1\|[21595561] |
| XP_147262 | dishevelled 3, dsh homolog [*Mus musculus*] | gi\|20892043\|ref\|XP_147262.1\|[20892043] |
| AAH14844 | dishevelled 2 (homologous to *Drosophila* dsh) [*Homo sapiens*] | gi\|15928771\|gb\|AAH14844.1\|AAH14844[15928771] |
| AAB65244 | dishevelled 3 [*Homo sapiens*] | gi\|2291010\|gb\|AAB65244.1\|[2291010] |
| AAB65243 | dishevelled 2 [*Homo sapiens*] | gi\|2291008\|gb\|AAB65243.1\|[2291008] |
| AAB65242 | dishevelled 1 [*Homo sapiens*] | gi\|2291006\|gb\|AAB65242.1\|[2291006] |
| AAB84228 | dishevelled 3 [*Homo sapiens*] | gi\|2612833\|gb\|AAB84228.1\|[2612833] |
| | Glycogen Synthase Kinase-3 Beta Protein Sequences | |
| P49841 | Glycogen synthase kinase-3 beta (GSK-3 beta) | gi\|20455502\|sp\|P49841\|KG3B_HUMAN[20455502] |
| NP_002084 | Glycogen synthase kinase 3 beta [*Homo sapiens*] | gi\|21361340\|ref\|NP_002084.2\|[21361340] |
| NP_062801 | Glycogen synthase kinase 3 beta [*Mus musculus*] | gi\|9790077\|ref\|NP_062801.1\|[9790077] |
| AAD48517 | Glycogen synthase kinase 3 beta [*Homo sapiens*] | gi\|5730335\|gb\|AAD48517.1\|[5730335] |
| | Beta-Catenin Protein Sequences | |
| NP_031640 | catenin beta; cadherin associated protein; beta-catenin [*Mus musculus*] | gi\|6671684\|ref\|NP_031640.1\|[6671684] |

TABLE 1-continued

Representative GenBank Accession Numbers for Proteins in the Wnt Signalling Pathways

| Accession No. | Protein Identification | Descriptive Information |
|---|---|---|
| P35222 | Beta-catenin (PRO2286) | gi\|461854\|sp\|P35222\|CTNB_HUMAN[461854] |
| Q02248 | Beta-catenin | gi\|399310\|sp\|Q02248\|CTNB_MOUSE[399310] |
| NP_001895 | catenin (cadherin-associated protein), beta 1, 88 kDa; catenin (cadherin-associated protein), beta 1 (88 kD); catenin (cadherin-associated protein), beta 1 (88 kDa [*Homo sapiens*] | gi\|4503131\|ref\|NP_001895.1\|[4503131] |

Nucleic Acid Sequences

In one embodiment of the present invention, the polypeptides and peptides are produced by recombinant techniques. Typically, this involves transformation (including transfection, transduction, or infection) of a suitable host cell with an expression vector comprising all or part of a DNA encoding the polypeptide or peptide. The gene sequences for many of the proteins involved in the Wnt signaling pathways are known in the art. Representative GenBank Accession Nos for genes encoding known proteins in the Wnt signaling pathways are provided in Table 2.

TABLE 2

Representative GenBank Accession Numbers for Genes Encoding Proteins in the Wnt Signalling Pathways

| Accession No. | Nucleotide Identification | Descriptive Information |
|---|---|---|
| *Wnt Nucleotide Sequences* | | |
| NM_003392 | *Homo sapiens* wingless-type MMTV integration site family, member 5A (WNT5A), mRNA | gi\|17402917\|ref\|NM_003392.2\|[17402917] |
| NM_009524 | *Mus musculus* wingless-related MMTV integration site 5A (Wnt5a), mRNA | gi\|6678596\|ref\|NM_009524.1\|[6678596] |
| AK031512 | *Mus musculus* 13 days embryo male testis cDNA, RIKEN fall-length enriched library, clone: 6030445L03 product: WNT-5A PROTEIN PRECURSOR, full insert sequence | gi\|26327372\|dbj\|AK031512.1\|[26327372] |
| AK078764 | *Mus musculus* 15 days embryo male testis cDNA, RIKEN full-length enriched library, clone: 8030457G12 product WNT-5A PROTEIN PRECURSOR, full insert sequence | gi\|26098096\|dbj\|AK078764.1\|[26098096] |
| AK032977 | *Mus musculus* 12 days embryo male wolffian duct includes surrounding region cDNA, RIKEN full-length enriched library, clone: 6720483L10 product WNT-5A PROTEIN | gi\|26083139\|dbj\|AK032977.1\|[26083139] |
| U39837 | Human Wnt-5A gene, promoter region | gi\|1314288\|gb\|U39837.1\|HSU39837[1314288] |
| M89798 | Mouse Wnt-5a mRNA, complete cds | gi\|202403\|gb\|M89798.1\|MUSWNTVA[202403] |
| L20861 | *Homo sapiens* proto-oncogene (Wnt-5a) mRNA, complete cds | gi\|348917\|gb\|L20861.1\|HUMWNT5A[348917] |
| NM_009525 | *Mus musculus* wingless-related MMTV integration site 5B (Wnt5b), mRNA | gi\|31560626\|ref\|NM_009525.2\|[31560626] |
| NM_032642 | *Homo sapiens* wingless-type MMTV integration site family, member 5B (WNT5B), transcript variant 1, mRNA | gi\|17402920\|ref\|NM_032642.2\|[17402920] |

TABLE 2-continued

Representative GenBank Accession Numbers for
Genes Encoding Proteins in the Wnt Signalling Pathways

| Accession No. | Nucleotide Identification | Descriptive Information |
|---|---|---|
| NM_030775 | *Homo sapiens* wingless-type MMTV integration site family, member 5B (WNT5B), transcript variant 2, mRNA | gi|17402918|ref|NM_030775.2|[17402918] |
| AI894033 | mg77a09.y1 Soares mouse embryo NbME13.5 14.5 *Mus musculus* cDNA clone IMAGE: 439000 5' similar to gb: M89799 Mouse Wnt-5b mRNA, complete cds (MOUSE);, | gi|5599935|gb|AI894033.1|[5599935] |
| AI686324 | tt93e10.x1 NCI_CGAP_Pr28 *Homo sapiens* cDNA clone IMAGE: 2249130 3' similar to SW: WN5B_MOUSE P22726 WNT-5B PROTEIN PRECURSOR;, mRNA sequence | gi|4897618|gb|AI686324.1|[4897618] |
| M89799 | Mouse Wnt-5b mRNA, complete cds | gi|202405|gb|M89799.1|MUSWNTVB[202405] |
| NM_009527 | *Mus musculus* wingless-related MMTV integration site 7A (Wnt7a), mRNA | gi|31543959|ref|NM_009527.2|[31543959] |
| NM_004625 | *Homo sapiens* wingless-type MMTV integration site family, member 7A (WNT7A), mRNA | gi|17505190|ref|NM_004625.2|[17505190] |
| M89801 | Mouse Wnt-7a mRNA, complete cds | gi|202409|gb|M89801.1|MUSWNTVIIA[202409] |
| NM_058238 | *Homo sapiens* wingless-type MMTV integration site family, member 7B (WNT7B), mRNA | gi|17505192|ref|NM_058238.1|[17505192] |
| NM_009528 | *Mus musculus* wingless-related MMTV integration site 7B (Wnt7b), mRNA | gi|6678604|ref|NM_009528.1|[6678604] |
| M89802 | Mouse Wnt-7b mRNA, complete cds | gi|202411|gb|M89802.1|MUSWNTVIIB[202411] |
| Frizzled Nucleotide Sequences | | |
| BC051271 | *Homo sapiens* frizzled homolog 1 (*Drosophila*), mRNA (cDNA clone MGC: 59857 IMAGE: 4874253), complete cds | gi|30410973|gb|BC051271.1|[30410973] |
| BC052266 | *Homo sapiens* frizzled homolog 2 (*Drosophila*), mRNA (cDNA clone IMAGE: 6578442), partial cds | gi|30353963|gb|BC052266.1|[30353963] |
| NM_012193 | *Homo sapiens* frizzled homolog 4 (*Drosophila*) (FZD4), mRNA | gi|22547160|ref|NM_012193.2|[22547160] |
| NM_003505 | *Homo sapiens* frizzled homolog 1 (*Drosophila*) (FZD1), mRNA | gi|4503824|ref|NM_003505.1|[4503824] |
| NM_017412 | *Homo sapiens* frizzled homolog 3 (*Drosophila*) (FZD3), mRNA | gi|22035685|ref|NM_017412.2|[22035685] |
| AF139183 | *Mus musculus* Frizzled-2 protein mRNA, partial cds | gi|4704821|gb|AF139183.1|AF139183[4704821] |
| U82169 | Human frizzled homolog (FZD3) mRNA; complete cds | gi|1906597|gb|U82169.1|HSU82169[1906597] |
| U43205 | *Mus musculus* frizzled-3 protein mRNA, complete cds | gi|1151179|gb|U43205.1|MMU43205[1151179] |
| Secreted/Soluble Frizzled-Related Nucleotide Sequences | | |
| NM_018780 | *Mus musculus* secreted frizzled-related sequence protein 5 (Sfrp5), mRNA | gi|31560420|ref|NM_018780.2|[31560420] |
| BC008666 | *Homo sapiens* secreted frizzled-related protein 2, mRNA (cDNA clone MGC: 9395 | gi|14250457|gb|BC008666.1|[14250457] |

TABLE 2-continued

Representative GenBank Accession Numbers for
Genes Encoding Proteins in the Wnt Signalling Pathways

| Accession No. | Nucleotide Identification | Descriptive Information |
|---|---|---|
| XM_050625 | *Homo sapiens* secreted frizzled-related protein 2 (SFRP2), mRNA | gi|27477718|ref|XM_050625.2|[27477718] |
| NM_003014 | *Homo sapiens* secreted frizzled-related protein 4 (SFRP4), mRNA | gi|8400733|ref|NM_003014.2|[8400733] |
| NM_003012 | *Homo sapiens* secreted frizzled-related protein 1 (SFRP1), mRNA | gi|8400731|ref|NM_003012.2|[8400731] |
| BC034853 | *Mus musculus* secreted frizzled-related sequence protein 4, mRNA (cDNA clone | gi|22028397|gb|BC034853.1|[22028397] |
| BC032921 | *Mus musculus* secreted frizzled-related sequence protein 5, mRNA (cDNA clone MGC: 41101 IMAGE: 1395864), complete cds | gi|21411182|gb|BC032921.1|[21411182] |
| BC014722 | *Mus musculus* secreted frizzled-related sequence protein 2, mRNA (cDNA clone | gi|15928487|gb|BC014722.1|[15928487] |
| BC050435 | *Homo sapiens*, secreted frizzled-related protein 5, clone IMAGE: 6189478, mRNA, | gi|29791957|gb|BC050435.1|[29791957] |
| NM_016687 | *Mus musculus* secreted frizzled-related sequence protein 4 (Sfrp4), mRNA | gi|7710093|ref|NM_016687.1|[7710093] |
| NM_003015 | *Homo sapiens* secreted frizzled-related protein 5 (SFRP5), mRNA | gi|8400734|ref|NM_003015.2|[8400734] |
| NM_013834 | *Mus musculus* secreted frizzled-related sequence protein 1 (Sfrp1), mRNA | gi|7305480|ref|NM_013834.1|[7305480] |
| NM_011356 | *Mus musculus* frizzled-related protein (Frzb), mRNA | gi|6755475|ref|NM_011356.1|[6755475] |
| NM_009144 | *Mus musculus* secreted frizzled-related sequence protein 2 (Sfrp2), mRNA | gi|6677894|ref|NM_009144.1|[6677894] |
| NM_001463 | *Homo sapiens* frizzled-related protein (FRZB), mRNA | gi|4503788|ref|NM_001463.1|[4503788] |
| BC047684 | *Homo sapiens*, Similar to secreted frizzled-related protein 4, clone | gi|28839285|gb|BC047684.1|[28839285] |
| BC026165 | *Homo sapiens*, similar to secreted frizzled-related protein 4; secreted frizzled-related protein 4, clone MGC: 26778 IMAGE: 4837530, mRNA, complete cds | gi|20072880|gb|BC026165.1|[20072880] |
| BC004466 | *Homo sapiens*, Similar to secreted frizzled-related protein 1, clone IMAGE: 3501872, mRNA | gi|14709105|gb|BC004466.1|BC004466[14709105] |
| Dishevelled Nucleotide Sequences | | |
| CD579766 | 1074 hEx1 (RZPD no. 800) *Homo sapiens* cDNA clone 11960 5' similar to SEGMENT POLARITY PROTEIN DISHEVELLED HOMOLOG DVL-1 (DISHEVELLED-1) (DSH HOMOLOG 1). Source: SWISSPROT; Acc: O14640], MRNA sequence | gi|31744091|gb|CD579766.1|[31744091] |
| BC053050 | *Mus musculus* dishevelled 2, dsh homolog (*Drosophila*), mRNA (cDNA clone MGC: 62321 IMAGE: 6402000), complete cds | gi|31419841|gb|BC053050.1|[31419841] |

TABLE 2-continued

Representative GenBank Accession Numbers for
Genes Encoding Proteins in the Wnt Signalling Pathways

| Accession No. | Nucleotide Identification | Descriptive Information |
| --- | --- | --- |
| NM_004421 | *Homo sapiens* dishevelled, dsh homolog 1 (*Drosophila*) (DVL1), mRNA | gi\|4758213\|ref\|NM_004421.1\|[4758213] |
| NM_004423 | *Homo sapiens* dishevelled, dsh homolog 3 (*Drosophila*) (DVL3), mRNA | gi\|6806886\|ref\|NM_004423.2\|[6806886] |
| NM_010091 | *Mus musculus* dishevelled, dsh homolog 1 (*Drosophila*) (Dvl1), mRNA | gi\|6753695\|ref\|NM_010091.1\|[6753695] |
| NM_007889 | *Mus musculus* dishevelled 3, dsh homolog (*Drosophila*) (Dvl3), mRNA | gi\|6681240\|ref\|NM_007889.1\|[6681240] |
| NM_007888 | *Mus musculus* dishevelled 2, dsh homolog (*Drosophila*) (Dvl2), mRNA | gi\|6681238\|ref\|NM_007888.1\|[6681238] |
| NM_004422 | *Homo sapiens* dishevelled, dsh homolog 2 (*Drosophila*) (DVL2), mRNA | gi\|4758215\|ref\|NM_004422.1\|[4758215] |
| BC025292 | *Homo sapiens*, dishevelled, dsh homolog 1 (*Drosophila*), clone IMAGE: 4554266, mRNA | gi\|19263756\|gb\|BC025292.1\|[19263756] |
| U28138 | *Mus musculus* dishevelled-1 protein (Dvl1) gene, complete cds | gi\|930346\|gb\|U28138.1\|MMU28138[930346] |
| BC014844 | *Homo sapiens*, dishevelled 2 (homologous to *Drosophila* dsh), clone MGC: 9545 IMAGE: 3852554, mRNA, complete cds | gi\|15928770\|gb\|BC014844.1\|BC014844[15928770] |
| U41285 | *Mus musculus* dishevelled-3 (Dvl-3) mRNA, complete cds | gi\|1353660\|gb\|U41285.1\|MMU41285[1353660] |
| Glycogen Synthase Kinase-3 Beta Nucleotide Sequences | | |
| XM_291773 | *Homo sapiens* similar to Glycogen synthase kinase-3 beta (GSK-3 beta) (LOC340894), mRNA | gi\|29740969\|ref\|XM_291773.1\|[29740969] |
| BC006936 | *Mus musculus* glycogen synthase kinase 3 beta, mRNA (cDNA clone MGC: 6814 | gi\|13905273\|gb\|BC006936.1\|[13905273] |
| NM_002093 | *Homo sapiens* glycogen synthase kinase 3 beta (GSK3B), mRNA | gi\|21361339\|ref\|NM_002093.2\|[21361339] |
| NM_019827 | *Mus musculus* glycogen synthase kinase 3 beta (Gsk3b), mRNA | gi\|9790076\|ref\|NM_019827.1\|[9790076] |
| AY123976 | *Homo sapiens* glycogen synthase kinase 3 beta (GSK3B) mRNA, partial cds, alternatively spliced | gi\|27764568\|gb\|AY123976.1\|[27764568] |
| AF156099 | *Mus musculus* glycogen synthase kinase 3 beta mRNA, complete cds | gi\|7025914\|gb\|AF156099.2\|AF156099[7025914] |
| AF098789 | *Homo sapiens* glycogen synthase kinase 3-beta gene, partial cds | gi\|3800882\|gb\|AF098789.1\|AF098789[3800882] |
| Beta-Catenin Nucleotide Sequence | | |
| NM_007614 | *Mus musculus* catenin beta (Catnb), mRNA | gi\|31560726\|ref\|NM_007614.2\|[31560726] |

Nucleic acid sequences encoding a polypeptide or peptide modulator according to the present invention can be readily purified from a suitable source by standard techniques, or can be synthesised chemically. The nucleic acids can be genomic DNA, RNA, cDNA prepared from isolated mRNA, or DNA amplified from a naturally occurring nucleic acid sequence by standard techniques. Suitable sources for obtaining the nucleic acids are those cells which are known to express Wnt proteins and other proteins in the Wnt signalling cascade. An example of such-ells would be primary myoblasts.

Nucleic acid sequences encoding fragments or variants of the wild-type proteins can be constructed by deletion, addition, and/or substitution of one or more nucleotides within the coding sequence using standard techniques, such as site-directed mutagenesis.

The polypeptides and peptides of the present invention can also be produced as fusion proteins. One use of such fusion proteins is to improve the purification or detection of the polypeptide or peptide. For example, a polypeptide or peptide can be fused to an immunoglobulin Fc domain and the resultant fusion protein can be readily purified using a protein A columns Other examples of fusion proteins include polypeptides or peptides fused to histidine tags (allowing for purification on $Ni^{2+}$ resin columns), to glutathione-S-transferase (allowing purification on glutathione columns) or to biotin (allowing purification on streptavidin columns or with streptavidin labelled magnetic beads).

Specific initiation signals may be required for efficient translation of cloned nucleic acid sequences. These signals include the ATG initiation codon and adjacent sequences. In cases where an entire wild-type gene or cDNA, including its own initiation codon and adjacent sequences, is inserted into the appropriate expression vector, additional translational control signals may not be needed. In other cases, exogenous translational control signals, including, perhaps, the ATG initiation codon, must be provided. Furthermore, the initiation codon must be in phase with the reading frame of the desired coding sequence to ensure translation of the entire insert The exogenous translational control signals and initiation codons can be natural or synthetic. The efficiency of expression may be enhanced by the inclusion of appropriate transcription enhancer elements and/or transcription terminators (Bittner et al. (1987) *Methods in Enzymol.* 153, 516).

Suitable expression vectors for use with the nucleic acid sequences of the present invention include, but are not limited to, plasmids, phagemids, viral particles and vectors, phage and the like. For insect cells, baculovirus expression vectors are suitable. For plant cells viral expression vectors (such as cauliflower mosaic virus and tobacco mosaic virus) and plasmid expression vectors (such as the Ti plasmid) are suitable. The entire expression vector, or a part thereof can be integrated into the host cell genome. In some circumstances, it is desirable to employ an inducible expression vector, e.g., the LACSWITCH™ Inducible Expression System (Stratagene, LaJolla, Calif.).

Those skilled in the field of molecular biology will understand that a wide variety of expression systems can be used to provide the recombinant polypeptide or peptide. The precise host cell used is not critical to the invention. The polypeptide or peptide can be produced in a prokaryotic host (e.g., *E. coli* or *B. subtilis*) or in a eukaryotic host (e.g., *Saccharomyces* or *Pichia*; mammalian cells, such as COS, NIH 3T3, CHO, BHK, 293, 293-T, ATt-20 or HeLa cells; insect cells; or plant cells). The methods of transformation or transfection and the choice of expression vector will depend on the host system selected and can be readily determined by one skilled in the art Transformation and transfection methods are described, for example, in Ausubel et al. (1.994) Current Protocols in Molecular Biology, John Wiley & Sons, New York; and various expression vectors may be chosen from those provided, e.g., in Cloning Vectors: A Laboratory Manual (Pouwels et al., 1985, Supp. 1987).

In addition, a host cell may be chosen which modulates the expression of the inserted sequences, or modifies and processes the gene product in a specific, desired fashion. Such modifications (e.g., glycosylation) and processing (e.g. cleavage) of protein products may be important for the activity of the protein. Different host cells have characteristic and specific mechanisms for the post-translational processing and modification of proteins and gene products. Appropriate cell lines or host systems can be chosen by one skilled in the art to ensure the correct modification and processing of the foreign protein expressed.

The host cells harbouring the expression vehicle can be cultured in conventional nutrient media adapted as needed for activation of a chosen gene, repression of a chosen gene, selection of transformants, or amplification of a chosen gene.

(iii) Oligonucleotides

The present invention also contemplates oligonucleotide inhibitors and activators that are targeted to a Wnt gene or a gene encoding an activator or effector of a Wnt protein or gene. In the context of the present invention, the terms "oligonucleotide inhibitor" and "oligonucleotide activator" encompass antisense oligonucleotides, short interfering RNA (siRNA) molecules, ribozymes and triple helix-forming oligonucleotides.

The term "oligonucleotide," as used herein, refers to an oligomer or polymer of ribonucleic acid (RNA), deoxyribonucleic acid (DNA), or modified versions thereof or RNA or DNA mimetics. This tern, therefore, includes oligonucleotides composed of naturally occurring nucleobases, sugars and covalent internucleoside (backbone) linkages as well as oligonucleotides having non-naturally-occurring portions, which function similarly. Such modified or substituted oligonucleotides are often preferred over native forms because of desirable properties such as, for example, enhanced cellular uptake, enhanced affinity for the nucleic acid target and increased stability in the presence of nucleases. The term also includes chimeric oligonucleotides. Chimeric oligonucleotides are oligonucleotides that contain two or more chemically distinct regions, each region comprising at least one monomer unit. The oligonucleotides according to the present invention can be single-stranded or they can be double-stranded.

Examples of oligonucleotides useful in this invention include those containing modified backbones or non-natural internucleoside linkages such as phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogues of these, and analogues having inverted polarity wherein the adjacent pairs of nucleoside units are linked 3'-5' to 5'-3' or 2'-5' to 5'-2'. Various salts, mixed salts and free acid forms are also included.

Other examples of modified backbones contemplated by the present invention include those formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include morpholino linkages (formed in part from the sugar portion of a nucleoside); siloxane backbones; sulphide, sulphoxide and sulphone backbones; formacetyl and thioformacetyl backbones; methylene formacetyl and thioformacetyl backbones; alkene containing backbones; sulphamate backbones; methyleneimino and methylenehydrazino backbones; sulphonate and sulphonamide backbones; amide backbones; and others having mixed N, O, S and $CH_2$ component parts.

The term "alkyl" as used herein refers to monovalent alkyl groups having from 1 to 20 carbon atoms. Examples of suitable alkyl groups include, but are not limited to, methyl, ethyl n-propyl, iso-propyl, n-butyl, iso-butyl, n-hexyl, and the like.

The term "cycloalkyl" refers to cyclic alkyl groups of from 3 to 20 carbon atoms having a single cyclic ring or multiple condensed rings. Examples of suitable cycloalkyl groups include, but are not limited to, single ring structures such as cyclopropyl, cyclobutyl, cyclopentyl, cyclooctyl and the like, or multiple ring structures such as adamantanyl, and the like.

The present invention also contemplates oligonucleotide mimetics in which both the sugar and the internucleoside linkage of the nucleotide units are replaced with novel groups. The base units are maintained for hybridization with an appropriate nucleic acid target An example of such an oligonucleotide mimetic, which has been shown to have excellent hybridization properties, is a peptide nucleic acid (PNA) [Nielsen et al., Science, 254:1497-1500 (1991)]. In PNA compounds, the sugar-backbone of an oligonucleotide is replaced with an amide-containing backbone, in particular an aminoethylglycine backbone. The nucleobases are retained and are bound directly or indirectly to aza-nitrogen atoms of the amide portion of the backbone.

The present invention also contemplates oligonucleotides comprising "locked nucleic acids" (LNAs), which are novel conformationally restricted oligonucleotide analogues containing a methylene bridge that connects the 2'-O of ribose with the 4'-C (see, Singh et al., Chem. Commun., 1998, 4:455-456). LNA and LNA analogues display very high duplex thermal stabilities with complementary DNA and RNA, stability towards 3'-exonuclease degradation, and good solubility properties. Synthesis of the LNA analogues of adenine, cytosine, guanine, 5-methylcytosine, thymine and uracil, their oligomerization, and nucleic acid recognition properties have been described (see Koshkin et al., Tetrahedron, 1998, 54:3607-3630). Studies of mis-matched sequences show that LNA obey the Watson-Crick base pairing rules with generally improved selectivity compared to the corresponding unmodified reference strands.

Antisense oligonucleotides containing LNAs have been described (Wahlestedt et al., Proc. Natl. Acad Sci. U.S.A., 2000, 97:5633-5638), which were efficacious and non-toxic. In addition, the LNA/DNA copolymers were not degraded readily in blood serum and cell extracts. LNAs form duplexes with complementary-DNA or RNA or with complementary LNA, with high thermal affinities. The universality of LNA-mediated hybridization has been emphasized by the formation of exceedingly stable LNA:LNA duplexes (Koshkin et al., J. Am. Chem. Soc., 1998, 120:13252-13253). LNA:LNA hybridization was shown to be the most thermally stable nucleic acid type duplex system, and the RNA-mimicking character of LNA was established at the duplex level. Introduction of three LNA monomers (T or A) resulted in significantly increased melting points toward DNA complements:

Synthesis of 2'-amino-LNA (Singh et al., J. Org. Chem., 1998, 63, 10035-10039) and 2'-methylamino-LNA has been described and thermal stability of their duplexes with complementary RNA and DNA strands reported Preparation of phosphorothioate-LNA and 2'-thio-LNA have also been described (Kumar et al., Bioorg. Med. Chem. Lett., 1998, 8:2219-2222).

Modified oligonucleotides according to the present invention may also contain one or more substituted sugar moieties. For example, oligonucleotides may comprise sugars with one of the following substituents at the 2' position: OH; F; O-, S-, or N-alkyl; O-, S-, or N-alkenyl; O-, S- or N-alkynyl; or O-alkyl-O-alkyl wherein the alkyl, alkenyl and alkynyl may be substituted or unsubstituted $C_1$ to $C_{10}$ alkyl or $C_2$ to $C_{10}$ alkenyl and alkynyl. Examples of such groups are: $O[(CH_2)_n O]_m CH_3$, $O(CH_2)_n OCH_3$, $O(CH_2)_n NH_2$, $O(CH_2)_n CH_3$, $O(CH_2)_n ONH_2$, and $O(CH_2)_n ON[(CH_2)_n CH_3)]_2$, where n and m are from 1 to about 10. Alternatively, the oligonucleotides may comprise one of the following-substituents at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2$, $CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Specific examples include 2'-O-methyl(2'-O—$CH_3$), 2'-methoxyethoxy(2'-O—$CH_2CH_2OCH_3$, also known as 2'-O-(2-methoxyethyl) or 2'-MOE) [Martin et al., Helv. Chim. Acta, 78:486-504(1995)], 2'-dimethylaminooxyethoxy(2'-O($CH_2)_2ON(CH_3)_2$ group, also known as 2'-DMAOE), 2'-aminopropoxy(2'-O$CH_2CH_2CH_2NH_2$) and 2'-fluoro (2'-F).

Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also comprise sugar mimetics such as cyclobutyl moieties in place of the pentofuranosyl sugar.

Oligonucleotides according to the present invention may also include modifications or substitutions to the nucleobase. As used herein, "unmodified" or "natural" nucleobases include the purine bases adenine (A) and guanine (G), and the pyrimidine bases thymine (I), cytosine (C) and uracil (U).

Modified nucleobases include other synthetic and natural nucleobases such as 5-methylcytosine (5-me-C); inosine; 5-hydroxymethyl cytosine; xanthine; hypoxanthine; 2-aminoadenine; 6-methyl and other alkyl derivatives of adenine and guanine; 2-propyl and other alkyl derivatives of adenine and guanine; 2-thiouracil, 2-thiothymine and 2-thiocytosine; 5-halouracil and cytosine; 5-propynyl uracil and cytosine; 6-azo uracil, cytosine and thymine; 5-uracil (pseudouracil); 4-thiouracil; 8-halo, 8-amino, 8-thiol, 8-thioalkyl, 1, 8-hydroxyl and other 8-substituted adenines and guanines; 5-halo particularly 5-bromo, 5-trifluoromethyl and other 5-substituted uracils and cytosines; 7-methylguanine and 7-methyladenine; 8-azaguanine and 8-azaadenine; 7-deazaguanine and 7-deazaadenine; 3-deazaguanine and 3-deazaadenine. Further nucleobases include those disclosed in U.S. Pat. No. 3,687,808; The Concise Encyclopaedia Of Polymer Science And Engineering, (1990) pp 858-859, Kroschwitz, J. I., ed. John Wiley & Sons; Englisch et-al., Angewandte Chemie, Int Ed., 30:613 (1991); and Sanghvi, Y. S., (1993) Antisense Research and Applications, pp 289-302, Crooke, S. T. and Lebleu, B., ed., CRC Press. Certain of these nucleo'bases are particularly useful for increasing the binding affinity of the oligomeric compounds of the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. [Sanghvi, Y. S., (1993) Antisense Research and Applications, pp 276-278, Crooke, S. T. and L-ebleu, B., ed., CRC Press, Boca Raton]. Another oligonucleotide modification included in the present invention is the chemical linkage to the oligonucleotide of one or more moieties or conjugates which enhance the activity, cellular distribution or cellular uptake of the oligonucleotide. Such moieties include, but are not limited to, lipid moieties such as a cholesterol moiety [Letsinger et al., Proc. Natl. Acad. Sci. USA, 86:6553-6556 (1989)], cholic acid [Manoharan et al., Bioorg. Med. Chem. Let, 4:1053-1060 (1994)], a thioether, e.g. hexyl-S-tritylthiol [Manoharan et al., Ann. N.Y. Acad. Sci., 660:306-309 (1992); Midoharanet al., Bioorg. Med. Chen Lett, 3:2765-2770 (1993)], a thiocholesterol [Oberhauser et al., Nucl. Acids Res., 20:533-538 (1992)], an aliphatic chain, e.g. dodecandiol or undecyl residues [Saison-Behmoaras et al., EMBO J., 10:1111-1118 (1991); Kabanov et al., FEBS Lett., 259:327-330 (1990); Svinarchuk et al., Biochimie, 75:49-54 (1993)], a phospholipid, e.g. di-hexadecyl-rac-glycerol or triethylammonium 1,2-di-O-hexadecyl-rac-glycero-3-H-phosphonate [Manoharan et al., Tetrahedron Lett., 36:3651-3654 (1995); Shea et al., Nucl. Acids Res., 18:3777-3783 (1990)], a polyamine or a polyethylene glycol chain [Manoharan et al., Nucleosides & Nucleotides, 14:969-973 (1995)], or adamantane acetic acid [Manoharan et al., Tetrahedron Lett, 36:3651-3654 (1995)], a palmityl moiety [Mishra et al. Biochim. Biophys. Acta, 1264:229-237 (1995)], or an octadecylamine or hexylamino-carbonyl-oxycholesterol moiety [Crooke et al., J. Pharmacol. Exp. Ther., 277:923-937 (1996)].

One skilled in the art will recognise that it is not necessary for all positions in a given oligonucleotide to be uniformly modified. The present invention, therefore, contemplates the incorporation of more than one of the aforementioned modifications into a single oligonucleotide or even at a single nucleoside within the oligonucleotide.

As indicated above, oligonucleotides that are chimeric compounds are included within the scope of the present invention. Chimeric oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids.

In the context of the present invention, an oligonucleotide is "nuclease resistant" when it has either been modified such that it is not susceptible to degradation by DNA and RNA nucleases or, alternatively, has been placed in a delivery vehicle which itself protects the oligonucleotide from DNA or RNA nucleases. Nuclease resistant oligonucleotides include, for example, methyl phosphonates, phosphorothioates, phosphorodithioates, phosphotriesters, and morpholino oligomers. Suitable delivery vehicles for conferring nuclease resistance include, for example, liposomes.

The present invention further contemplates oligonucleotides that contain groups for improving the pharmacokinetic and/or pharmacodynamic properties of the oligonucleotide.

The term "antisense oligonucleotide," as used herein, indicates an oligonucleotide having a nucleotide sequence that is complementary to a portion of the mRNA transcribed from a gene of interest. In the context of the present invention, a gene of interest is a gene that encodes a protein of interest, i.e. a protein in the Wnt signaling pathways and the antisense oligonucleotides are targeted to that gene. The targeting process includes determination of a site, or sites, within this nucleic acid sequence for the antisense interaction to occur such that the desired effect, i.e. modulation of expression of the protein encoded by the gene, will result. Once the target site, or sites, has been identified, oligonucleotides are chosen that are sufficiently complementary (i.e. hybridise with sufficient strength and specificity) to the target to give the desired result.

Generally, there are five regions of a gene, or mRNA transcribed therefrom, that may be targeted for antisense modulation: the 5' untranslated region (5'-UTR), the translation initiation (or start) codon region, the open reading frame (ORF), the translation termination (or stop) codon region and the 3' untranslated region (3'-UTR).

As is known in the art some eukaryotic transcripts are directly translated, however, most mammalian genes, or open reading frames (ORFs), contain one or more sequences, known as "introns," which are excised from a transcript before it is translated. The expressed (unexcised) portions of the ORF are referred to as "exons" and are spliced together to form an mRNA transcript (Alberts et al., (1983) Molecular Biology of the Cell, Garland Publishing Inc., New York, pp. 411-415). In the context of the present invention, both introns and exons may serve as targets for antisense as well as intron/exon splice sites. In addition, mRNA molecules possess a 5' cap region that may also serve as a target for antisense. The 5' cap of a mRNA comprises an $N^7$-methylated guanosine residue joined to the 5'-most residue of the mRNA via a 5'-5' triphosphate linkage. The 5' cap region of a mRNA is considered to include the 5' cap structure itself as well as the first 50 nucleotides adjacent to the cap.

The antisense oligonucleotides in accordance with the present invention are selected from a sequence complementary to a gene of interest such that the sequence exhibits the least likelihood of forming duplexes, hair-pins, or of containing homooligomer/sequence repeats. The oligonucleotide may further contain a GC clamp. One skilled in the art will appreciate that these properties can be determined qualitatively using various computer modelling programs, for example, the program OLIGO® Primer Analysis Software, Version 5.0 (distributed by National Biosciences, Inc., Plymouth, Minn.).

It is understood in the art that an antisense oligonucleotide need not have 100% identity with the complement of its target sequence in order to be effective. The antisense oligonucleotides in accordance with the present invention, therefore, have a sequence that is at least about 70% identical to the complement of the target sequence. In one embodiment of the present invention, the antisense oligonucleotides have a sequence that is at least about 80% identical to the complement of the target sequence. In other embodiments, they have a sequence that is at least about 90% identical or at least about 95% identical to the complement of the target sequence, allowing for gaps or mismatches of several bases. Identity can be determined, for example, by using the BLASTN program of the University of Wisconsin Computer Group (GCG) software.

In order for the antisense oligonucleotides of the present invention to function in inhibiting expression of a gene of interest, it is necessary that they demonstrate adequate specificity for the target sequence and do not bind to other nucleic acid sequences in the cell. Therefore, in addition to possessing an appropriate level of sequence identity to the complement of the target sequence, the antisense oligonucleotides of the present invention should not closely resemble other known sequences. The antisense oligonucleotides of the present invention, therefore, should be less than 50% identical to any other mammalian nucleic acid sequence.

The antisense oligonucleotides according to the present invention are typically between 7 and 100 nucleotides in length. In one embodiment, the antisense oligonucleotides comprise from about 7 to about 50 nucleotides, or nucleotide analogues. In another embodiment, the antisense oligonucleotides comprise from about 7 to about 35 nucleotides, or nucleotide analogues. In other embodiments, the antisense oligonucleotides comprise from about 12 to about 35 nucleotides, or nucleotide analogues, and from about 15 to about 25 nucleotides, or nucleotide analogues.

The present invention also contemplates oligonucleotide modulators that are short interfering double-stranded RNA molecules (siRNAs). RNA interference mediated by siRNAs is known in the aft to play an important role in post-transcriptional gene silencing [Zamore, Nature Struc. Biol., 8:746-750 (2001)]. In nature, siRNA molecules are typically 21-22 base pairs in length and are generated when long double-stranded RNA molecules are cleaved by the action of an endogenous ribonuclease. Recently, it has been demonstrated that transfection of mammalian cells with synthetic siRNA molecules having a sequence identical to a portion of a target gene leads to a reduction in the mRNA levels of the target gene [Elbashir, et al., Nature, 411:4914-498 (2001)].

The oligonucleotide inhibitors according to the present invention can be siRNA molecules that are targeted to a gene of interest such that the sequence of the siRNA corresponds to a portion of said gene. As is known in the art, effective siRNA molecules are typically less than 30 base pairs in length to help-prevent them triggering non-specific RNA interference pathways in the cell via the interferon response. Thus, in one embodiment of the present invention, the siRNA molecules are between about 15 and about 25 base pairs in length. In another embodiment, they are between about 19 and about 22 base pairs in length The double-stranded siRNA molecules can further comprise poly-T or poly-U overhangs at the 3' and 5' ends to minimise RNase-mediated degradation of the molecules. Typically, the overhangs at the 3' and 5' ends comprise two thymidine or two uridine residues. Design and construction of siRNA molecules is known in the art [see, for example, Elbashir, et al, Nature, 411:494-498 (2001); Bitko and Barik, BMC Microbiol., 1:34 (2001)]. In addition, kits that provide a rapid and efficient means of constructing siRNA molecules by in vitro transcription are also commercially available (Ambion, Austin, Tex.; New England Biolabs, Beverly, Mass.) and may be used to construct the siRNA molecules of to the present invention.

The present invention further contemplates ribozyme oligonucleotide modulators that specifically target mRNA encoding a protein of interest. As is known in the art, ribozymes are RNA molecules having an enzymatic activity that enables the ribozyme to repeatedly cleave other separate RNA molecules in a nucleotide-sequence specific manner. Such enzymatic RNA molecules can be targeted to virtually any mRNA transcript, and efficient cleavage can be achieved in vitro [Kim et al., Proc. Natl. Acad. Sci. USA, 84:8788, (1987); Haseloff and Gerlach, Nature, 334:585, (1988); Cech, JAMA, 260:3030, (1988); Jefferies et al., Nucleic Acids Res., 17:1371, (1989)].

Typically, a ribozyme comprises two portions held in close proximity: a mRNA binding portion having a sequence complementary to the target mRNA sequence, and a catalytic portion which acts to cleave the target mRNA. A ribozyme acts by first recognising and binding a target mRNA by complementary base-pairing through the target mRNA binding portion of the ribozyme. Once it is specifically bound to its target, the ribozyme catalyses cleavage of the target mRNA. Such strategic cleavage destroys the ability of a target mRNA to direct synthesis of an encoded protein. Having bound and cleaved its mRNA target, the ribozyme is released and can repeatedly bind and cleave new target mRNA molecules.

One of the best characterised ribozyme molecules is the "hammerhead ribozyme." Hammerhead ribozymes comprise a hybridising region which is complementary in nucleotide sequence to at least part of the target mRNA, and a catalytic region which is adapted to cleave the target mRNA. In general, the hybridising region contains at least 9 nucleotides. The present invention therefore contemplates oligonucleotide inhibitors that are hammerhead ribozymes having a hybridising region that comprises at least 9 nucleotides that are complementary to a gene encoding protein of interest, and which is joined to an appropriate catalytic domain. The construction and production of such ribozymes is well known in the art [see, for example, Haseloff and Gerlach, Nature, 334: 585-591 (1988)].

Ribozymes in accordance with the present invention also include RNA endoribonucleases (hereinafter "Cech-type ribozymes") such as the one which occurs naturally in Tetrahymena thermophila (known as the IVS, or L-19 IVS RNA), which has been extensively described in the literature (see, Zaug, et al., Science, 224:574-578 (1984); Zaug and Cech, Science, 231:470-475 (1986); Zaug, et al., Nature, 324:429-433 (1986); U.S. Pat. No. 4,987,071; Been and Cech, Cell, 47:207-216 (1986)). Cech-type ribozymes comprise an 8 nucleotide active site which hybridises to a target mRNA sequence with subsequent cleavage of the target mRNA by the ribozyme.

One skilled in the art will understand that there is a narrow range of binding free energies between a ribozyme and its substrate that will produce maximal ribozyme activity. Such binding energy can be optimized by making ribozymes with G to I (inosine) and U to BrU (bromouracil) substitutions (or equivalent substitutions as known in the art) in the mRNA binding portion. Such substitutions allow manipulation of the binding free energy without altering the target recognition sequence, the length of the mRNA binding portion, or the enzymatic portion of the ribozyme. The shape of the free-energy vs. ribozyme activity curve can be readily determined using data from standard experiments known in the art in which each base (or several bases) is modified or unmodified, and without the complication of changing the size of the ribozyme/substrate interaction If necessary, such experiments can be used to indicate the most active ribozyme structure. The use of modified bases thus permits "fine tuning" of the binding free energy to assure maximal ribozyme activity and is considered to be within the scope of the present invention. In addition, replacement of such bases, for example, I for G, may permit a higher level of substrate specificity when cleavage of non-target RNA is a problem.

The present invention further contemplates oligonucleotide modulators that hybridise to and forms triple helix structures at the 5' terminus of the target gene and can thus be used to block transcription. The triple helix forming oligonucleotides can be designed and prepared as described above for antisense oligonucleotides.

The oligonucleotide modulators of the present invention can be prepared by conventional techniques well-known to those skilled in the art. For example, the oligonucleotides can be prepared using solid-phase synthesis using commercially available equipment, such as the equipment available from Applied Biosystems Canada Inc. (Mississauga, Canada). As is well-known in the art, modified oligonucleotides, such as phosphorothioates and alkylated derivatives, can also be readily prepared by similar methods.

Alternatively, the oligonucleotide modulators can be prepared by enzymatic digestion and/or amplification of the naturally occurring target gene or mRNA, or of cDNA synthesized from the mRNA, using standard techniques known in the art When the oligonucleotide inhibitors comprise RNA, they can be prepared by in vitro transcription methods also known in the art As indicated above, siRNA molecules can also be conveniently prepared using commercially available in vitro transcription kits.

Oligonucleotides can also be prepared using recombinant DNA techniques. The present invention, therefore, encompasses expression vectors comprising nucleic acid sequences that encode the oligonucleotide inhibitors and subsequent expression of the encoded oligonucleotides in a suitable host cell. Such expression vectors can be readily constructed using procedures known in the art [see, for example, Ausubel, et al., Current Protocols in Molecular Biology, John riley & Sons, Inc, NY. (1989 and updates)].

(iv) Antibodies

The present invention also contemplates the use of antibodies, and antibody fragments, raised against a target protein in the Wnt signalling pathways and which can bind to and inhibit the protein In the context of the present invention, a target protein is a Wnt protein or an activator or effector of a Wnt protein.

In one embodiment of the present invention, the modulator is an antibody or antibody fragment that specifically binds to a sFRP, such as sFRP 1, 2, 3 or 4 and thus prevents the sFRP from binding a Wnt polypeptide. In this embodiment, the antibody or antibody fragment acts as an activator of the Wnt pathways. In another embodiment, the modulator is an antibody or antibody fragment that binds to a Fzd receptor protein, such as Fzd 1, 4 or 7 and thus prevents the Fzd protein from binding a Wnt polypeptide. In this embodiment, the antibody or antibody fragment acts as an inhibitor of the Wnt pathways.

For the production of antibodies, various hosts including, for example, goats, rabbits, rats, mice and humans, can be immunised with the target protein, or with a fragment or peptide thereof that has immunogenic properties. Depending on the host species, various adjuvants may be used to increase the immunological response. Such adjuvants include, but are not limited to, Freund's adjuvant, mineral gels such as aluminium hydroxide, and surface active substances such as lysolecithin, pluronic polyols, polyanions, peptides, oil emulsions, Keyhole limpet hemolysin (KLH), and dinitrophenol. Examples of adjuvants used in humans include, for example, BCG (bacilli Calmette-Guerin) and *Corynebacterium parvum*.

The peptides or protein fragments used to induce antibodies an have an amino acid sequence consisting of as little as about 5 amino acids. These peptides or protein fragments can be identical to a portion of the amino acid sequence of the wild-type protein or can contain the entire amino acid sequence of a small, naturally occurring molecule. If required, short stretches of amino acids of the target protein can be fused with those of another protein, such as KLH, and antibodies to the chimeric molecule can be produced.

Monoclonal antibodies to a target protein can be prepared using techniques that provide for the production of antibody molecules by continuous cell lines in culture. These include, but are not limited to, the hybridoma technique, the human B-cell hybridoma technique and the EBV-hybridoma technique (see, for example, Kohler, G. et al. (1975) Nature 256: 495-497; Kozbor, D. et al. (1985) J. Immunol. Methods 81:31-42; Cote, R J. et al. (1983) Proc. Natl. Aca Sci. USA, 80:2026-2030; and Cole, S. P. et al. (1984) Mol. Cell Biol. 62:109-120). For example, the monoclonal antibodies according to the present invention can be obtained by immunising animals, such as mice or rats, with purified protein. Spleen cells isolated from the immunized animals are then immortalised using s techniques.

Immortalization of the spleen cells from immunised animals can be carried out, for example, by fusing these cells with a myeloma cell line, such as P3×63-Ag 8.653 (ATCC CRL 1580), according to the method described in (1980) *J. Imm. Meth.* 39:285-308. Other methods known in the art can also be used to immortalise spleen cells. In order to detect immortalized cells that produce the desired antibody against the target protein, a sample of the culture supernatant is tested for reactivity using, for example, an enzyme linked immunosorbent assay (ELISA). In order to obtain those antibodies that inhibit the activity of the target protein, the culture supernatant of clones that produce antibodies that bind to the protein is additionally examined for inhibition of protein activity using an appropriate assay. Isolated immortalised cells whose culture supernatant contains an antibody that inhibits of the activity of the target protein and has an $IC_{50}$ of less than about 100 ng/ml are then selected and cloned using techniques known to one skilled in the art. The monoclonal antibodies produced by these clones are then isolated according to standard protocols, In addition, techniques developed for the production of "chimeric antibodies," such as the splicing of mouse antibody genes to human antibody genes to obtain a molecule with appropriate antigen specificity and biological activity, can be used (Morrison, S. L. et al. (1984) Proc. Natl. Acad. Sci. 81:6851-6855; Neuberger, M. S. et al. (1984) Nature 312: 604-608; and Takeda, S. et al. (1985) Nature 314:452454). Alternatively, techniques described for the production of single chain antibodies can be adapted, using methods known in-the art, to produce single chain antibodies specific to the target protein. Antibodies with related specificity, but of distinct idiotypic composition, can be generated by chain shuffling from random combinatorial immunoglobulin libraries (see, for example, Burton D. R (1991) *Proc. Natl. Acad. Sci. USA*, 88:10134-10137).

Antibodies can also be produced by-inducing in vivo production in the lymphocyte population or by screening immunoglobulin libraries or panels of highly specific binding reagents as disclosed in the literature (Orlandi, R. et al. (1989) *Proc. Natl. Acad. Sci.* 86: 3833-3837; Winter, G. et al. (1991) *Nature* 349:293-299).

Antibody fragments which contain specific binding sites for the target protein can also be generated, for example, F(ab')2 fragments can be produced by pepsin digestion of the antibody molecule and Fab fragments can subsequently be generated by reducing the disulphide bridges of the F(ab')2 fragments. Alternatively, Fab expression libraries can be constructed to allow rapid and easy identification of monoclonal Fab fragments with the desired-specificity (see, for-example, Huse, W. D. et al. (1989) *Science* 246:1275-1281).

(v) Small Molecule Modulators

The present invention also provides for small molecule modulators-of the Wnt signalling pathways, including peptides, oligonucleotides and synthesised and naturally occurring organic and inorganic molecules. As an example, lithium chloride (LiCl) is a known stimulator of the Wnt signalling pathways in stem cells that acts through inhibition GSK-3β with consequent stabilisation of β-catenin (Hedgepeth, et al., (1997) *Dev. Biol.*, 185:82-91).

Candidate compounds that can be screened for their ability to act as modulators of the Wnt signaling pathways in stem cells can be randomly selected or rationally selected or designed As used herein, a candidate compound is said to be randomly selected when the compound is chosen randomly without considering the specific interactions involved in its potential association with molecular components of the stem cells, or other cells if culture is used. An example of random selection of candidate compounds is the use a chemical library or a peptide combinatorial library, or a growth broth of an organism. As used herein, a candidate-compound is said to be rationally selected or designed when the compound is chosen on a non-random basis which takes into account the sequence and or conformation of a target site or a process in connection with the compound's action. Candidate compounds can be rationally selected or rationally designed, for example, by using the nucleotide or peptide sequences that make up the target sites. For example, a rationally selected peptide can be a peptide whose amino acid sequence is identical to or a derivative of a functional consensus site.

The candidate compound may be isolated or unisolated, pure, partially purified, or in the form of a crude mixture, for example, it may be in the form of a cell, a lysate or extract derived from a cell, or a molecule derived from a cell. Where the candidate compound is present in a composition that comprises more than one molecular entity, it is contemplated that the composition may be tested as is and/or may optionally be fractionated by a suitable procedure and the fractionated sample tested using the method of the invention or another method to identify a particular fraction or component of the composition that acts as a modulator of the Wnt signalling pathways. It is further contemplated that sub-fractions of test compositions may be re-fractionated and assayed repeatedly using the methods of the invention with the ultimate goal of excluding inactive components from the sub-combination identified as a modulator of the Wnt signalling pathways. Intervening steps of compound isolation, purification and/or characterisation may be included as needed or appropriate.

Candidate compounds can be obtained in the form of large libraries of synthetic or natural compounds. Numerous means are currently used for random and directed synthesis of saccharide, peptide, and nucleic acid based compounds and are well-known in the art. Synthetic compound libraries are commercially available from a number of companies including Maybridge Chemical Co. (Trevillet, Cornwall, UK), Comgenex (Preton, N.J.), Brandon Associates (Merrimack, N.H.), and Microsource (New Milford, Conn.). A rare chemical library is available from Aldrich Milwaukee, Wis.). Combinatorial libraries are also available or can be prepared according to standard procedures. Alternatively, libraries of natural compounds in the form of bacterial, fungal, plant, and animal extracts are available from, for example, Pan Laboratories (Bothell, Wash.) or MycoSearch (North Carolina), or can be readily produced. Additionally, natural and synthetically produced libraries and compounds are readily modified through conventional chemical, physical, and biochemical means.

Selection of Modulators of the Wnt Signalling Pathways

The present invention further provides for methods of screening candidate compounds for their ability to modulate proliferation and/or lineage commitment of adult stem cells through modulation of the Wnt signaling pathways. In general such methods comprise the step of contacting a population of adult stem cells with a candidate compound and monitoring one or more indicators of proliferation and/or lineage commitment in the cell.

If required, candidate modulators may be screened initially for their ability to inhibit or activate their target protein or gene. For example, for polypeptides or peptides (or derivatives, analogues or peptidomimetics thereof) that bind a specific protein in the Wnt signalling pathways, the binding ability can be determined using one of a variety of binding assays known in the art (see, for example, Coligan et al., (eds.) *Current Protocols in Protein Science*, J. Wiley & Sons, New York, N.Y.). For oligonucleotide modulators the up or down-regulation of the target gene can be monitored in treated cells by, for example, Northern blot analysis, quantitative RT-PCR or microarray analysis. Alternatively, the increase or decrease in the corresponding protein can be monitored, for example, by Western blot analysis.

Various immunoassays can be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between the target protein and its specific antibody. Examples of such techniques include ELISAs, radioimmunoassays (RIAs), and fluorescence activated cell sorting (FACS). Alternatively, a two-site, monoclonal-based immunoassay utilising monoclonal antibodies reactive to two non-interfering epitopes, or a competitive binding assay can be used (see, Maddox, D. E. et al. (1983) J. Exp. Med. 158:1211-1216). These and other assays are well known in the art (see, for example, Hampton, R. et al. (1990) *Serological Methods. A Laboratory Manual*, APS Press, St Paul, Minn., Section IV; Coligan, J. E. et al. (1997, and periodic supplements) *Current Protocols in Immunology*, Wiley & Sons, New York, N.Y.; Maddox, D. E. et al. (1983) *J. Exp. Med* 158:1211-1216).

The candidate modulators of the Wnt signalling pathways are further tested for their ability to promote or inhibit adult stem cell proliferation and/or lineage commitment. Typically, stem cells are cultured in the presence and absence of the candidate modulator and at least one indicator of proliferation and/or lineage commitment is subsequently monitored in the cells to determine whether proliferation and/or lineage commitment has been modulated in the cell culture exposed to the modulator. Alternatively, a population of stem cells can be co-cultured with educator cells, the stem cells or educator cells are exposed to the candidate modulator and at least one indicator of proliferation and/or lineage commitment monitor. Adult stem or progenitor cells derived from a variety of tissues can be used to screen the ability of candidate modulators to increase or decrease proliferation and/or lineage commitment. Examples include, but are not limited to, stem cells from cardiac muscle, skeletal muscle, adipose, skin, pancreatic, neural and liver tissue, stem cells from bone marrow, haematopoietic cells, myoblasts, hepatocytes, thymocytes, cardiomyocytes, and the like.

Various cell surface markers have been employed to identify adult stem cell populations including kit, Sca1, CD34, and CD45. The stem cells used to test the candidate modulators can, therefore, be c-kit$^+$, Sca1$^+$, CD34$^+$ or CD45$^+$ cells, or they may express a combination of two or more of these markers. In addition, the stem cells may express one or more of the above markers in combination with one or more of AC133, CD31, FLT1, FLK1, BRCP1 and Fzd1, 2, 3 or 4. Side population (or SP) cells, which are a type of adult stem cell that has been identified in skeletal and cardiac muscle, can be identified on the basis of Hoescht dye staining as is known in the art (see, for example, Gussoni, E., et al., (1999) *Nature* 401, 390-394; Jackson, K A, et al., (1999) *Proc Natl Acad Sci USA* 96, 14482-14486; Hierlihy, A M., et al., (2002) *FEBS Lett.* 530, 239-243).

In one embodiment of the present invention, the stem cells are derived from adult skeletal muscle tissue. In another embodiment, the stem cells are adult muscle-derived CD45$^+$ cells. In a further embodiment, the stem cells are adult muscle-derived CD45$^+$/Sca$^+$ cells.

Methods of maintaining stem cells in culture are known in the art (see, for example, Madlambayan, G. J., et al., (2001) *J. Hematother. Stem Cell Res.* 10,481-492; Hierlihy, A. M., et al., (2002) *FEBS Lett.* 530, 239-243; Asakura, A., et al., (2002) *J. Cell Biol.* 159, 123-134). The stem cells can be cultured alone (monoculture) or they can be co cultured with other (educator) cells. As an example, a co-culture could include a population of muscle-derived stem cells (or other stem cells) and myoblasts (educator cells) that are combined after isolation with or without a maintenance phase in separate culture. Alternatively, the two cell populations could be co-cultured as explants (e.g. mouse hindlimb muscle explant) without ever being isolated from their source tissue. It is understood and expected that stem cell cultures may also contain other cell populations if the stem cell and/or educator cell population is not-completely pure.

Additional steps may be included in the screening methods before, during, or after the culture period, such as steps to identify or isolate cell populations or otherwise contribute to the success of the assay. For example, growth factors or other compounds may be employed to isolate and expand the stem cell population. EGF and FGF have been used for this purpose with neural stem cells as described by Gritti et al (J. Neurosci. (1999) 19:3287-3297), and Bcl-2 has been used in the isolation of "muscle stem cell" populations (see U.S. Pat. No. 6,337,184). Other compounds useful in the isolation and/or maintenance of stem cell cultures include Shh, Ihh, BMP, BMP-antagonists, SCF and various cytokines.

The stem cells used in the screening assays can be primary cells or cultured stem cell lines isolated or derived from a normal adult mammal. Alternatively, the stem cells can be isolated or derived from a mammal carrying a mutation in one or more genes encoding a protein in the Wnt signalling pathways or a mammal expressing a reporter gene in a tissue specific locus. For example, the differentiation of resident muscle stem cells into myocytes in response to a modulator of the invention can be determined using cells isolated from heterozygous Myf5nLacZ knock-in mice. In these reporter mice, expression of LacZ faithfully recapitulates the expression pattern of the endogenous My5 gene, which is rapidly induced following myogenic commitment (Tajbakhsh and Buckingham, 1995, Development, 122:3765-3773). Expression of Myf5nLacZ in these cells thus indicates myogenic commitment in response to a candidate modulator.

Generally, a candidate modulator is tested over a range of concentrations, typically about a 1000-fold range, and a suitable exposure protocol can be readily established by one skilled in the art. When a co-culture is used, stem cell exposure to a candidate modulator can occur before, during and/or after the initial exposure of the stem cells to the educator cells. Alternatively, when the candidate modulator is a nucleic acid molecule or a polypeptide or peptide encoded by a nucleic acid molecule, the stem cells can be transfected with the nucleic acid molecule, or an expression vector comprising the nucleic acid molecule, using standard methods described herein and elsewhere, such that the candidate modulator is produced endogenously.

It is further contemplated that the stem cells may not be directly exposed to the candidate modulator. For example, an educator cell population or a third cell type can be directly exposed to the modulator and subsequently co-cultured with the stem cells. Alternatively, an educator cell population or a third cell type can be transfected with the nucleic acid molecule, or an expression vector comprising the nucleic acid molecule, that expresses the candidate modulator and the cells subsequently co-cultured with the stem cells. The stem cells can also be indirectly exposed by the addition of medium that has been conditioned by a cell population that has been exposed to a modulator, but which is not itself included in the co-culture. In addition, it is contemplated that the cells or explants of the assay may be exposed to a candidate modulator by incorporation or the modulator into a non-liquid medium of the culture, for example, a solid, gel or semi-solid growth support such as agar, a polymer scaffold, matrix or other construct.

Endpoints representative of stem cell proliferation and/or lineage commitment may be monitored qualitatively or quantitatively in the test and control stem cell populations. For example, qualitative or quantitative observations on changes in the gross morphology, histology, immunohistochemistry, total cell number, differentiated cell number or other endpoints may be made on the test and control cells or explants or sections thereof. Alternatively, the presence or absence of a specific cellular marker can be monitored. Cellular markers are typically lineage-specific proteins, the presence, absence or relative levels of which can be analyzed using a number of standard techniques including, for example, by histochemical techniques, immunological techniques, electrophoresis, Western blot analysis, FACS analysis, flow cytometry and the like. Alternatively, the presence, absence or relative levels of mRNA encoding the cellular marker protein can be determined, for example, using PCR techniques, microarray techniques, Northern blot analysis, the use of suitable oligonucleotide probes and the like.

Suitable line-specific cellular markers that can be monitored are known in the art. For example, lineage commitment of muscle-derived stem cells can be measured by examining the cells for expression of one or more myocyte marker proteins, such as myosin heavy chain, hypophosphorylated MyoD, myogenin, Myf5, Pax7 and troponin T. Lineage commitment of cardiac muscle stem cells, such as the cardiac side population (SP) cells present in the adult heart (Hierlihy, et al., A. M., et al., (2002) FEBS Lett. 530, 239-243), can be determined by monitoring the appearance of cardiomyocyte specific markers, such as connexin-43, MEF2C and/or myosin heavy chain. Lineage commitment of neural stem cells, derived as neurospheres or as SP cell fractions, can be determined by monitoring the expression of GFAP, MAP2 and/or β-III tubulin (see, for example, Hitoshi, S., et al., (2002) Genes & Dev. 16, 846-858) and lineage commitment of pancreatic stem cells can be determined by monitoring expression of PDX-1 and/or insulin. Terminal differentiation of committed precursors can also be determined by monitoring lineage specific markers such as those described above.

Applications

The present invention further provides for methods of inducing or inhibiting proliferation and/or lineage commitment of adult stem cells by contacting the cells, directly or indirectly, with one or more modulators of the Wnt signalling pathways. The modulators provided by the present invention can also be used to enhance the survival of stem cells or committed progenitor cells and to induce terminal differentiation in committed progenitor cells. The methods and modulators of the Wnt signalling pathways provided by the present invention have a number of applications. For example, the methods and modulators can be used in vitro to promote proliferation of adult stem cells and/or to promote or inhibit lineage commitment of stem cells wherein the cells are destined for further in vitro use, for example, for research-purposes. Compounds and methods that promote proliferation and/or promote or inhibit lineage commitment of stem cells also have potential applications in the development of new in vitro models for drug testing. The modulators of the invention that increase the survival of stem or progenitor cells are particularly useful in facilitating the in vitro culture and maintenance of these cells.

Alternatively, the methods and modulators can be used to promote the ex vivo proliferation of stem cells, and/or promote or inhibit the lineage commitment of these cells, and thereby provide a population of cells suitable for transplantation. Ex vivo expansion of stem cells has obvious therapeutic indications-for treating numerous disease conditions.

The methods and modulators of the present invention are particularly useful in vivo to promote the proliferation, and optionally the lineage commitment, of resident stem cells in adult tissues and thereby aid in the replacement or repair of damaged tissue. For example, it has been demonstrated that the resident population of stem cells in adult muscle tissue increases 10-fold following muscle injury. The methods and modulators, therefore, can be applied in injured tissue to promote proliferation and lineage commitment of these resident stem cells and thus accelerate the repair of the damaged tissue. Alternatively, the methods and modulators can be used to help alleviate degenerative diseases or disorders by stimulating proliferation, and optionally lineage commitment, of the quiescent resident stem cell population, thus replacing tissue damaged as a result of the disease or disorder.

Modulators of the Wnt signalling pathways, including Wnts 5a, 5b, 7a, 7b and sFRP 2 and 3, have been shown to be effective in modulating proliferation and lineage commitment of resident stem cell populations in adult muscle tissue.

Resident stem cell populations can be identified, for example, by Hoescht staining (for SP cells), by expression of $CD45^+$ and/or $Sca1^+$. CD45 and Sca1 are pan-hematopoietic markers that can be used to help identify resident stem cell populations in a variety of adult tissues.

In one embodiment of the present invention, the methods and modulators are used to induce proliferation and/or lineage commitment in adult muscle stem cells. In another embodiment, the methods and modulators are used to induce proliferation and/or lineage commitment in adult skeletal muscle stem cells. In a further embodiment, the methods and modulators are used to induce proliferation and/or lineage commitment of stem cells that are $CD45^+$. In still another embodiment, the methods and modulators are used to induce proliferation and/or lineage commitment of $CD45^+$ muscle stem cells. In a further embodiment, the methods involve the use of Wnt 5a, 5b, 7a, 7b polypeptides, active fragments or variants, or a combination thereof, as the modulator(s). In an alternate embodiment, the methods involve the use of one or more peptidomimetic of Wnt or one or more antibodies or antibody fragments that bind to and inhibit one or more sFRP as the modulator(s).

The modulators and methods of the invention may be used in addition to or concurrently with other cell treatments or therapies. In particular, the present invention contemplates methods in which a stem cell population, either in vitro or in vivo, is contacted first with an agent that stimulates proliferation and allows for expansion of the cell population as well as a modulator of the invention to enhance proliferation and/or to induce lineage commitment. The agent and modulator may provided to the cells concurrently, or they may be provided sequentially, for example, the cells may be contacted initially with an agent that induces proliferation and subsequently with one or more modulators of the invention to induce lineage commitment and enhance survival of the cells. Examples of agents that may be used in conjunction with the modulators of the present invention include, but are not limited to, cardiotrophin-1 (CT-1), Shh, Ihh, BMP, BMP-antagonists, SCF and various cytokines.

In one embodiment of the present invention, the method of inducing proliferation and/or lineage commitment of stem cells comprises contacting the cells with one or more modulator of the Wnt pathways and CT-1. In another embodiment, the method of inducing proliferation and subsequent lineage commitment of stem cells comprises contacting the cells with CT-1 and subsequently with one or more modulator of the Wnt pathways.

Therapeutic applications of the methods and modulators of the present invention, therefore, typically pertain to situations where there is a need to replace lost or damaged tissue, for example, after chemotherapy or radiation therapy, after muscle injury, to prevent muscle atrophy or loss of muscle mass, or in the treatment or management of diseases and disorders such as degenerative muscle disorders, cancers (including leukemias), degenerative liver diseases, including cirrhosis and hepatitis, diabetes, neurodegenerative disorders, such as Parkinson's disease and Alzheimer's disease, degenerative or ischemic cardiac disease, HIV infection and related complications, and neuromuscular diseases.

For therapeutic applications, the present invention further provides pharmaceutical compositions comprising one or more modulators of the Wnt signalling pathways and a pharmaceutically acceptable diluent or excipient. Pharmaceutical compositions and methods of preparing pharmaceutical compositions are known in the art and are described, for example, in "*Remington. The Science and Practice of Pharmacy*" (formerly "*Remingtons Pharmaceutical Sciences*"); Gennaro, A, Lippincott, Williams & Wilkins, Philidelphia, Pa. (2000).

Administration of the modulators or pharmaceutical compositions comprising the modulators may be via a number of routes depending upon whether local or systemic treatment is desired and upon the area to be treated. Typically, the modulators are administered locally to the area to be treated. Administration may be topical (including ophthalmic and to mucous membranes including vaginal and rectal delivery), pulmonary (e.g. by inhalation or insufflation of powders or aerosols, including by nebulizer), intratracheal, intranasal, epidermal and transdermal, oral or parenteral. Parenteral administration includes intravenous, intraarterial, subcutaneous, intraperitoneal or intramuscular injection or infusion, or intracranial, e.g. intrathecal or intraventricular, administration.

The modulators of the present invention may be delivered in combination with a pharmaceutically acceptable vehicle. Ideally, such a vehicle would enhance the stability and/or delivery properties. The present invention also provides for administration of the modulators using a suitable vehicle, such as a liposome, microparticle or microcapsule. In various embodiments of the-invention, the use of such vehicles may be beneficial in achieving sustained release of the active component.

When formulated for parenteral injection, the modulators are used in the form of a sterile solution containing other solutes, for example, enough saline or glucose to make the solution isotonic.

For administration by inhalation or insufflation, the modulators can be formulated into an aqueous or partially aqueous solution, which can then be utilised in the form of an aerosol. For topical use, the modulators can be formulated as dusting powders, creams or lotions in pharmaceutically acceptable vehicles, which are applied to affected portions of the skin.

The dosage requirements for the modulators of the present invention vary with the particular compositions employed, the route of administration and the particular subject being treated. Dosage requirements can be determined by standard clinical techniques known to a worker skilled in the art. Treatment will generally be initiated with small dosages less than the optimum dose of the compound. Thereafter the dosage is increased until the optimum effect under the circumstances is reached. In general, the modulators or pharmaceutical compositions comprising the modulators are administered at a concentration that will generally afford effective results without causing any harmful or deleterious side effects. Administration can be either as a single unit dose or, if desired, the dosage can be divided into convenient subunits that are ministered at suitable times throughout the day.

Gene Therapy

The present invention also contemplates administration of oligonucleotide modulators or nucleic acid molecules encoding modulators (which then express the encoded product in vivo) by various "gene therapy" methods known in the art. Gene therapy includes both ex vivo and in vivo techniques. Thus host cells can be genetically engineered ex vivo with an oligonucleotide modulator or a nucleic acid molecule encoding the modulator, with the engineered cells then being provided to a patient to be treated. Cell cultures may be formulated for administration to a patient, for example, by dissociating the cells (e.g., by mechanical dissociation) and intimately admixing the cell with a pharmaceutically acceptable carrier (e.g., phosphate buffered saline solution). Alternatively, cells may be cultured on a suitable biocompatible support and transplanted into a patient. The engineered cells are typically autologous so as to circumvent xenogeneic or allotypic rejection. Such ex vivo methods are well known in the art.

Alternatively, cells can be engineered in vivo by administration of the oligonucleotide or nucleic acid molecule using techniques known in the art. For example, oligonucleotides and other nucleic acid molecules can be administered by direct injection of a "naked" nucleic acid molecule (Felgner and Rhodes, (1991) *Nature* 349:351-352; U.S. Pat. No. 5,679,647) or a nucleic acid molecule formulated in a composition with one or more other agents which facilitate uptake of the nucleic acid molecule by the cell, such as saponins (see, for example, U.S. Pat. No. 5,739,118) or cationic polyamines (see, for example, U.S. Pat. No. 5,837,533); by microparticle bombardment (for example, through use of a "gene gun"; Biolistic, Dupont); by coating the nucleic acid molecule with lipids, cell-surface receptors or transfecting agents; by encapsulation of the nucleic acid molecule in liposomes, microparticles, or microcapsules; by administration of the nucleic acid molecule linked to a peptide which is known to enter the nucleus; or by administration of the nucleic acid molecule linked to a ligand subject to receptor-mediated endocytosis (see, for example, Wu and Wu, (1987) *J. Biol. Chem* 262: 4429-4432), which can be used to target cell types specifically expressing the receptors.

Alternatively, a nucleic acid-ligand complex can be formed in which the ligand comprises a fusogenic viral peptide to disrupt endosomes, allowing the nucleic acid to avoid lysosomal degradation; or the nucleic acid molecule can be targeted for cell specific uptake and expression in vivo by targeting a specific receptor (see, for example, International Patent Applications WO 92/06180, WO 92/22635, WO 92/20316, WO 93/14188 and WO 93/20221). In addition, an efficient method for the introduction, expression and accumulation of antisense oligonucleotides in the cell nucleus is described in U.S. Pat. No. 6,265,167, which allows the antisense oligonucleotide to hybridise to the sense mRNA in the nucleus, and thereby prevents the antisense oligonucleotide being either processed or transported into the cytoplasm. The present invention also contemplates the intracellular introduction of the nucleic acid molecule and-subsequent incorporation within host cell DNA for expression by homologous recombination (see, for example, Koller and Smithies (1989) *Proc. Natl. Acad. Sci. USA* 86:8932-8935; Zijlstra et al. (1989) *Nature* 342:435-438).

The polynucleotide can also be incorporated into a suitable expression vector. A number of vectors suitable for gene therapy applications are known in the art (see, for example, Viral Vectors: Basic Science and Gene Therapy, Eaton Publishing Co. (2000)).

The expression vector may be a plasmid vector. Methods of generating and purifying plasmid DNA are rapid and straightforward. In addition, plasmid DNA typically does not integrate into the genome of the host cell, but is maintained in an episomal location as a discrete entity eliminating genotoxicity issues that chromosomal integration may raise.

A variety of plasmids are now readily available commercially and include those derived from *Escherichia coli* and *Bacillus subtilis*, with many being designed particularly for use in mammalian systems. Examples of plasmids that may be used in the present invention include, but are not limited to, the eukaryotic expression vectors pRc/CMV (Invitrogen), pCR2.1 (Invitrogen), pAd/CMV and pAd/TR5/GFPq (Massie et al., (1998) Cytotechnology 28:53-64). In an exemplary embodiment, the plasmid is pRc/CMV, pRc/CMV2 (Invitrogen), pAdCMV5 (IRB-NRC), pcDNA3 (Invitrogen), pAdMLP5 (IRB-NRC), or PVAX Invitrogen).

Alternatively, the expression vector can be a viral-based vector. Examples of viral-based vectors include, but are not limited to, those derived from replication deficient retrovirus, lentivirus, adenovirus and adeno-associated virus. Retrovirus vectors and adeno-associated virus vectors are currently the recombinant gene delivery system of choice for the transfer of exogenous oligonucleotides or genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. Retroviruses, from which retroviral vectors may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumour virus. Specific retroviruses include pLJ, pZIP, pWE and pEM, which are well known to those skilled in the art.

The oligonucleotide or nucleic acid sequence encoding the modulator is usually incorporated into the vector under the control of a suitable promoter that allows for expression of the oligonucleotide or nucleic acid in vivo. Suitable promoters which may be employed include, but are not limited to, adenoviral promoters, such as the adenoviral major late promoter, the EIA promoter, the major late promoter (MLP) and associated leader sequences or the E3 promoter, the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter, human globin promoters; viral thymidine kinase promoters, such as the Herpes Simplex thymidine kinase promoter; retroviral LTR; the histone, pol III, and β-actin promoters; B19 parvovirus promoter, the SV40 promoter, and human growth hormone promoters. The promoter also may be the native promoter for the gene of interest. The selection of a suitable promoter will be dependent on the vector, the host cell and the encoded protein and is considered to be within the ordinary skills of a worker in the art.

The development of specialised cell lines (termed "packaging cells") which produce only replication-defective retroviruses has increased the utility of retroviruses for gene therapy, and defective retroviruses are well characterised for use in gene transfer for gene therapy purposes (for a review see Miller, A. D. (1990) Blood 76:271). Thus, recombinant retrovirus can be constructed in which part of the retroviral coding sequence (gag, pol, env) has been replaced by nucleic acid molecule of the invention and renders the retrovirus replication defective. The replication defective retrovirus is then packaged into virions that can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M et al. (eds.), J. Wiley & Sons, (1989), Sections 9.10-9.14 and other standard laboratory manuals. Examples of suitable packaging virus lines for preparing both ecotropic and amphotropic retroviral systems include Crip, Cre, 2 and Am. Other examples of packaging cells include, but are not limited to, the PE501, PA317, ψ-2, ψ-AM, PA12, T19-14×VT-19-17-H2, ψCRE, ψCRIP, GP+E-86, GP+envAm12, and DAN cell lines as described in Miller, Human Gene Therapy, Vol. 1, pgs. 5-14 (1990).

Furthermore, it has been shown that it is possible to limit the infection spectrum of retroviruses and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al. (1989) PNAS 86:9079-9083; Julan et al. (1992) J. GenVirol 73:3251-3255; and Goud et al. (1983) Virology 163:251-254); or coupling cell surface receptor ligands to the viral env proteins (Neda et al. (1991) J Biol Chem 266:14143-14146). Couplings i be in the form of the chemical cross-linking with a protein or other variety (for example, lactose to convert the env protein to an asialoglycoprotein), as well as by generating fusion proteins (for example, single-chain antibody/env fusion proteins). This technique, while useful to limit or otherwise direct the infection to certain tissue types, can also be used to convert an ecotropic vector in to an amphotropic vector.

Moreover, use of retroviral gene delivery can be further enhanced by the use of tissue- or cell-specific transcriptional regulatory sequences which control expression of the nucleic acid molecules of the invention contained in the vector.

Another viral vector useful in gene therapy techniques is an adenovirus-derived vector. The genome of an adenovirus can be manipulated such that it encodes and expresses a gene product of interest but is inactivated in terms of its ability to replicate in a normal lytic viral life cycle. See for example Berkner et al. (1988) BioTechniques 6:616; Rosenfeld et al. (1991) Science 252:431-434; and Rosenfeld et al. (1992) Cell 68:143-155. Suitable adenoviral vectors derived from the adenovirus strain Ad type 5 dl324 or other strains of adenovirus (for example, Ad2, Ad3, Ad7 etc.) are well known to those skilled in the art Recombinant adenoviruses can be advantageous in certain circumstances in that they can be used to infect a wide variety of cell types, including peripheral nerve cells. Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (for example, retroviral DNA). Moreover, the carrying capacity of the adenoviral genome for foreign DNA is large (up to 8 kilobases) relative to other gene delivery vectors (Berkner et al. cited supra; Haj-Ahmand and Graham (986) J. Virol. 57:267). Most replication-defective adenoviral vectors currently in use and contemplated by the present invention are deleted for all or parts of the viral E2 and E3 genes but retain as much as 80% of the adenoviral genetic material (see, e.g., Jones et al. (1979) Cell 16:683; Berkner et al., supra; and Graham et al. in Methods in Molecular Biology, Et J. Murray, Ed. (Humana, Clifton, N.J., 1991) vol. 7. pp. 109-127).

Generation and propagation of replication-defective human adenovirus vectors requires a unique helper cell line. Helper cell lines may be derived from human cells such as human embryonic kidney cells, muscle cells, hematopoietic cells or other human embryonic mesenchymal or epithelial cells. Alternatively, the helper cells may be derived from the cells of other mammalian species &at are permissive for human adenovirus, i.e. that provide, in trans, a sequence necessary to allow for replication of a replication-deficient virus. Such cells include, for example, 293 cells, Vero cells or other monkey embryonic mesenchymal or epithelial cells. The use of non-human adenovirus vectors, such as porcine or bovine adenovirus vectors is also contemplated. Selection of an appropriate viral vector and helper cell line is within the ordinary skills of a worker in the art.

In one embodiment of the present invention, the gene therapy vector is an adenovirus derived vector. In another embodiment, the gene therapy vector is an adenovirus derived vector comprising a nucleic acid sequence encoding one or more Wnt protein.

Kits

The present invention additionally provides for therapeutic kits containing one or more modulators of the Wnt signalling pathways in pharmaceutical compositions. Individual components of the kit would be packaged in separate containers and, associated with such containers, can be a notice in the form prescribed by a governmental agency regulating the manufacture, use or sale of pharmaceuticals or biological products, which notice reflects approval by the agency of manufacture, use or sale for human administration.

When the components of the kit are provided in one or more liquid solutions, the liquid solution can be an aqueous solution, for example a sterile aqueous solution. In this case the container means may itself be an inhalant, syringe, pipette, eye dropper, or other such like apparatus, from which the composition may be administered to a patient.

The components of the kit may also be provided in dried or lyophilised form and the kit can additionally contain a suitable solvent for reconstitution of the lyophilised components.

Irrespective of the number or type of containers, the kits of the invention also may comprise an instrument for assisting with the administration of the composition to a patient. Such an instrument may be an inhalant, syringe, pipette, forceps, measured spoon, eye dropper or any such medically approved delivery vehicle.

The stem cells as referred to herein may be present in a subject during development, for example, but not to be limiting, from neonate to adult or any time in between. In an embodiment, which is not meant to be limiting in any manner, the stem cells may be present in a subject immediately after birth, or at about 1 day, 2 days, 5 days, 1 week, 5 weeks, 10 weeks, 25 weeks, 1 year, 2 years, 5 years, 10 years, 20 years, 40 years, 50 years, 60 years, 90 years, or any time therein between. It is also possible to isolate and/or purify stem cells from a suitable subject by any method known in the prior art. Such methods of isolation and/or purification are meant to be encompassed by the present invention. In the event that stem cells are isolated from a subject, preferably the subject is living. However, it may be possible to obtain stem cells from subjects that are recently deceased.

The present invention also contemplates methods of increasing proliferation, differentiation or both proliferation and differentiation of stem cells in a subject to increase a) the number of muscle cells in one or more muscles in a subject, b) the muscle mass of one or more muscles in a subject c) the strength of one or more muscles in a subject. In a preferred embodiment, the subject is a humans. However, it is also contemplated that the stem cells may be employed to increase muscle mass in other subjects.

The methods of the present application as described herein may be practiced in-vivo or in vitro. For example, but not wishing to be considered limiting in any manner, the present invention contemplates one or more steps of isolating stem cells from a subject, purifying stem cells, culturing stem cells, treating stem cells with one or more activators or inhibitors of proliferation, differentiation or both proliferation and differentiation, transforming stem cells with one or more nucleotide constructs, for example that produce one or more activators or inhibitors or proliferation, differentiation or both proliferation and differentiation, or a combination thereof.

The present invention also contemplates methods and compositions comprising one or more small molecules, such as, but not limited to lithium chloride that may be employed to increase proliferation, differentiation or both proliferation and differentiation of stem cells in a subject. For example, but not wishing to be considered limiting in any manner, there is provided a method of increasing proliferation, differentiation or both proliferation and differentiation of muscle stem cells in a subject comprising, administering a composition comprising lithium chloride to the subject.

The composition may be administered in one or more doses over the course of one or more days, for example, about one day to 30 days, about one day to about 14 days or any other suitable time period as required. A therapeutic dose may be easily determined by a person of skill in the art. For example, but not wishing to be limiting in any manner, lithium cloride may be present in the composition in an amount of between about 0.001 mg/kg (based on the weight of the subject) to about 200 mg/kg, preferably about 0.01 mg/kg to about 20 mg/kg, more preferably about 1 mg/kg to about 10 mg/kg, more preferably about 2 mg/kg. The dosage amount may vary depending on the dosage route contemplated, the particular subject, the health of the subject, etc as would be evident to a person of skill in the art.

It is also contemplated the compositions comprising lithium chloride may comprise other compounds for example, but not limited to one or more modulators of wnt signaling as defined herein.

In an embodiment, the composition is administered to a subject that exhibits muscle degeneration or muscle wasting, for example, but not limited to as a result of a disease or non-disease. In a specific example, which is not meant to be limiting in any manner, the composition may be administered to a subject that has or exhibits a disease such as cancer, aids or the like. In still an alternate embodiment, the composition may be administered to a subject to increase the number of muscle cells in a subject and/or to increase the strength, size, or or both of one or more muscles in the subject. In this regard, but without wishing to be limiting or bound by theory, the methods and compositions as defined herein throughout may be employed to prevent and/or treat muscle degeneration, wasting, or the like associated with one one or more diseases such as cancer, aids, diabetes, for example, type 2 diabetes, muscular degenerative diseases and the like. Further, the methods and compositions as defined throughout herein may be employed to prevent and/or treat muscle degeneration or muscle wasting as a result from one or more non-disease processes, for example, but not limited to muscle atrophy for example, but not limited to as a result of non-use of one or more muscles. The method may also be employed to prevent and/or treat incontinence. Also, the methods and compositions as defined throughout herein may be employed to increase the number of muscle cells in a subject, to increase the size of one or more muscles in a subject, to increase the strength of one or more muscles in a subject, or any combination thereof.

The compositions as defined herein may be administered by any means known in the art, for example, but not limited to, orally, or by injection, for example, but not limited to intravenous, intraperitoneal (IP), intramuscular, subcutaneous and the like. In an embodiment in which lithium is present in the composition, preferably it is administered by intraperitoneal (IP) or intramuscular injection, more preferably IP injection. However, other routes of administering the compostion are also contemplated.

The composition as defined herein throughout may be formulated into any appropriate dosage form, for example, tablet, solution, suspension, emulsion, microemulsion or the like, as would be known in the art.

Figure 8A:
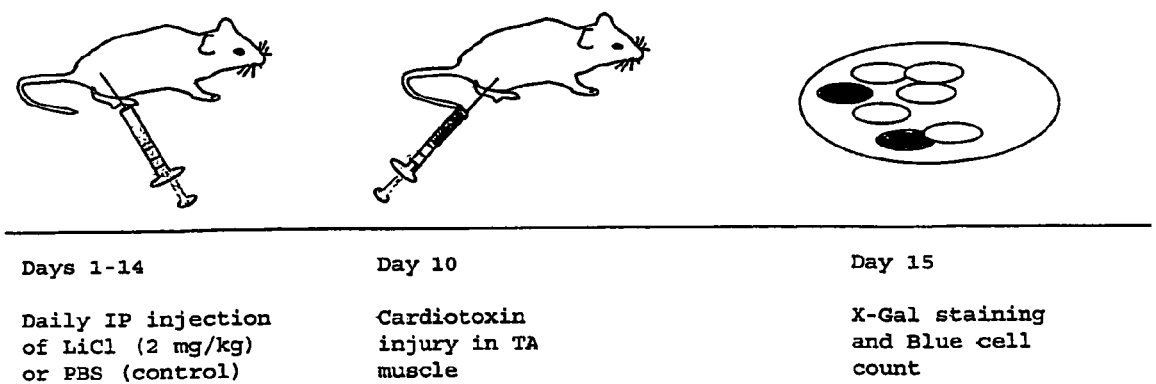
(FIG. 8A) Experimental design flow chart. Myf5nLacZ mice are treated with daily IP injections of LiCl (2 mg/Kg/day) for a period of 14 days. At day 10, muscle regeneration is induced in the TA muscle by cardiotoxin injection. Four days later, animals are sacrificed and total mononuclear cells are isolated from the TAs, plated and stained 24 hours later for B-galactosidase.
Figure 8B:
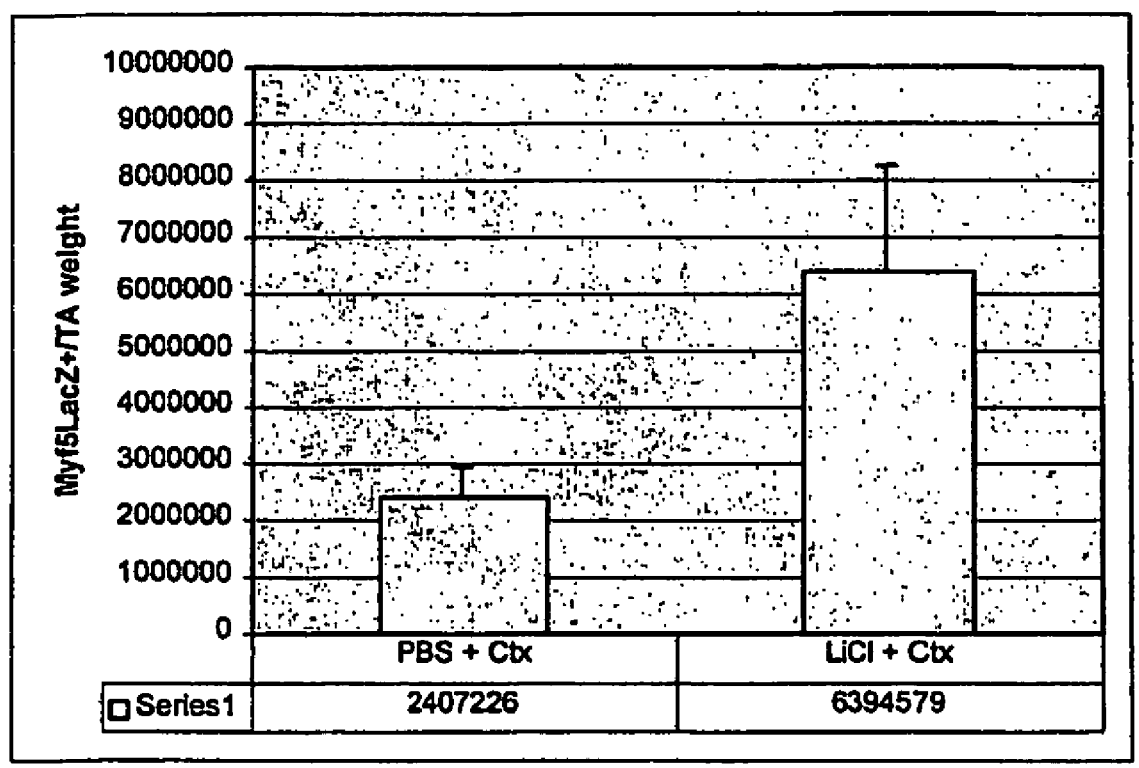
(FIG. 8B) Results indicate that the proportion of B-Gal positive cells (myogenic cells) is almost more than doubled in the LiCl treated animals versus the PBS injected control

Referring now to FIG. 8, there is shown the experimental design and results of experiments demonstrating an increase in cells committed to myogenesis in response to lithium treatment in vivo. FIG. 8A shows the experimental design flow chart wherein Myf5nLacZ mice are treated with daily IP injections of LiCl (2 mg/Kg/day) for a period of 14 days. At day 10, muscle regeneration is induced in the TA muscle by cardiotoxin injection. Four days later, animals are sacrificed and total mononuclear cells are isolated from the TAs, plated and stained 24 hours later for B-galactosidase. FIG. 8B shows results indicating that the proportion of B-Gal positive cells (myogenic cells) is almost doubled in the LiCl treated animals versus the PBS injected control animals.

To gain a better understanding of the invention described herein, the following examples are set fort. It should be understood that these examples are for illustrative purposes only. Therefore, they should not limit the scope of this invention in any way.

The above description is not intended to limit the claimed invention in any manner, furthermore, the discussed combination of features might not be absolutely necessary for the inventive solution.

EXAMPLES

Example 1

Wnt Signalling Activates the Myogenic Recruitment of CD45+ Adult Stem Cells During Muscle Regeneration Materials and Methods Cell Sorting Mononuclear cells were obtained from hind-limb muscles of β-actin-EGFP transgenic mice (Hajantonakis, 1998, Mech Dev 76,79-90), or Myf5nLacZ transgenic mice (Tajbakhsh, 1995, Development 125,4155-4162). Muscle cells were recovered as described previously (Megeney, 1996, Genes Dev 10, 1173-1183). Mononuclear cells were washed twice with DMEM supplemented with 5% FBS, and suspended at a concentration of $2-3\times10^6$ cells/ml. Staining was performed for 30-45 min on ice using the antibodies: CD45-APC, clone 30-F11 or CD45.2-FITC (clone 104), Sca1-PE, clone D7 (BD Pharmingen). Alternatively, CD45-biotin, clone 30-F11, was used followed by 10-min incubation with Streptavidin Tri-Color Conjugate (Caltag Labs). Primary antibodies were diluted at 1:200, and Streptavidin Tri-Color Conjugate was diluted 1:1000. After two washes with DMEM at 4° C., cells were separated on a MoFlo cytometer (DakoCytomation), equipped with 3 lasers. Sort gates were strictly defined based on isotype control stained cells and single antibody staining. Dead cells and debris were excluded by gating on forward and side scatter profiles. Sorting was performed using single cell mode to achieve the highest possible purity. The purity of sorted populations was routinely >98%.

For direct analysis of sorted cell populations, cells were washed and suspended in phosphate-buffered saline (PBS), and cytospun onto silanized slides (DAKO). X-gal staining was performed as described previously (Kablar, 1997, Development 124, 4729-4738).

Cell Culture and Stable Cell Lines

Primary myoblasts were isolated from hind limb muscle of 3-week old Balb/c mice, and maintained in HAM's F-10 medium (Invitrogen) supplemented with 20% FBS, and 2.5 ng/ml bFGF (Invitrogen). Single muscle fibers were prepared from the extensor digitorum longus muscle as described previously (Rosenblatt, 1995). AtT-20, BOSC 23, C3H10T1/2, and Cos1 cells were obtained from the ATCC and maintained in DMEM supplemented with 10% FBS. Stable cell lines expressing HA-Wnt proteins were derived as described previously (Shimizu, 1997, Cell Growth Differ 8, 1349-1358). Expression of HA-Wnts was confirmed by Western Blot analysis with anti-HA antibody (HA-7, Sigma).

Co-Culture Experiments and Immunohistochemistry

For co-culture experiments, primary myoblasts or Wnt-expressing cells were mixed with purified $CD45^+$:$Sca1^+$ cells at a ratio of 1:1, and seeded on Collagen-coated 2-well Permanox Chamber Slides (Lab-Tek). The density was $2\times10^4$ cells/chamber for co-culture in growth conditions, and $4\times10^4$ cells/chamber for differentiation experiments. The co-cultures were maintained in HAM's F-10 medium, supplemented with 20% FBS, for 3 days, and switched to DMEM (5% Horse Serum for differentiation experiments. For the $Li^{2+}$ or Shh conversion experiments, LiCl (Sigma) at 10 mM, or Shh-N(R&D Systems) at 10 or 100 ng/mL was added to the differentiation media For immunohistochemical analysis, cells were fixed with 2% PFA for 15 min at room tem permeabilized with 0.05% Triton X-100 for 15 min, blocked with 1% BSA/5% HS in PBS, and stained for 2 h, room temperature, with antibodies: MyoD, clone 5.8A (BD Pharmingen); Myosin Heavy Chain, clone MF-20 (Developmental Studies Hybridoma Bank (DSHB)); Pax7 (DSHB); or β-catenin (BD Transduction Laboratories). Fluoroscein or Rhodamine conjugated antibodies (Chemicon) were used for secondary detection. Cover slides were mounted and analyzed using a Zeiss Axioscop fluorescent microscope.

RT-PCR, Cloning, and Sequencing.

Total RNA was extracted using RNAeasy kits (Qiagen), according to manufacturer's instructions. For analysis of Frizzled gene expression, RT-PCR was performed with fully degenerate primers corresponding to conserved frizzled sequences YPERPIIF and WWVILSLTW, as previously described (Malik, 2000, Biochem J 349 Pt 3, 829-834). The products were cloned into the TOPO-PCRII vector (Invitrogen) and sequenced. RT-PCR analysis of Wnt mRNAs was performed using the GeneAmp PCR Core kit (Perkin-Elmer). The following primers were used: Wnt1 (5'-acgtacagtggccgc-ctg-3' (SEQ ID NO: 1); 5'-acgcgcgtgtgcgtgcagtt-3' (SEQ ID NO: 2); 203 bp); Wnt3a (5' -ggagatggtggtagagaaa-3' (SEQ ID NO: 3); 5'atagacacgtgtgcactc-3' (SEQ ID NO: 4); 322 bp); Wnt4 (5'-agcccccgttcgtgcctgcggtcc-3' (SEQ ID NO: 5); 5'-actccacccgcatgtgtgtca-3' (SEQ ID NO: 6); 607 bp); Wnt5a (5'-aatggcmggccacgtmt-3' (SEQ ID NO: 7); 5'-tggattcgttc-ccm-3' (SEQ ID NO: 8); 541 bp); Wnt5b (5'-agtgcagagaccg-gagatgttc-3' (SEQ ID NO: 9); 5'-ggcaaagttcttctcacgc-3' (SEQ ID NO: 10); 459 bp); Wnt7a (5'-agcgcggcgctgcctgggcc-3' (SEQ ID NO: 11); 5'-cttcagaaaggtgggccgcttgttt-3' (SEQ ID NO: 12); 752 bp); Wnt7b (5' -ccgcacctcgccggggggccgac-3' (SEQ ID NO: 13); 5'-gtcggccccccggcgaggtgcgg-3' (SEQ ID NO: 14); 180 bp); Wnt10a (5'-aaagtcccctacgagagccc-3' (SEQ ID NO: 15), 5' -cagcttccgacggaaagctt-3' (SEQ ID NO: 16)), Wnt10b (5'-cggctgccgcaccacagcgc-3' (SEQ ID NO: 17), 5'-cagcttggctctaagccggt-3' (SEQ ID NO: 18)), sFRP 1 (5'-cgc-ccgtctgtctggaccg-3' (SEQ ID NO: 19); 5'-ctcgcttgcaca-gagatgt-3' (SEQ ID NO: 20), 257 bp); sFRP2 (5' -ttcggccagc-ccgactictcc- 3' (SEQ ID NO: 21); 5'-taggtcgtcgagacagacagggg-3' (SEQ ID NO: 22), 234 bp); sFRP3 (5'-ammcctatggattcaagtactg-3' (SEQ ID NO: 23); 5' -ttgacmcttaccaagccgatcctt-3' (SEQ ID NO: 24); 396 bp);

sFRP4 (5'-tggatagacatcacaccagatat-3' (SEQ ID NO: 25); 5'-cctgaagcctctcttccca-3' (SEQ ID NO: 26), 423 bp).

Cardiotoxin-Induced Regeneration 5 to 8 week-old mice were anaesthetised with Halothane gas. 25 μl of 10 μM cardiotoxin (Latoxan) was injected directly into the TA muscle, using a 29 G 1/2 insulin syringe. For cell proliferation assays, 0.3 mg/kg of 5-bromo-deoxyuridine (BrdU, Sigma) was injected intraperitoneally 90 minutes prior to sacrificing animals. Cells that had incorporated BrdU were detected by flow cytometry using a FITC conjugated anti-BrdU antibody (ED Pharmingen). For sFRP experiments, 100 ng of recombinant sFRP 2 and 3 (R&D Systems) were injected into regenerating TA muscle. Control animals received injections of equal volumes of PBS. For analysis of total TA cell populations, $1 \times 10^4$ mononuclear cells were plated on collagen-coated chamber slides overnight and then stained with anti-Desmin antibody (DAKO) at 1:200. Donkey anti-mouse FITC (Chemicon) at 1:500 was used for secondary detection.

Western Blot Analyses

Uninjured and regenerating TA muscles were flash frozen in liquid nitrogen, crushed, and lysed in extraction buffer (50 mM Tris-HCl pH 7.4, 0.1% Triton X-100, 5 mM EDTA, 250 mM NaCl, 50 mM NaF, protease inhibitors (Complet, Roche). The extracts were normalized for protein content using Bio-Rad dye. 50 μg of lysate was separated by sodium dodecyl sulfate-polyacrylamide gel electrophoresis (SDS-PAGE), and transferred onto nitrocellulose filters. Filters were probed with antibodies to Wnt5a, 1:200 (AF645, R&D Sysns); β-catenin, 1:250 (BD Transduction Laboratories), α-tubulin, 1:2000 (T 9026, Sigma). Secondary detection was performed with horseradish peroxidase-conjugated antibodies (BioRad). Protein expression was visualized using the ECL Plus kit (Amersham).

Affymetrix Expression Profiling of Regenerating Muscle

Gene expression profiling and data analysis of regenerating mouse gastrocnemius muscle was performed at the CNMC Research Center, as described by (Zhao, 2002, J Biol Chem 277, 30091-30101). Briefly, gastrocnemius muscles were injected with 100 μl of 10 mM cardiotoxin (ctx) (Calbiochem).RNA was prepared from 4 individual muscles at time 0 (no injection), 12 h, 1 day, 2 days and 10 days after ctx injection. Biotin-labelled cRNA was obtained for each replicate, fragmented, and hybridized to Murine Genome U74A version 1 chips (Affymetrix). Primary data and comparison analysis was done using Affymetrix Microarray Suite 4.0 as described previously (Chen, 2000, J Cell Biol 151, 1321-1336).

Results

Myogenic Commitment of $CD45^+:Sca1^+$ Cells During Muscle Regeneration

Cells expressing the pan-hematopoietic marker CD45 and the stem cell marker Stem Cell Antigen-1 (Sca1) were purified from uninjured tibialis anterior (CA) muscle and at varying time-points after cardiotoxin (ctx) induced regeneration (FIG. 1A). The proportion of CD45 and Sca1 expressing cells increased by an average of 10-fold during regeneration (n=6) (FIG. 1A). Interestingly, selective incorporation of BrdU into $CD45-:Sca1^+$ (60% of BrdU+cells) and $CD45^+:Sca1^+$ cells (18% of BrdU+cells) at 4 days postfix injection suggested that these cells undergo extensive proliferation during regeneration FIG. 1B). These observations demonstrate that muscle cells expressing CD45 and Sca1 are activated and proliferate in response to muscle damage.

To specifically identify cells that had entered the myogenic program, muscle regeneration was induced in heterozygous Myf5nLacZ knock-in animals, in which the bacterial LacZ gene is expressed from the Myf5 gene locus. In these reporter mice, expression of LacZ faithfully recapitulates the expression pattern of the endogenous Myf5 gene and is rapidly induced following myogenic commitment (Tajbakhsh, 1995, Development 121, 4077-4083). $CD45^+:Sca1^+$ cells were fractionated from uninjured and regenerating muscle 4 days after ctx injection and immediately used to prepare cytospins.

Importantly, $CD45^+:Sca1^+$ and $CD45^-:Sca1^+$ cells purified from uninjured muscle were always Myf5nLacZ negative and never gave rise to determined muscle cells in vitro (n=6). (not shown). Strikingly however, $7.2+1-2.6\%$ of $CD45^+:Sca1^{high}$ (n=6) (see FIG. 1A) and $3.8+/-1.8\%$ of $CD45^-:Sca1^+$ (n=3) cells from regenerating muscles 4 days post-injury co-expressed Myf5nLacZ (FIG. 1C). A similar proportion of $CD45^+:Sca1^{high}$ cells purified from regenerating muscle (4 day post injury) expressed MyoD (FIG. 1D), the muscle specific intermediate filament protein, Desmin (FIG. 1D) and the satellite cell specific Pax7 protein (data not shown). Furthermore, $CD45^+:Sca1^+$ cells fractionated from regenerating muscle differentiated to Myosin Heavy Chain (MHC) expressing myocytes following culture in differentiation medium (FIG. 1D). The complete absence of Myf5nLacZ expression in $CD45^+:Sca1^-$ cells isolated throughout regeneration indicated the specific activation of myogenesis in $CD45^+:Sca1^+$ and $CD45^+:Sca1^+$ cells. Similar results were obtained in experiments on cells that had been sorted twice.

The impact of ctx on the numbers of myogenic progenitors present within the injured muscle was also examined (see also, Asakura, 2002, J Cell Biol 159, 123-134). Interestingly, 18 hours post-ctx injection, the number of Myf5nLacZ+ cells was reduced by approximately 30-fold relative to uninjured muscle ($1.18 \times 10^3 \pm 1 \times 10^3$ compared to $4.1 \times 10^4 \pm 1.6 \times 10^4$ Myf5nLacZ+cells/g tissue) (FIG. 1E). This observation was not due to ctx-induced My5 promoter silencing since colony-forming assays of whole muscle cells produced a similar decline in $MyoD^+$ and $Desmin^+$ myogenic cells 18 hours after ctx injection.

To determine the relative myogenic contribution of $CD45^+$ and $Sca-1^+$ cells during regeneration the numbers of Myf5nLacZ expressing cells derived from the various muscle fractions was calculated. The analysis (n>3 for each time point) revealed that $CD45^+:Sca1^{high}$; $CD45^-:Sca1^+$; and $CD45^+:Sca1^-$ gave rise to an average of $1.54 \times 10^5$, $3.9 \times 10$ and $2 \times 10^3$ Myf5LacZ+ cells/g tissue respectively 4 days post-ctx injection (FIG. 1F). These numbers represent average values compiled from independent experiments in which fractionated populations from Myf5nLacZ muscle were used to prepare cytospins. Notably, committed myogenic progenitors ($CD45^-:Sca1^-$) accounted for $6.0 \times 10^6$ Myf5nLacZ+ cells/g tissue by 4 days post-injury. The apparent toxicity of ctx on satellite cells thus raises the question of whether the resident satellite cell population does indeed represent the only source of myogenic progenitors following ctx-induced muscle injury.

Taken together, these experiments document the capacity for muscle-derived CD45+ and Sca1+ cells to undergo myogenic specification in response to muscle damage. Importantly, his observation demonstrates that non-satellite cell derived progenitors participate in normal repair processes.

Figure 2:
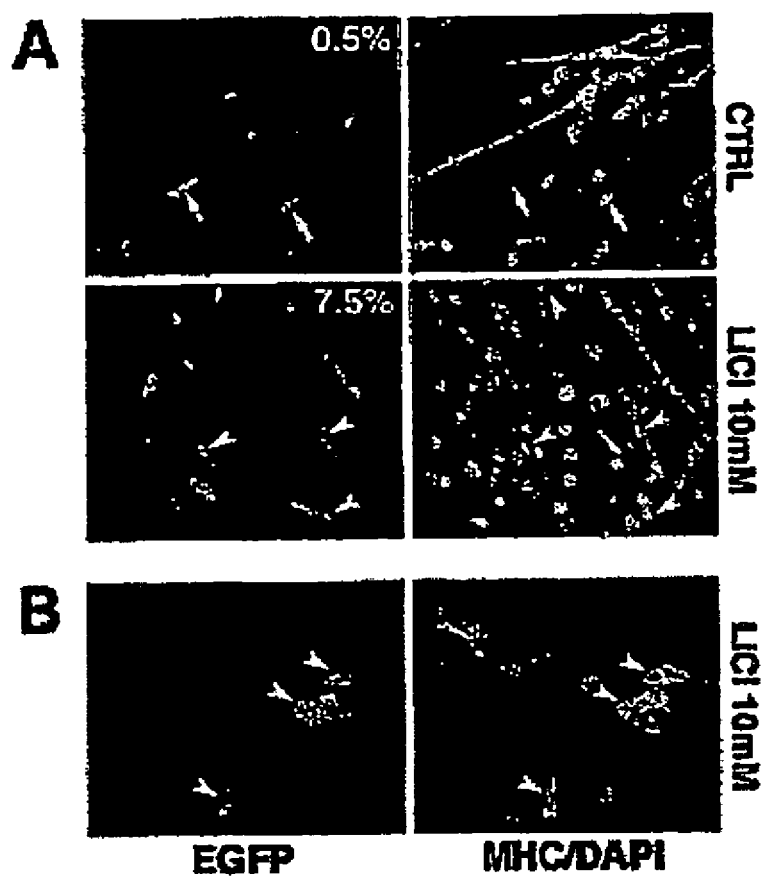
FIG. 2 depicts myogenic commitment of CD45$^+$:Sca1$^+$ cells induced by co-culture with myoblasts or exposure to Lithium (A) EGEP-expressing CD45$^+$:Sca1$^{high}$ cells co-cultured with primary myoblasts gave rise to mononuclear Myosin Heavy Chain (MHC) expressing myocytes at a frequency of 0.5%. In co-cultures supplemented with 10 mM LiCl, 7.5% of EGFP+:CD45$^+$:Sca1$^{high}$ cells formed MHC+ myocytes (arrowheads). Arrows indicate EGFP+, non-myogenic cells. (B) CD45$^+$:Sca1$^{high}$ cells cultivated alone in differentiation medium supplemented with 10 mM LiCl formed mononuclear, MHC expressing myocytes (arrowheads).

Myogenic Commitment of CD45+:Sca1+ Cells Induced by Co-Culture with Myoblasts or Exposure to Lithium As stated previously, CD45+:Sca1+ cells purified from uninjured skeletal muscle do not form myogenic cells spontaneously (see also, Asakura, 2002, J Cell Biol 159, 123-134; McKinney-Freeman, 2002, Proc Natl Acad Sci USA 99, 1341-1346). However, in co-culture with primary myoblasts, 0.5±0.03% of input CD45+:Sca1+ muscle cells from EGFP transgenic mice formed mononuclear, MHC-expressing myocytes (FIG. 2A, control). This frequency of myogenic differentiation is an underestimate of the actual efficiency since EGFP is only detectable in up to 50% of muscle cells from these transgenic mice and the plating efficiency of CD45+:Sca1+ cells is low. The complete absence of myogenic cells observed in CD45+:Sca-1+ fractions cultured alone (n=6) ruled out any possible contamination of co-cultures with myoblasts due to sorting.

The Wnt-signalling pathways is activated by Lithium through inhibition GSK-3β, and stabilization of β-catenin in treated cells (Hedgepeth, 1997, Dev Biol 185, 82-91). Therefore, to investigate whether the Wnt-signalling pathways was involved in this phenomenon, co-cultures of CD45+:Sca1+ muscle cells and primary myoblasts were exposed to 10 mM LiCl. Strikingly, treatment of co-cultures with 10 mM LiCl, resulted in a 15-fold increase in the frequency of GFP+, myosin heavy chain MC) expressing myocytes to 7.5% (n=3) of input cells (FIG. 2A). Moreover, CD45+:Sca1+ cells cultured without myoblasts in LiCl-containing differentiation medium underwent myogenic differentiation as evidenced by MHC expression (FIG. 2B). However, in growth conditions, LiCl induced rapid death of myogenic cells within 48 h precluding further analysis of these cultures. In summary, these results suggested that activation of the Wnt-signaling pathways induced myogenic specification of CD45+:Sca1+ cells isolated from adult skeletal muscle.

The ability of Sonic Hedgehog (Shh) to stimulate myogenesis in CD45+:Sca1+ muscle cells was also tested Addition of recombinant Shh at 10 or 100 ng/ml to CD45+:Sca1+ cells alone or in co-culture with myoblasts did not influence their myogenic differentiation efficiency. However, a 3-4 fold increase in CD45+:Sca1+ cell survival was observed following exposure to 100 ng/ml Shh.

Induction of Wnt and sFRP Expression in Regenerating Muscle

Figure 3:
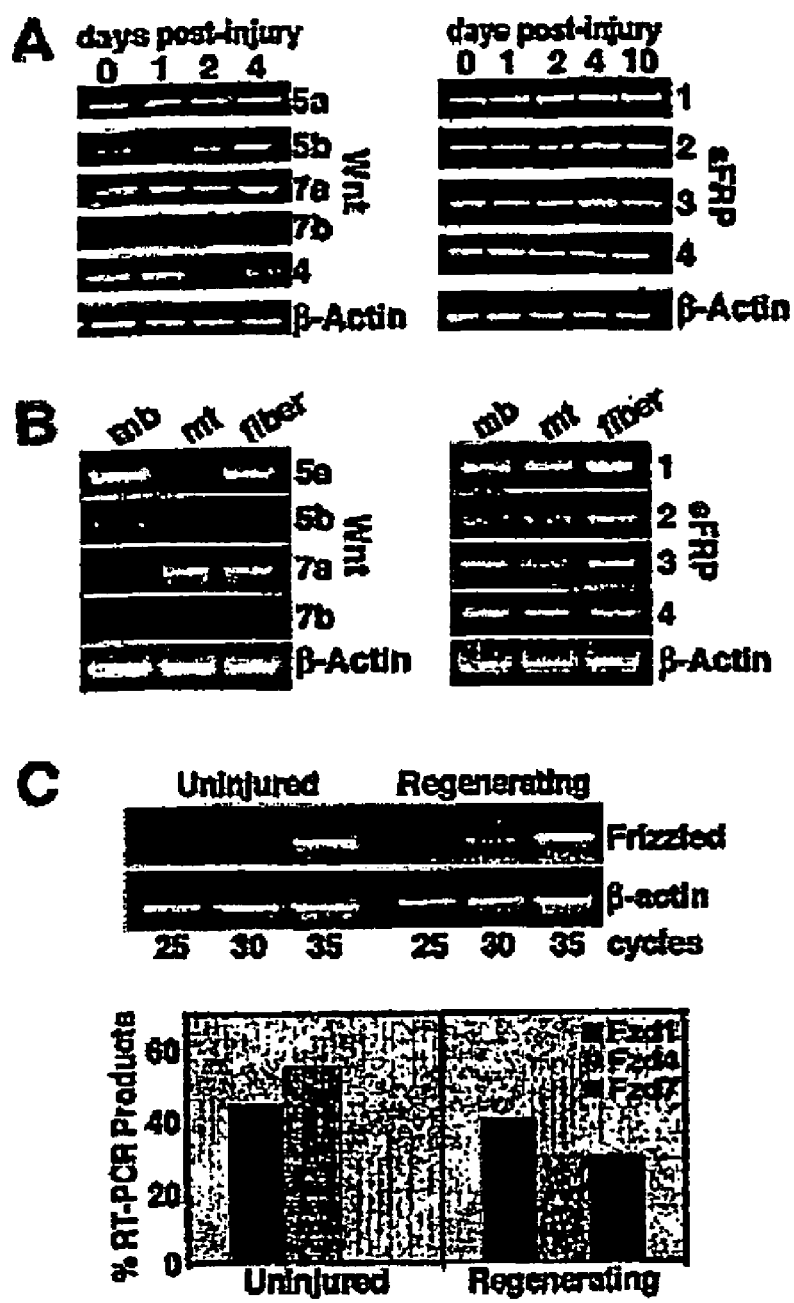
FIG. 3 depicts up-regulation of Wnts and sFRPs in regenerating muscle. (A) RT-PCR analysis indicated increased expression of Wnts 5a, 5b, 7a, 7b in regenerating TA muscle. By contrast, expression of Wnt4 was down-regulated following injury. Increased expression of sFRPs 1, 2, 3 but not sFRP4 was observed in regenerating muscle. (B) RT-PCR studies showed that Wnts 5a and 5b are expressed in muscle fibers (fiber) and proliferating myoblasts (mb); Wnt7a is primarily expressed in fibers and cultured myotubes (mt) (3 days of differentiation in culture). sFRPs 1-4 were expressed in myoblasts, myotubes and fibers. (C) Wnt receptors, Fzd 1,4 and Fzd 1,4,7 were expressed in purified CD45$^+$:Sca1$^+$ cells from uninjured and regenerating muscle (4 days post-injury) respectively.

To analyze the expression kinetics of genes in the Wnt-signalling cascade during skeletal muscle regeneration, semi-quantitative RT-PCR analysis was employed. The mRNAs for Wnt5a, 5b, 7a, and 7b were induced in regenerating muscle (4 days post-injury), whereas Wnt4 was strongly down-regulated (FIG. 3A). In a second experiment using re time PCR, the expression of genes in the Wnt-signalling cascade provided the following additional results listed in Table 3.

TABLE 3

Expression of Wnt Gene Products over Time

| Gene | Day 0 | Day 2 | Day 5 | Day 7 | Day 12 |
|------|-------|-------|-------|-------|--------|
| Wnt 1 | − | − | − | − | − |
| Wnt 2 | − | − | − | − | − |
| Wnt 5a | + | ++ | +++ | ++ | + |
| Wnt 5b | + | +++ | ++ | + | + |
| Wnt 7b | + | + | ++ | + | + |
| Wnt 10a | + | ++ | +++ | ++ | + |
| Wnt 10b | + | +++ | + | + | + |

To determine whether up-regulation of Wnts at the mRNA level corresponded to increased protein expression, Western Blot analysis of Wnt5a protein was performed. Wn5a was found to be strongly expressed from day 2 to day 10 of regeneration in two independent experiments. Wnt1 and Wnt3a were not expressed in any of the samples analyzed A strong but late induction of sFRPs 1, 2, and 3 but not of sFRP4 was observed (FIG. 3A). Fzds were not highly expressed in total muscle, and there was no induction during regeneration.

In addition, Affymetrix array experiments on regenerating mouse gastrocnemius muscle performed at the CNMC Microarray Center were analyzed. Gene expression was assayed in uninjured muscle (control) and at 12 hr, 1 day, 4 days, and 10 days post-ctx injection with 4 independent replicates performed for each time point (publicly available at http://microarray.cnmcresearchorg). Only genes that showed >2 fold expression changes between control and experimental samples (regenerating) following 4 possible pair-wise comparisons were studied fiber. Analysis of these data confirmed that Wnts 5a, 5b, 7a, and 7b, were up-regulated as early as 24 h post-injury, with high levels of expression maintained through the 10 day regeneration time-course. sFRPs, by contrast, were upregulated late in regeneration from day 4-day 10 post-injury. Specifically, sFRP1, 2 and 4 were up-regulated 7.3+/−1.2, 4.9+/−0.3 and 7.4+/−4.1 fold respectively at 10 days of regeneration relative to uninjured muscle (average of 4 pair-wise comparisons). In summary, the gene expression studies suggest possible roles for wnt polypeptides including Wnts 5a, 5b, 7a, 7b, 10a, and 10b in muscle regeneration.

Wnt and sFRP Expression in Myoblasts, Myotubes and Isolated Muscle Fibers

Given the capacity for CD45+:Sca1+ cells to undergo myogenic conversion in co-culture with primary myoblasts (FIG. 2), myoblasts, myotubes and myofibers were examined for the expression of Wnts and sFRPs. Importantly, Wnts5a and 5b were expressed in proliferating myoblasts, but not in differentiated myotubes. By contrast, Wnt7a was expressed in myotubes, but not in myoblasts (FIG. 3B). Interestingly, all three Wnts were expressed in isolated single muscle fibers. However, mRNA for Wnt7b was not detected in any sample. Lastly, sFRPs 1-4 were also expressed in myoblasts, myotubes, and muscle fibers (FIG. 3B). These results therefore suggest the hypothesis that expression of Wnt5a and Wnt5b in myoblasts induces the myogenic commitment of CD45+ adult stem cells in our co-culture experiments. Moreover, these data suggest that combined signaling by Wnts 5a, 5b, and 7a secreted by myofibers and myoblasts in regenerating muscle are responsible for the myogenic commitment of adult muscle-derived stem cells.

CD45+:Sca1+ Cells Express Frizzled-1, 4 and 7

If CD45+:Sca1+ cells represent the putative target for Wnts during muscle regeneration, it is predicted that CD45+:Sca1+ cells would express the Wnt-receptor Frizzled (Fzd). Therefore, CD45+:Sca1+ cells were isolated from r and regenerating TA muscle and examined for expression of Fzds. RT-PCR for Fzds was performed with fully degenerate primers followed by cloning and sequencing of PCR products. CD45+:Sca1+ cells from resting muscle were observed to express Fzd 1 and 4. By 4 days after ctx injection, CD45+:Sca1+ cells up-regulated Fzd expression overall and additionally expressed Fzd7 (FIG. 3C). Importantly, the observed up-regulation in the expression of Fzd mRNAs was specific to the CD45+:Sca1+ population as no change in Fzd mRNA expression was observed in RNA isolated from resting and regenerating total TA muscle.

CD45+:Sca1+ Cells Up-Regulate β-catenin During Muscle Regeneration

Figure 4:
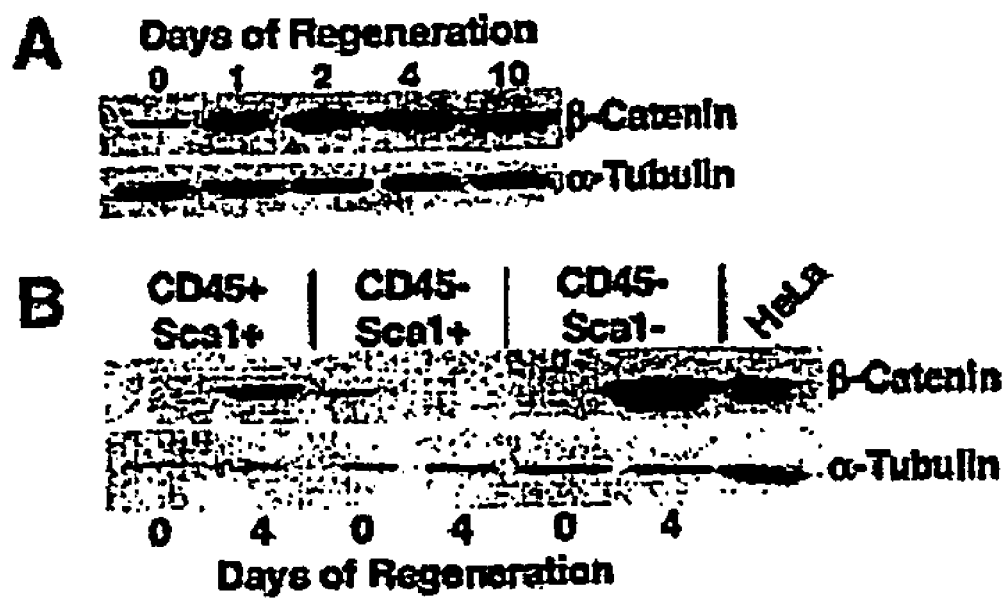
FIG. 4 depicts CD45$^+$:Sca-1$^+$ cells up-regulate β-catenin during regeneration. (A) Western blot analysis revealed increased levels of β-catenin protein in extracts of regenerating muscle. (B) High levels of β-catenin protein were observed in fractionated CD45$^+$:Sca1$^+$ and CD45$^-$:Sca1$^-$ cells from regenerating (4 days post-injury), but not uninjured skeletal muscle.

To determine whether Wnt signalling was activated in regenerating muscle, Western blot analysis was employed to detect β-catenin Stabilization and nuclear accumulation of β-catenin is the hallmark for activation of the canonical Wnt pathways in responder cells (Pandur, 2002, Bioassays 24, 881-884). β-catenin was strongly upregulated in extracts from total regenerating TA muscle relative to uninjured muscle (FIG. 4A). Importantly, expression of β-catenin protein was induced to high levels in CD45+:Sca1+ cells after muscle injury (FIG. 4B). By contrast, CD45−:Sca1+ cells did not express detectable levels of β-catenin. In regenerating muscle, the CD45−:Sca1− population, composed almost exclusively of myoblasts (unpublished observation), also expressed high levels of β-catenin. These data support the hypothesis that CD45+:Sca1+ cells respond to Wnt-signalling via the canonical Wnt-signalling pathways in regenerating TA muscle.

Ectopic Wnts Induce Myogenic Commitment of CD45+:Sca1+ Cells

Figure 5:
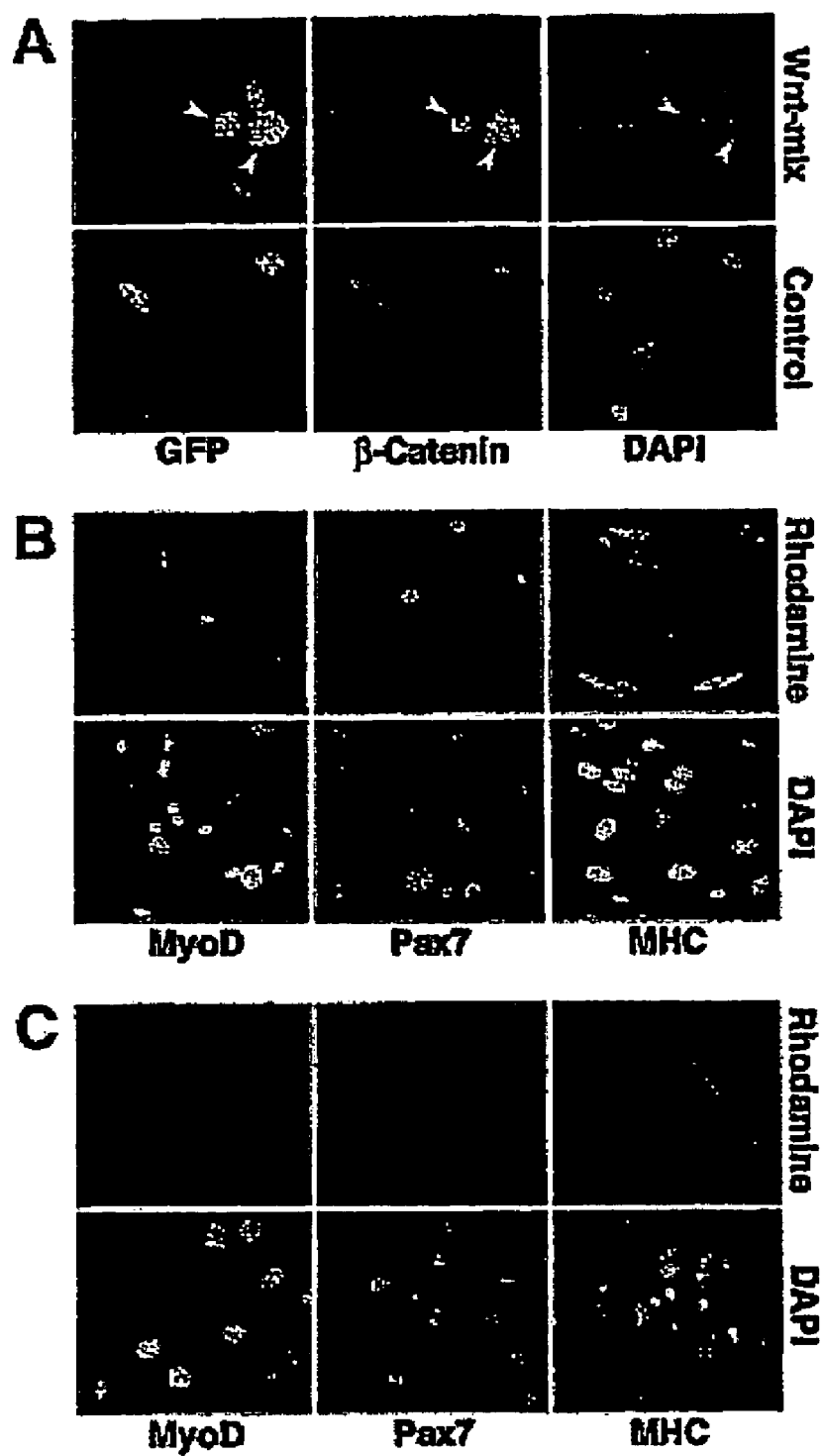
FIG. 5 depicts ectopic Wnts induce myogenic commitment of CD45$^+$:Sca1$^+$ cells. (A) BGFP expressing CD45$^+$:Sca1$^+$ cells from uninjured muscle displayed nuclear and/or cytoplasmic accumulation of β-catenin protein (arrowheads) after three days of co-culture with cell lines expressing Wnts 5a, 5b, 7a, and 7b (Wnt mix). By contrast, expression of β-catenin was confined to the plasma membrane in CD45$^+$:Sca1$^+$ co-cultured with cells transfected with empty pLNCX vector (control). (B) CD45$^+$:Sca1$^+$ cells expressed MyoD and Pax7 following three days of co-culture with Wnt 5a, 5b, 7a and 7b expressing cells. CD45$^+$:Sca1$^+$ cells differentiated as Myosin Heavy Chain (MHC) expressing myocytes following exposure of co-cultures to low-mitogen conditions. (C) CD45$^+$:Sca1$^+$ cells did not initiate expression of MyoD, Pax7 or MHC in co-culture with cell lines stably transfected with control empty vector (PLNCX).

To investigate whether Wnts were sufficient to induce myogenic conversion of CD45+;Sca1+ cells, a panel of stable cell lines were established that expressed recombinant HA-tagged Wnt proteins. Following co-culture with AtT-20 cells that expressed ectopic Wnts 5a, 5b, 7a, and 7b (Wnt mix), EGFP-expressing CD45+:Sca1+ cells displayed cytoplasmic and/or nuclear localization of β-catenin (arrowheads) consistent with activation of Wnt signalling in these cells (FIG. 5A). By contrast, CD45+:Sca1+ cells co-cultured with AtT-20 cells stably transfected with empty vector did not accumulate cytoplasmic or nuclear β-catenin (FIG. 5A).

In growth conditions, CD45+:Sca1+ cells co-cultured with Wnt lines initiated expression of the myogenic determination protein, MyoD, and the satellite cell marker Pax7 (FIG. 5B). In addition, MHC-positive myocytes were observed after the cultures were switched to differentiation conditions for 48 hours (FIG. 5B). By contrast, CD45+:Sca1+ cells co-cultured with control, non-Wnt expressing AtT-20 cells, did not express any myogenic markers (FIG. 5C). Thus, signalling by a mixture of Wnts 5a, 5b, 7a, and 7b led to myogenic commitment of CD45+:Sca1+ cells in vitro. Individual Wnt-expressing cell lines induced myogenic commitment of CD45+:Sca1+ cells but at a lower efficiency.

The plating efficiency of CD45+:Sca1+ cells was reproducibly 2-4% of input cells, about the same plating efficiency as observed with newly isolated primary myoblasts. After three days of culture, 2-4% of the number of input EGFP+CD45+:Sca1+ cells were present after co-culture with Wnt-expressing AtT-20 cells. Importantly, over 90% of surviving CD45+:Sca1+ cells converted to the myogenic lineage. Taken together, these experiments demonstrate that Wnt signalling activates myogenic specification of CD45+:Sca1+ cells isolated from uninjured muscle.

Injected sFRPs Severely Reduces the Myogenic Recruitment of CD45+:Sca1+ Cells During Regeneration To evaluate the relevance of Wnt signalling as an effector of muscle regeneration in vivo, recombinant Wnt-antagonists sFRP2 and 3 (100 ng of each) were injected on a daily basis into regenerating muscles of Myf5nlacZ mice. Three control animal groups were employed to assess possible extraneous effects. One group (uninjured control) was not injected with ctx, and did not receive subsequent sFRP injections. The second group received an initial injection of PBS rather than c followed by daily sFRP injections. The final group was injected with ctx to induce regeneration, followed by daily injection of PBS in the place of sFRPs.

Figure 6:
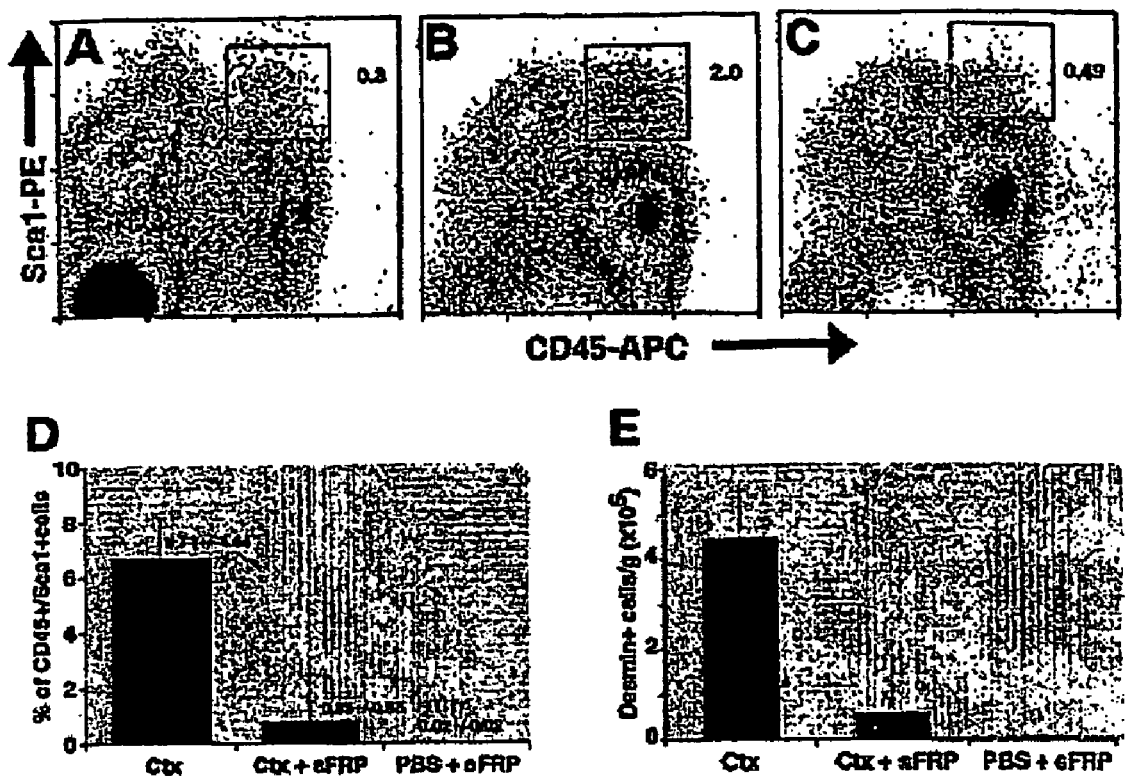
FIG. 6 depicts injection of sFRPs markedly decreases recruitment of CD45$^+$:Sca1$^+$ cells during regeneration. (A-C) Flow cytometric analysis for CD45 and Sca1 revealed a decreased proportion of CD45$^+$:Sca1$^{high}$ cells in regenerating muscle treated daily with sFRPs 2 and 3 (C) compared to regenerating muscle injected with PBS (B). Injection of sFRPs into uninjured muscle (A) did not induce regeneration or influence the proportions of CD45$^+$ and Sca1$^+$ cells. (D) The proportion of CD45$^+$:Sca1$^{high}$ cells that co-expressed Myf5LacZ was reduced by 6-fold following treatment of regenerating muscle with sFRPs 2 and 3. (E) A 7-fold reduction in the number of Desmin expressing myoblasts was recovered from regenerating muscle treated with sFRPs.
Figure 7:
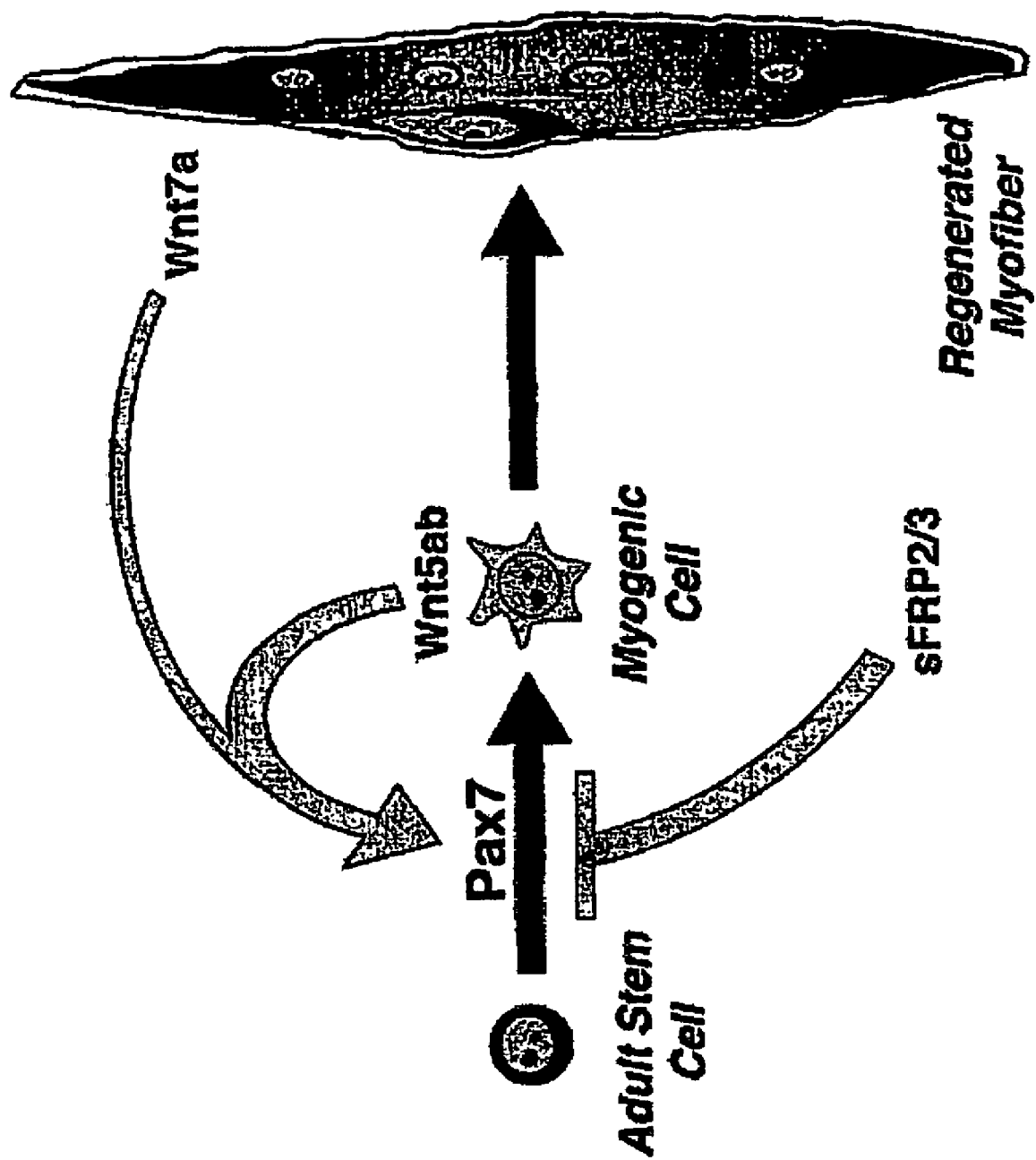
FIG. 7 depicts the role for Wnt signaling in myogenic recruitment of adult stem cells. The experiments suggest the hypothesis that Wnt signals secreted from damaged fibers, resident myoblasts and possibly other cell types in injured muscle induce the activation of myogenic transcription factors, and commitment of stem cells to muscle precursors. Wnt signaling may converge on activation of the Pax7 gene to induce myogenic specification Following repair, secretion of Wnt antagonists, sFRPs 2 and 3 block Wnt signals thereby interrupting the myogenic recruitment of stem cells.

Flow cytometric analysis of muscle cells demonstrated that the increase in the CD45+:Sca1$^{high}$ fraction observed 4 days following injury (FIG. 6B) was reduced about 4-fold by daily injections of sFRPs 2 and 3 (FIG. 6C). Furthermore, the reduced numbers of CD45+:Sca1$^{high}$ cells did not result from a concomitant decrease in total numbers of mononuclear cells. Importantly, injection of sFRPs into non-injured muscle did not induce regeneration, or produce any morphological changes in the TA muscle (FIG. 6A).

The proportion CD45+:Sca1+ cells expressing Myf5nLacZ was examined at 5 days following daily sFRP injections. As previously noted (FIG. 1), 6.71±1.44% of CD45+:Sca1$^{high}$ cells obtained directly from regenerating muscle 4 days after injury expressed Myf5nLacZ (n=3) (FIG. 6B). Importantly, A nLacZ was not expressed in CD45+:Sca1+ cells isolated from uninjured muscle (FIG. 6D). Strikingly, daily injection of sFRP 2 and 3 into regenerating muscle resulted in about a six-fold reduction in the numbers of Myf5nLacZ+ cells in the CD45+:Sca1+ fraction (FIG. 6D). Thus, inhibition of Wnt signalling markedly reduced myogenic specification of CD45+:Sca1+ cells in vivo.

To further characterise the effect of sFRPs on muscle regeneration, the recovery of myogenic cells in the total pool of mononuclear cells from muscle 4 days post-injury was analyzed 1×10$^4$ cells from the three experimental groups were plated in each well and analyzed 24 hours later for expression of Desmin, a marker specific to skeletal muscle cells (FIG. 6E). Daily sFRPs injection produced about a 7-fold decrease in the number of mononuclear Desmin expressing myoblasts in 4 day regenerating TA muscle relative to PBS-injected regenerating muscle (4.47×10$^5$+/−1×10$^5$ compared to 6.03×10$^4$+/−3.03×10$^4$ cells/gram tissue) (FIG. 6E).

In Vivo LiCl Treatment of Animals.

8-10 week old male Myf5nLacZ mice were separated in 2 groups. The fist group (n=3) received intraperitoneal injection of lithium chloride (2 mg/kg/day in a volume of about 100 µL) (Sigma) and the second (n=3) received saline injection (100 µL/day) for 14 days. Ten days after initiation of the treatment, regeneration was induced with cardiotoxin injection (25 µl of 10 µM cardiotoxin (Laxotan) injected directly in the TA muscle using a 29G ½ insulin syringe).

For analysis of total mononuclear cell population, TA were rested, mechanically dissociated and digested with Collagenase-Dispase as previousky described (Megeney, L. A., Kablar, B., Ga Fett, K, Anderson, J. E., Rudnicki M. A. (1996), MyoD is required for myogenic stem cell function in adult skeletal muscle. Genes Dev 10, 1173-1183, which is herein incorporated by reference). 2×10$^5$ cells were plated on collagen-coates chambers slides overnight, then fixed in 4%, paraformaldehyde for 10 minutes and stained overnight with an X-gal containing solution. The results are depicted in FIG. 8.

Effect of Wnt-Protein Expression on Primary Myoblast Cells

Figure 9:
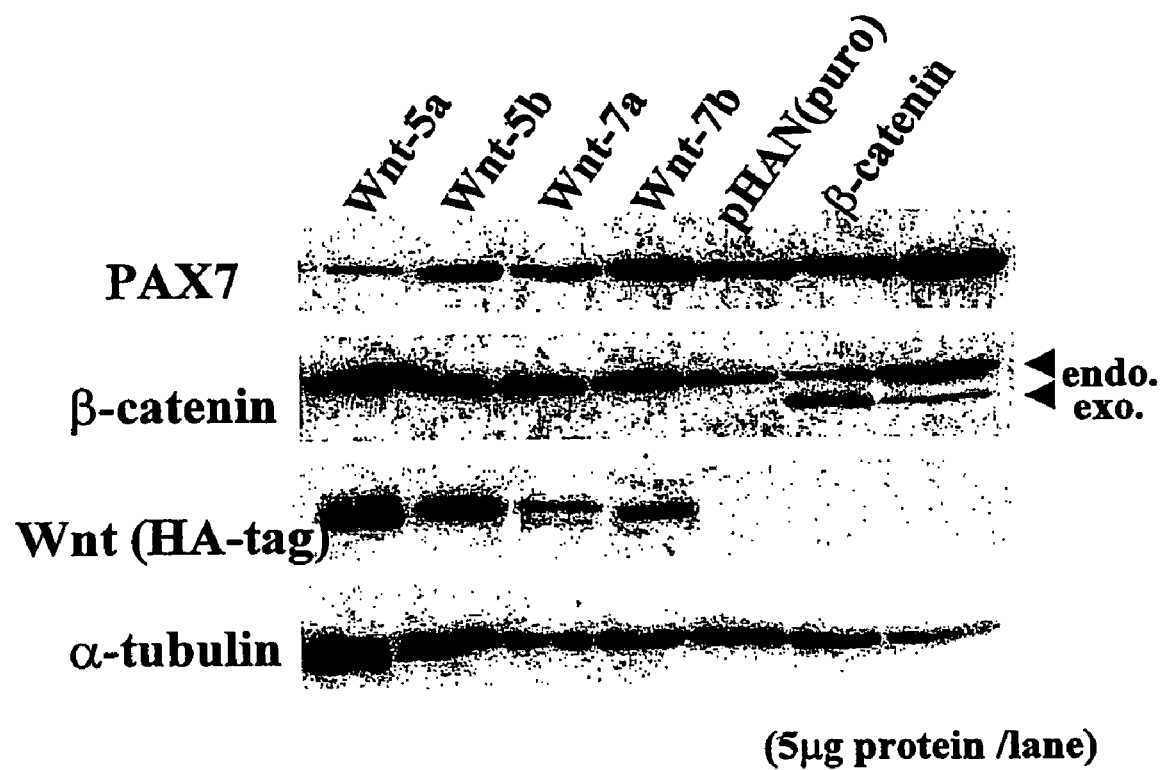
FIG. 9 shows Western blot results demonstrating that wnt polypeptides modulate Pax 7 expression in primary myoblast cells.

In an alternate experiment, the cDNA fragments of Wnt-5a, -5b, -7b, β-catenin and β-catein-IRES-lef1 were subcloned into retrovirus vector, pHAN(puro). To prepare ecotropic retrovirus, Phoenix-eco packaging cells were transfected with retrovirus vectors by using lipofectoAMINE (Invitrogen). Viral supernatants were harvested 30 hrs post-transfection and used to infect primary myoblast cells in the presence of polybrene (Sigma, 8 mg/ml). Infected cells were selected 24 hrs postinfection with puromycin (Sigma, 1 mg/ml). Selected primary myoblast were grown in 100-mm dishes, washed twice with PBS and lysed in 100 ml radioimmunoprecipitation assay (RIPA) buffer (50 mM Tris HCl, pH 7.5, 150 mM NaCl; 0.5% Nonidet P-40; 0.1% deoxycholate) containing protease inhibitor cocktail (Roche). Cell extracts were collected and spun in a microcentrifuge at 13,000 rpm for 5 min. Total proteins (5 µg) were separated by 10% SDS-PAGE and transferred to Immobilon-P (Millipore). The membranes were probed with primary antibodies, followed by HRP-conjugated secondary antibodies at 1:5,000 (Bio-Rad), and developed using ECL™ Plus (Amersham Biosciences). Membranes were exposed to BIOMAX film (Kodak). Friary antibodies used in this work: anti-PAX7 (1:2), β-catenin (BD Bioscience, 1:2,000), anti-HA (Sigma, 1:5,000) and anti-α-tublin (Sigma, 1:4,000). The results are depicted in FIG. 9.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

All citations are herein incorporated by reference.

The present invention has been described with regard to preferred embodiments, but it will be obvious to persons skilled in the art that a number of variations and modifications can be made without departing from the scope of the invention as described and claimed herein.

What is claimed is:

1. An in-vitro method of promoting or inhibiting proliferation, differentiation or both proliferation and differentiation of a population of CD45+: Sca1+ muscle stem cells comprising, administering a composition comprising one or more activators or inhibitors of wnt-signaling to said stem cells to promote proliferation or differentiation thereof.

2. The method of claim 1, wherein said composition comprises one or more wnt-signaling activators in the form of one or more wnt polypeptides or one or more compounds that bind to and inhibit the activity of one or more soluble Frizzled-related proteins.

3. The method of claim 2, wherein said wnt-signaling activators are in the form of one or more human wnt polypeptides comprising Wnt 1, Wnt 2, Wnt 3, Wnt 4, Wnt 5a, Wnt 5b, Wnt 7a, Wnt 7b, Wnt 10a, Wnt 10b, or a combination thereof.

4. The method of claim 2, wherein said wnt-signaling activators are in the form of one or more polypeptides or antibodies or antibody fragments thereof 5. The method of claim 1, said composition comprises one or more inhibitors of wnt-signaling in the form of one or more soluble Frizzled-related proteins.

6. The method of claim 5, wherein said one or more soluble Frizzled-related proteins comprise human Frizzled-related proteins, sFRP1, sFRP2, sFRP3, sFRP4, or a combination thereof.

7. The method of claim 1, wherein said stem cells are from a mammalian subject that exhibits or has muscle degeneration or muscle wasting optionally due to a muscular degenerative disease.

8. The method of claim 7, wherein said subject has aids, cancer, type II diabetes, or a combination thereof or has a muscular degenerative disease selected from the group consisting of Duchenne muscular dystrophy (DMD), Becker muscular dystrophy (BMD), myotonic dystrophy (Steinert's disease), limb-girdle muscular dystrophies, facioscapulo-humeral muscular dystrophy (FSH), congenital muscular dystrophies, oculopharyngeal muscular dystrophy (OPMD), distal muscular dystrophies and Emery-Dreifuss muscular dystrophy.

9. The method of claim 2, wherein said composition further comprises a helper compound that enhances the survival of said stem cells.

10. The method of claim 9, wherein said helper compound comprises a sonic hedgehog (Shh) protein.

11. An in-vitro method of promoting proliferation of a population of CD45+: Sca1 + adult muscle stem cells comprising contacting said population with one or more activators of Wnt-signaling pathways to promote proliferation of said cells.

12. An in-vitro method of inducing the lineage commitment of a population of CD45+: Sca1+ muscle stem cells into progenitor cells which comprises contacting said stem cells with a composition that comprises one or more activators of the Wnt -signaling pathways to induce the lineage commitment of said cells.

13. An in-vitro method of increasing the survival of a population of CD45+: Sca1+ muscle stem cells which comprises contacting said population with a composition that comprises one or more activators of the Wnt-signaling pathways to increase the survival of said cells.

* * * * *

UNITED STATES PATENT AND TRADEMARK OFFICE
CERTIFICATE OF CORRECTION

PATENT NO. : 7,541,183 B2  Page 1 of 1
APPLICATION NO. : 11/318419
DATED : June 2, 2009
INVENTOR(S) : Rudnicki et al.

It is certified that error appears in the above-identified patent and that said Letters Patent is hereby corrected as shown below:

<u>Title Page</u>:
Item (56) References cited, OTHER PUBLICATIONS:
Gallicchio et al. reference, after "Blood", change "53" to -- 56 --.
M.A. Rudnicki reference, after "Molecular", insert -- Regulation --.
A. Gritti et al. reference, change "Mitrogenic" to -- Mitogenic --.

<u>Column 69</u>:
Line 7 (claim 1, line 6), after "promote", insert -- or inhibit --.
Line 19 (claim 4, line 3), after "thereof", insert -- . --.

Signed and Sealed this

Fourteenth Day of July, 2009

JOHN DOLL
*Acting Director of the United States Patent and Trademark Office*